(12) United States Patent
Lakshmana et al.

(10) Patent No.: US 9,994,536 B2
(45) Date of Patent: Jun. 12, 2018

(54) COMPOUNDS AND METHODS OF TREATING NEUROLOGICAL DISORDERS

(71) Applicant: TORREY PINES INSTITUTE FOR MOLECULAR STUDIES, Port St. Lucie, FL (US)

(72) Inventors: Madepalli K. Lakshmana, Port St. Lucie, FL (US); Adel Nefzi, Port St. Lucie, FL (US); Richard Houghten, Port St. Lucie, FL (US); Dmitriy Minond, Boca Raton, FL (US)

(73) Assignee: Torrey Pines Institute for Molecular Studies, Port St. Lucie, FL (US)

( * ) Notice: Subject to any disclaimer, the term of this patent is extended or adjusted under 35 U.S.C. 154(b) by 0 days. days.

(21) Appl. No.: 15/306,824

(22) PCT Filed: May 1, 2015

(86) PCT No.: PCT/US2015/028739
§ 371 (c)(1),
(2) Date: Oct. 26, 2016

(87) PCT Pub. No.: WO2015/168518
PCT Pub. Date: Nov. 5, 2015

(65) Prior Publication Data
US 2017/0121296 A1 May 4, 2017

Related U.S. Application Data

(60) Provisional application No. 61/987,525, filed on May 2, 2014.

(51) Int. Cl.
*C07D 277/42* (2006.01)
(52) U.S. Cl.
CPC .................. *C07D 277/42* (2013.01)
(58) Field of Classification Search
CPC .................................................... C07D 277/42
USPC ...................................................... 514/236.8
See application file for complete search history.

(56) References Cited

U.S. PATENT DOCUMENTS

| | | | |
|---|---|---|---|
| 2,636,037 A | 4/1953 | Sprague et al. | |
| 4,742,057 A | 5/1988 | Ueda et al. | |
| 4,921,887 A | 5/1990 | Matsuo et al. | |
| 5,369,107 A | 11/1994 | Matsuo et al. | |
| 2015/0315179 A1 | 11/2015 | Lakshmana et al. | |

FOREIGN PATENT DOCUMENTS

WO 2010028193 A1 3/2010

OTHER PUBLICATIONS

F. Fahrenholz, Alpha-Secretase as a Therapeutic Target, Current Alzheimer Research, vol. 4, Issue 4 (2007) 412-417.

E. Chakrabarti, S. Ghosh, S. Sadhukhan, L. Sayre, G.P. Tochtrop, J.D. Smith, Synthesis and biological evaluation of analogues of a novel inhibitor of beta-amyloid secretion, J Med Chem, 53 (Jul. 2010) 5302-5319.
S.P. Braithwaite, R.S. Schmid, D.N. He, M.L. Sung, S. Cho, L. Resnick, M.M. Monaghan, W.D. Hirst, C. Essrich, P.H. Reinhart, D.C. Lo, Inhibition of c-Jun kinase provides neuroprotection in a model of Alzheimer's disease, Neurobiol Dis, 39 (Sep. 2010) 311-317.
M.S. Wolfe, gamma-Secretase inhibitors and modulators for Alzheimer's disease, J Neurochem, 120 Suppl 1 (2012) 89-98.
A.K. Ghosh, M. Brindisi, J. Tang, Developing beta-secretase inhibitors for treatment of Alzheimer's disease, J Neurochem, 120 Suppl 1 (2012) 71-83.
D. Puzzo, A. Staniszewski, S.X. Deng, L. Privitera, E. Leznik, S. Liu, H. Zhang, Y. Feng, A. Palmeri, D.W. Landry, O. Arancio, Phosphodiesterase 5 inhibition improves synaptic function, memory, and amyloid-beta load in an Alzheimer's disease mouse model, J Neurosci, 29 (2009) 8075-8086.
A.P. Kozikowski, Y. Chen, T. Subhasish, N.E. Lewin, P.M. Blumberg, Z. Zhong, M.A. D'Annibale, W.L. Wang, Y. Shen, B. Langley, Searching for disease modifiers-PKC activation and HDAC inhibition—a dual drug approach to Alzheimer's disease that decreases Abeta production while blocking oxidative stress, ChemMedChem, 4 (2009) 1095-1105.
S.F. Lichtenthaler, alpha-secretase in Alzheimer's disease: molecular identity, regulation and therapeutic potential, J Neurochem, 116 (2011) 10-21.
S. Bandyopadhyay, L.E. Goldstein, D.K. Lahiri, J.T. Rogers, Role of the APP non-amyloidogenic signaling pathway and targeting alpha-secretase as an alternative drug target for treatment of Alzheimer's disease, Curr Med Chem, 14 (2007) 2848-2864.
E.Y. Huang, A.M. Gallegos, S.M. Richards, S.M. Lehar, M.J. Bevan, Surface expression of Notch1 on thymocytes: correlation with the double-negative to double-positive transition, J Immunol, 171 (2003) 2296-2304.
O.A. Levy, J.J. Lah, A.I. Levey, Notch signaling inhibits PC12 cell neurite outgrowth via RBP-J-dependent and -independent mechanisms, Dev Neurosci, 24 (2002) 79-88.
A. Corbett, J. Smith, C. Ballard, New and emerging treatments for Alzheimer's disease, Expert Rev Neurother, 12 (2012) 535-543.
R. Postina, Activation of alpha-secretase cleavage, J Neurochem, 120 Suppl 1 (2012) 46-54.
M. Bielefeld-Sevigny, AlphaLISA immunoassay platform—the "no-wash" high-throughput alternative to ELISA, Assay Drug Dev Technol, 7 (2009) 90-92.
E. Cauchon, S. Liu, M.D. Percival, S.E. Rowland, D. Xu, C. Binkert, P. Strickner, J.P. Falgueyret, Development of a homogeneous immunoassay for the detection of angiotensin I in plasma using AlphaLISA acceptor beads technology, Anal Biochem, 388 (2009) 134-139.
D.M. Chau, D. Shum, C. Radu, B. Bhinder, D. Gin, M.L. Gilchrist, H. Djaballah, Y.M. Li, A novel high throughput 1536-well Notch1 gamma-secretase AlphaLISA assay, Comb Chem High Throughput Screen, 16 (2013) 415-424.

(Continued)

*Primary Examiner* — Kristin A Vajda
(74) *Attorney, Agent, or Firm* — Thomas | Horstemeyer, LLP

(57) ABSTRACT

Embodiments of the present disclosure provide for compositions including a compound, pharmaceutical compositions including the compound, methods of treatment of a disease or related condition (e.g., neurological disease on condition), methods of treatment using compositions or pharmaceutical compositions, and the like.

8 Claims, 48 Drawing Sheets

(56) References Cited

OTHER PUBLICATIONS

G. Cosentino, AlphaLISA assays to improve the vaccine development process, Dev Biol (Basel), 134 (2012) 107-111.
A. Mechaly, N. Cohen, S. Weiss, E. Zahavy, A novel homogeneous immunoassay for anthrax detection based on the AlphaLISA method: detection of B. anthracis spores and protective antigen (PA) in complex samples, Anal Bioanal Chem, 405 (2013) 3965-3972.
C.D. Peters, B. Jespersen, R. Norregaard, AlphaLISA versus ELISA-based detection of interleukin 18 in healthy subjects and patients with end-stage renal disease, Scand J Clin Lab Invest, 72 (2012) 583-592.
M. Pfluger, A. Kapuscik, R. Lucas, A. Koppensteiner, M. Katzlinger, J. Jokela, A. Eger, N. Jacobi, C. Wiesner, E. Hofmann, K. Onder, J. Kopecky, W. Schutt, H. Hundsberger, A combined impedance and AlphaLISA-based approach to identify anti-inflammatory and barrier-protective compounds in human endothelium, J Biomol Screen, 18 (2013) 67-74.
S. Schneider, H. Chen, J. Tang, R. Emkey, P.S. Andrews, Development of a homogeneous AlphaLISA ubiquitination assay using ubiquitin binding matrices as universal components for the detection of ubiquitinated proteins, Biochim Biophys Acta, 1823 (2012) 2038-2045.
J.R. Simard, M. Plant, R. Emkey, V. Yu, Development and implementation of a high-throughput AlphaLISA assay for identifying inhibitors of EZH2 methyltransferase, Assay Drug Dev Technol, 11 (2013) 152-162.
H. Waller, U. Chatterji, P. Gallay, T. Parkinson, P. Targett-Adams, The use of AlphaLISA technology to detect interaction between hepatitis C virus-encoded NS5A and cyclophilin A, J Viral Methods, 165 (2010) 202-210.
C.L. Wen, K.Y. Chen, C.T. Chen, J.G. Chuang, P.C. Yang, L.P. Chow, Development of an AlphaLISA assay to quantify serum core-fucosylated E-cadherin as a metastatic lung adenocarcinoma biomarker, J Proteomics, 75 (2012) 3963-3976.
Y. Zhang, B. Huang, J. Zhang, K. Wang, J. Jin, Development of a homogeneous immunoassay based on the AlphaLISA method for the detection of chloramphenicol in milk, honey and eggs, J Sci Food Agric, 92 (2012) 1944-1947.
L.P. Zou, T.C. Liu, G.F. Lin, Z.N. Dong, J.Y. Hou, M. Li, Y.S. Wu, AlphaLISA for the determination of median levels of the free beta subunit of human chorionic gonadotropin in the serum of pregnant women, J Immunoassay Immunochem, 34 (2013) 134-148.
E.H. Koo, S.L. Squazzo, Evidence that production and release of amyloid beta-protein involves the endocytic pathway, J Biol Chem, 269 (1994) 17386-17389.
C.D. Hayes, D. Dey, J.P. Palavicini, H. Wang, K.A. Patkar, D. Minond, A. Nefzi, M.K. Lakshmana, Striking reduction of amyloid plaque burden in an Alzheimer's mouse model after chronic administration of carmustine, BMC Med, 11 (2013) 81.
J.H. Zhang, T.D. Chung, K.R. Oldenburg, A Simple Statistical Parameter for Use in Evaluation and Validation of High Throughput Screening Assays, J Biomol Screen, 4 (1999) 67-73.
P. Hodder, J. Cassaday, R. Peltier, K. Berry, J. Inglese, B. Feuston, C. Culberson, L. Bleicher, N.D. Cosford, C. Bayly, C. Suto, M. Varney, B. Strulovici, Identification of metabotropic glutamate receptor antagonists using an automated high-throughput screening system, Anal Biochem, 313 (2003) 246-254.
M.K. Lakshmana, I.S. Yoon, E. Chen, E. Bianchi, E.H. Kao, D.E. Kang, Novel role of RanBP9 in BACE1 processing of amyloid precursor protein and amyloid beta peptide generation, J Biol Chem, 284 (2009) 11863-11872.
Z.X. Yao, Z. Han, K. Drieu, V. Papadopoulos, Ginkgo biloba extract (Egb 761) inhibits beta-amyloid production by lowering free cholesterol levels, J Nutr Biochem, 15 (2004) 749-756.
S. Tokuhiro, T. Tomita, H. Iwata, T. Kosaka, T.C. Saido, K. Maruyama, T. Iwatsubo, The presenilin 1 mutation (M146V) linked to familial Alzheimer's disease attenuates the neuronal differentiation of NTera 2 cells, Biochem Biophys Res Commun, 244 (1998) 751-755.
S.M. Cardoso, I. Santana, R.H. Swerdlow, C.R. Oliveira, Mitochondria dysfunction of Alzheimer's disease cybrids enhances Abeta toxicity, J Neurochem, 89 (2004) 1417-1426.
L.B. Yang, R. Li, S. Med, J. Rogers, Y. Shen, Deficiency of complement defense protein CD59 may contribute to neurodegeneration in Alzheimer's disease, J Neurosci, 20 (2000) 7505-7509.
P.W. Andrews, I. Damjanov, D. Simon, G.S. Banting, C. Carlin, N.C. Dracopoli, J. Fogh, Pluripotent embryonal carcinoma clones derived from the human teratocarcinoma cell line Tera-2. Differentiation in vivo and in vitro, Lab Invest, 50 (1984) 147-162.
S.J. Pleasure, C. Page, V.M. Lee, Pure, postmitotic, polarized human neurons derived from NTera 2 cells provide a system for expressing exogenous proteins in terminally differentiated neurons, J Neurosci, 12 (1992) 1802-1815.
A.S. Chyung, B.D. Greenberg, D.G. Cook, R.W. Doms, V.M. Lee, Novel beta-secretase cleavage of beta-amyloid precursor protein in the endoplasmic reticulum/intermediate compartment of NT2N cells, J Cell Biol, 138 (1997) 671-680.
Y.M. Sung, T. Lee, H. Yoon, A.M. DiBattista, J.M. Song, Y. Sohn, E.I. Moffat, R.S. Turner, M. Jung, J. Kim, H.S. Hoe, Mercaptoacetamide-based class II HDAC inhibitor lowers Abeta levels and improves learning and memory in a mouse model of Alzheimer's disease, Exp Neurol, 239 (2013) 192-201.
J.E. Hanson, H. La, E. Plise, Y.H. Chen, X. Ding, T. Hanania, E.V. Sabath, V. Alexandrov, D. Brunner, E. Leahy, P. Steiner, L. Liu, K. Scearce-Levie, Q. Zhou, SAHA enhances synaptic function and plasticity in vitro but has limited brain availability in vivo and does not impact cognition, PLoS One, 8 (2013) e69964.
Y. Su, J. Ryder, B. Li, X. Wu, N. Fox, P. Solenberg, K. Brune, S. Paul, Y. Zhou, F. Liu, B. Ni, Lithium, a common drug for bipolar disorder treatment, regulates amyloid-beta precursor protein processing, Biochemistry, 43 (2004) 6899-6908.
T. Schroter, D. Minond, A. Weiser, C. Dao, J. Habel, T. Spicer, P. Chase, P. Baillargeon, L. Scampavia, S. Schurer, C. Chung, C. Mader, M. Southern, N. Tsinoremas, P. LoGrasso, P. Hodder, Comparison of miniaturized time-resolved fluorescence resonance energy transfer and enzyme-coupled luciferase high-throughput screening assays to discover inhibitors of Rho-kinase II (ROCK-II), J Biomol Screen, 13 (2008) 17-28.
International Search Report for PCT/US2015/028739 dated Jul. 21, 2015.
Craver et al., Journal of the American Pharmaceutical Association (1912-1977), 1951, 40, pp. 333-339.
Lundina et al., Chemistry of Heterocyclic Compounds, Jul. 1967, vol. 3, Issue 4, pp. 201-204—(Khimiya Geterotsiklicheskikh Soedinenii, (1967), 2, pp. 266-260).
PubChem CID 71304497—National Center for Biotechnology Information. PubChem Compound Database; CID=71304497, http://pubchem.ncbi.nlm.nih.gov/summary/summary.
cgi?cid=71304497 (accessed Oct. 16, 2015), create date Apr. 24, 2013.
Chemical Abstracts Registry No. 1537989-64-2 {indexed in the Registry file on STN CAS ONLINE Feb. 6, 2014.

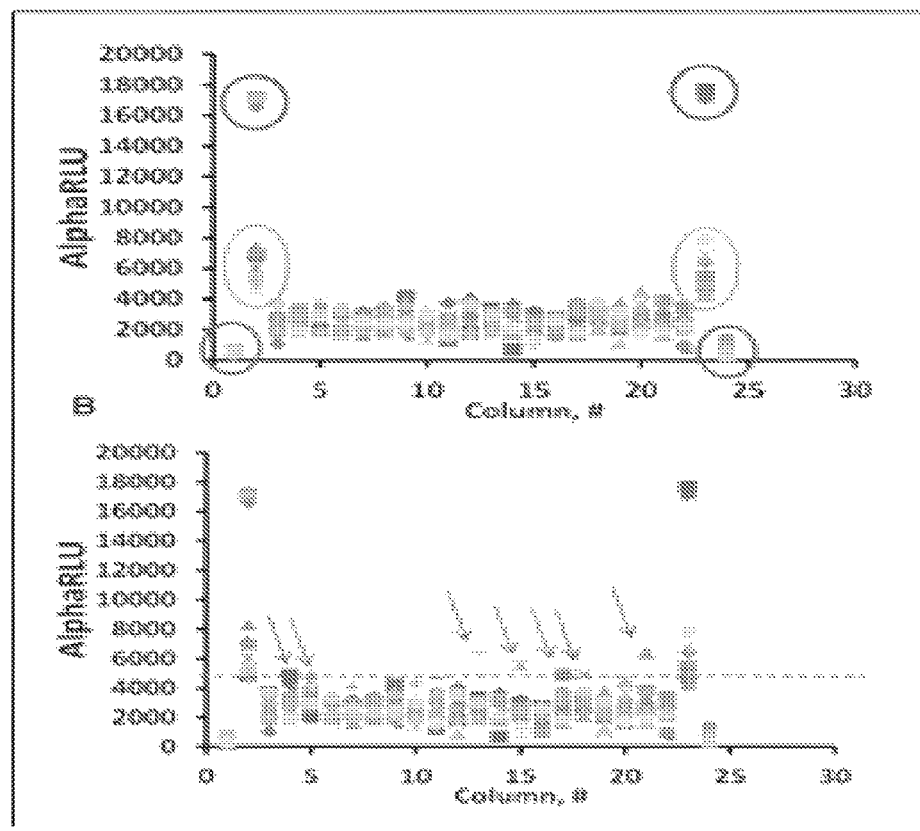
Fig. 1.1
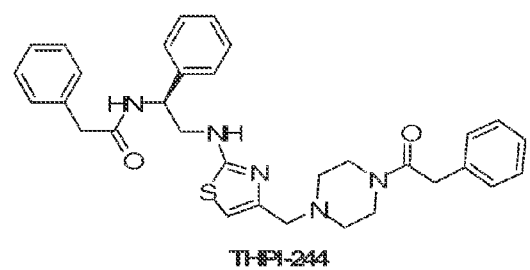
Fig. 1.2

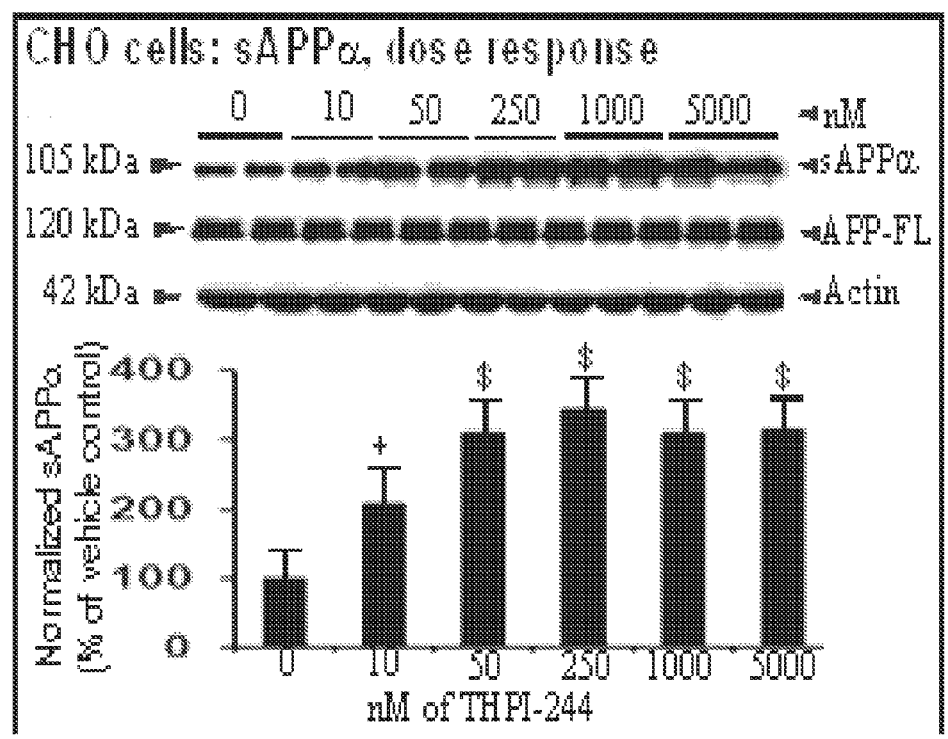
Fig. 1.3

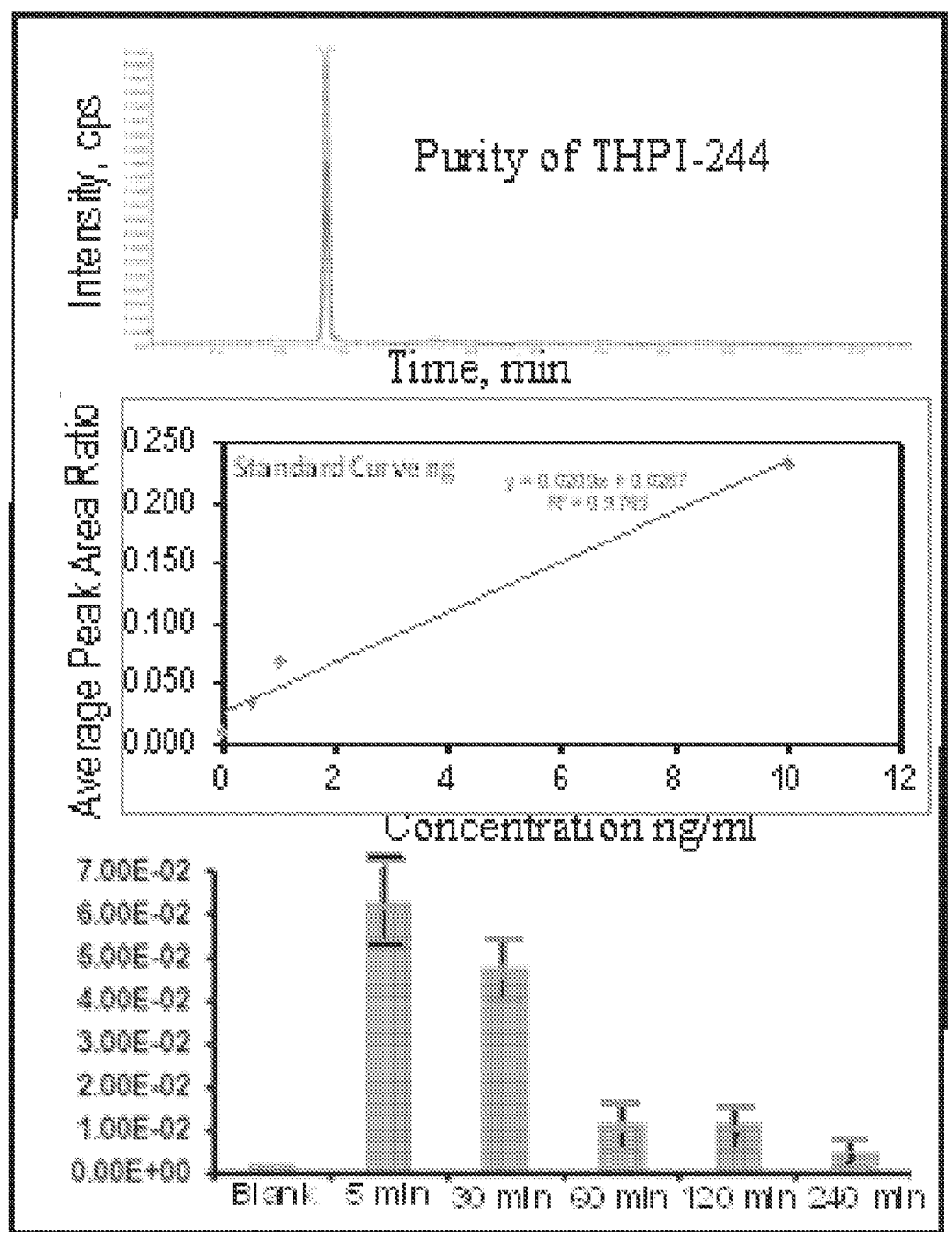
Fig. 1.4

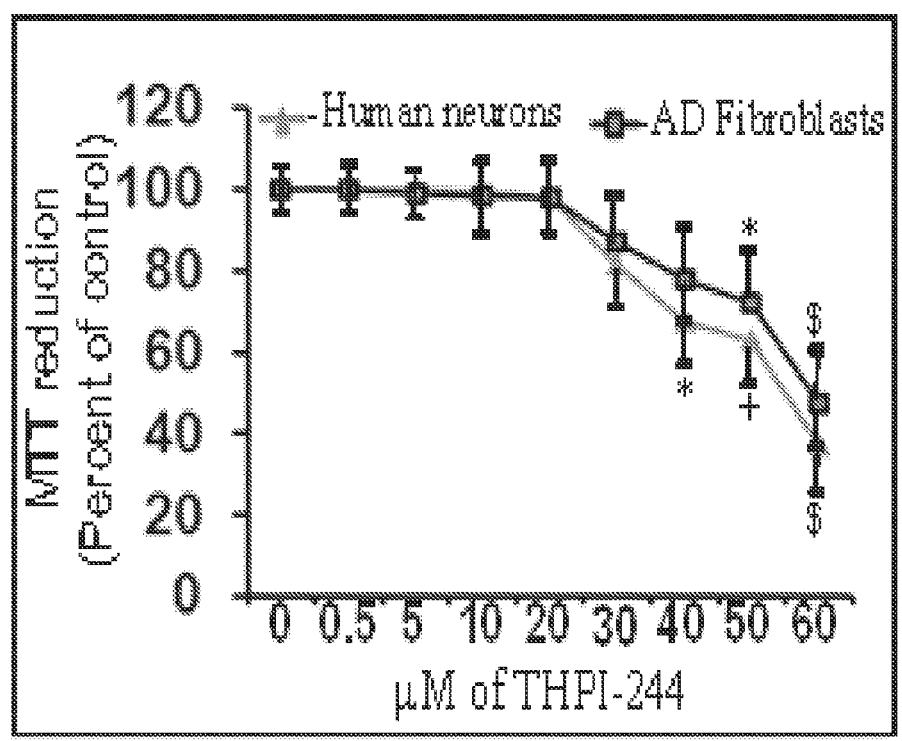
Fig. 1.5

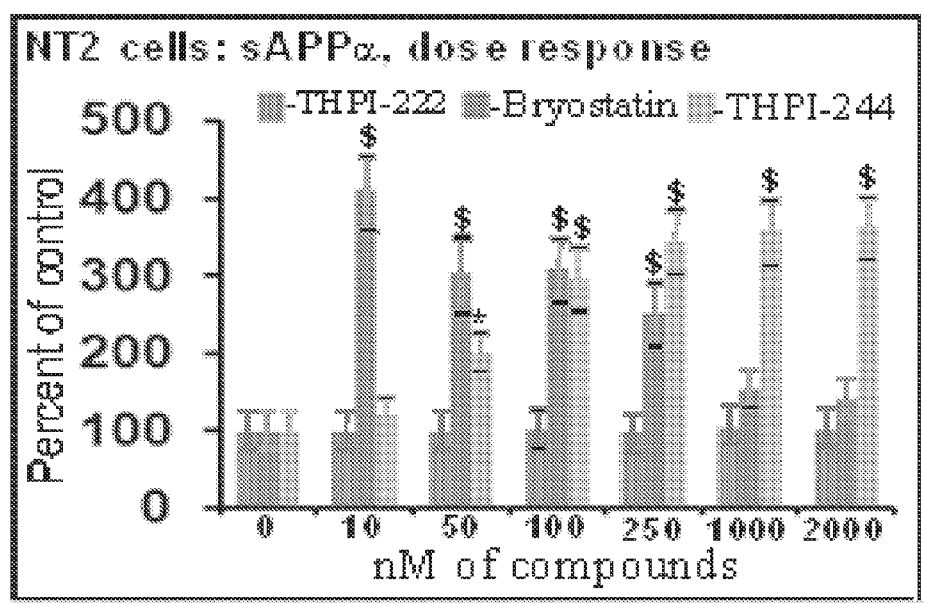
Fig. 1.6

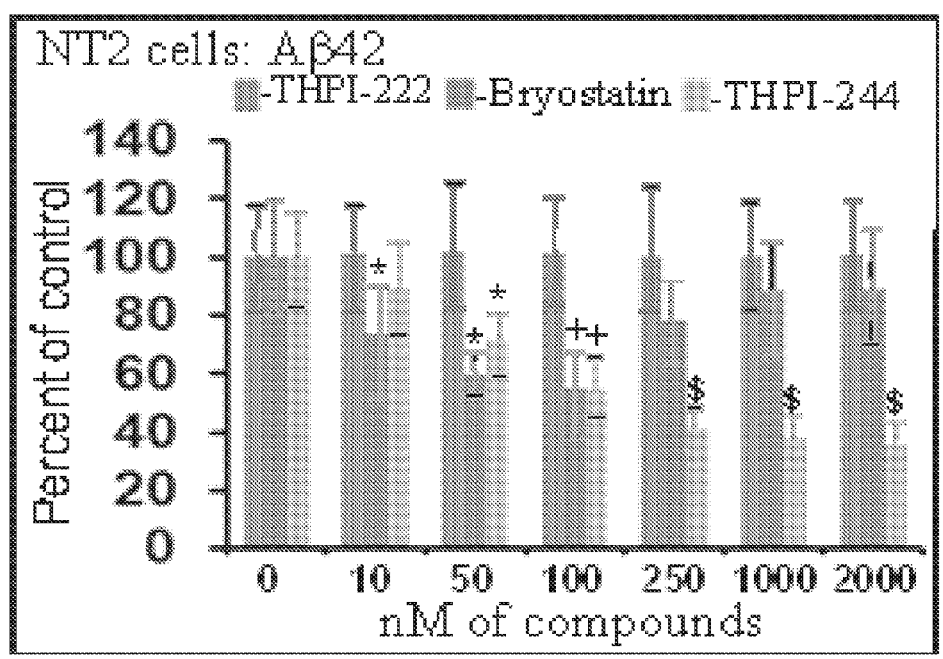
Fig. 1.7

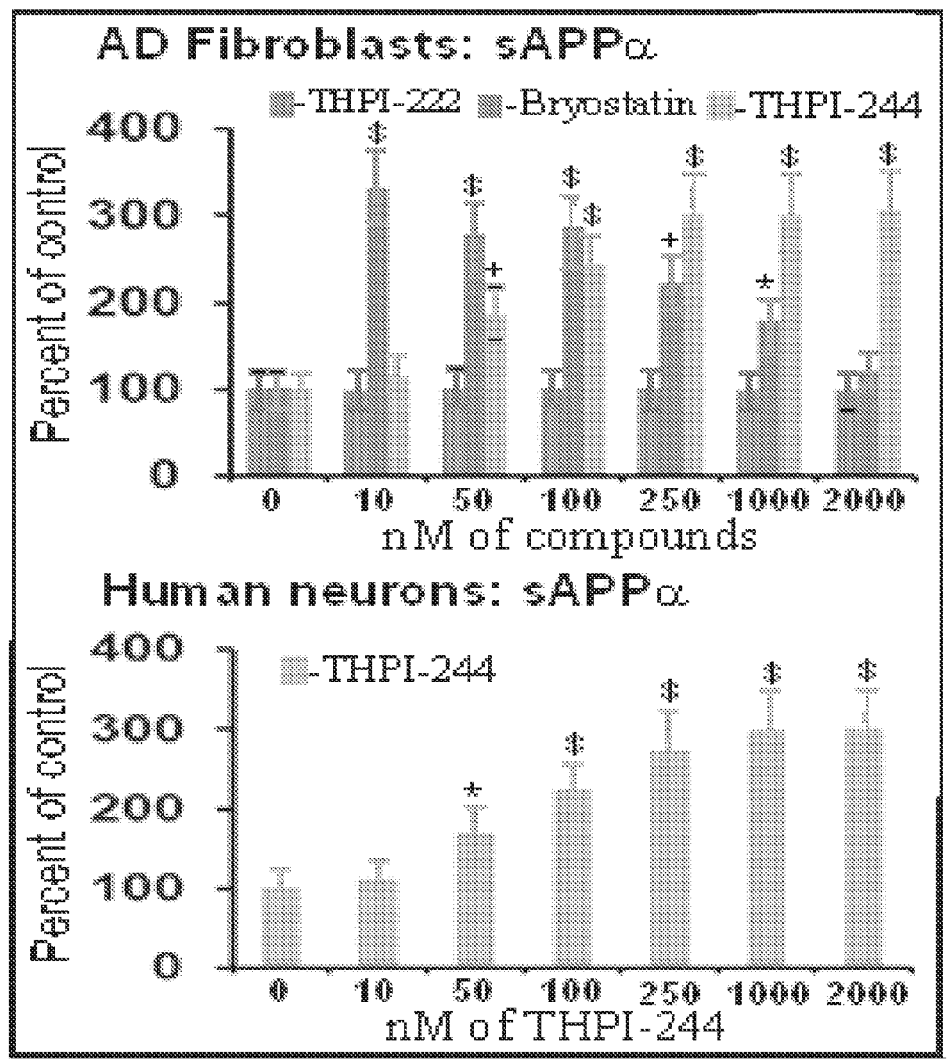
Fig. 1.8

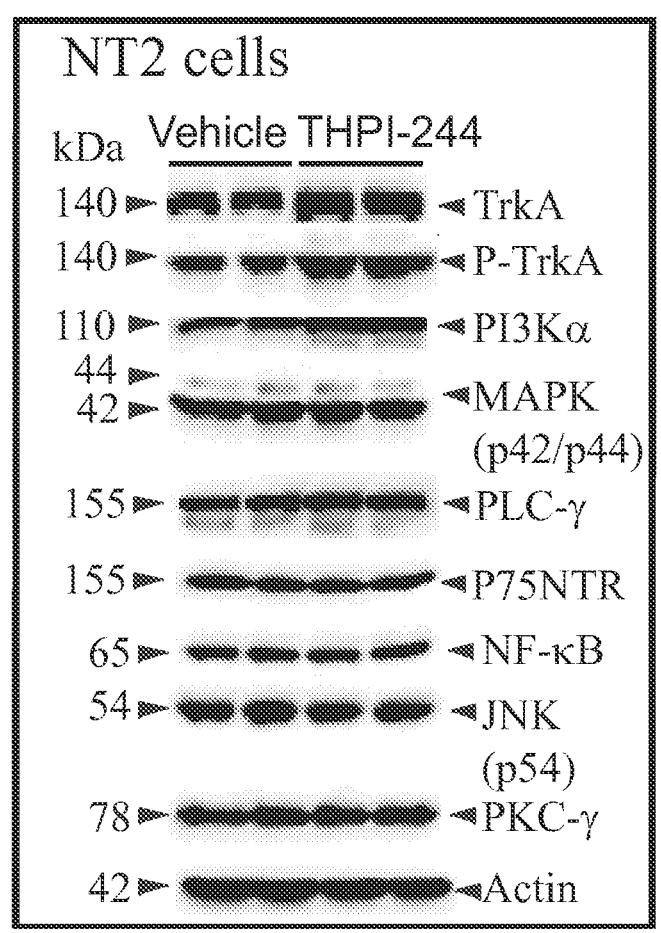
Fig. 1.9

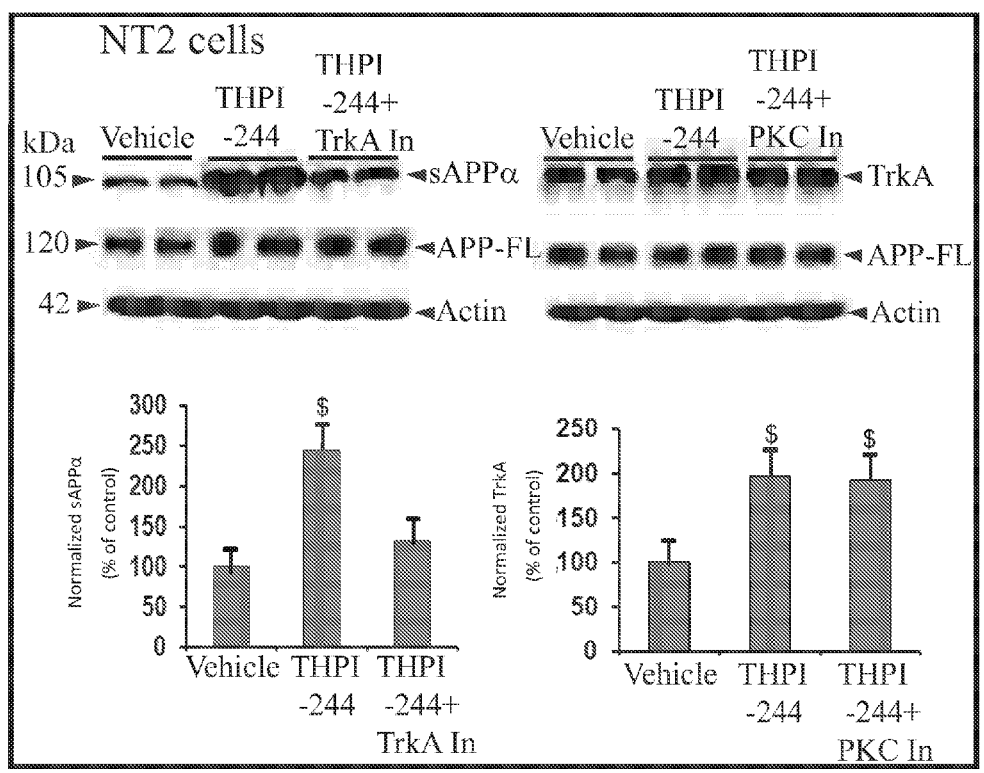
Fig. 1.10

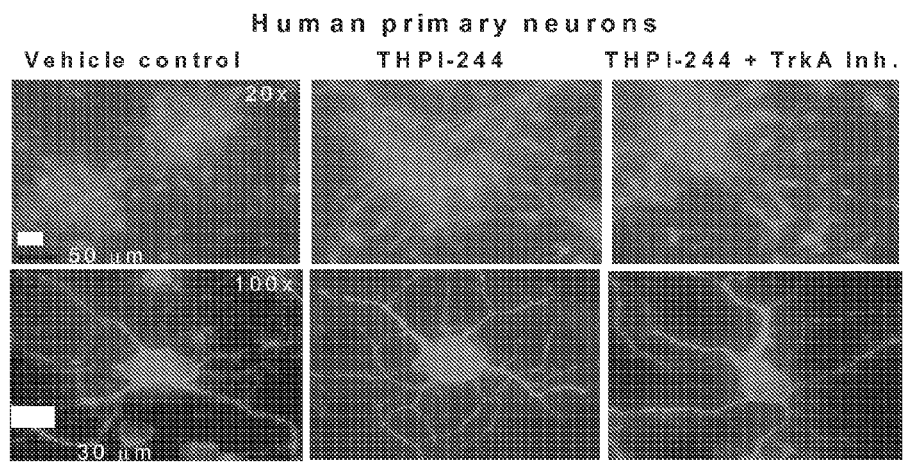
Fig. 1.11A
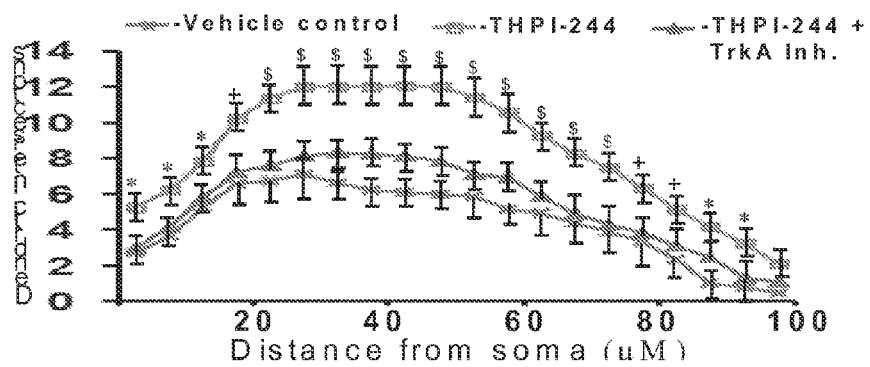
Fig. 1.11B

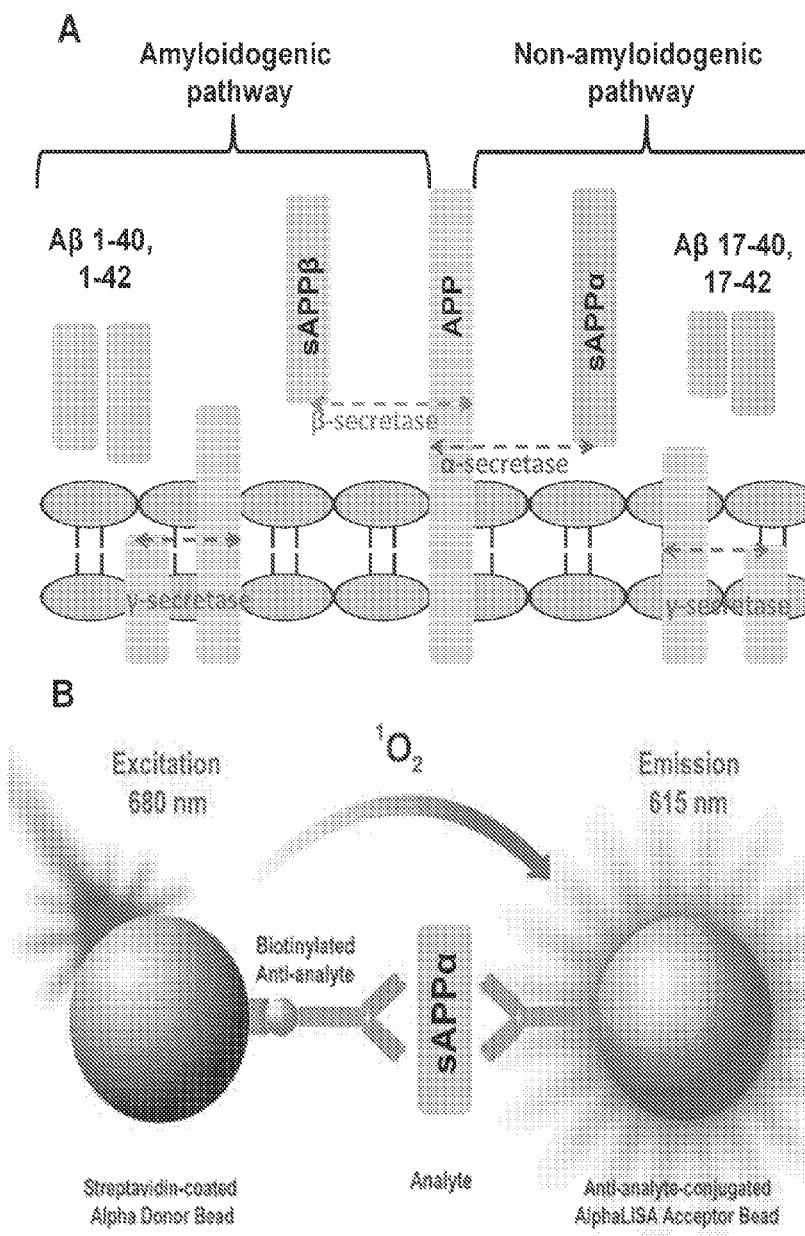
FIG. 2.1

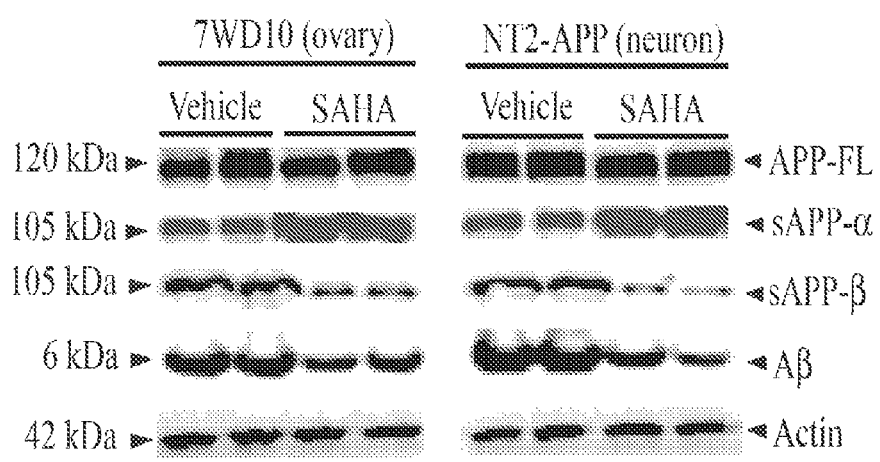
FIG. 2.2

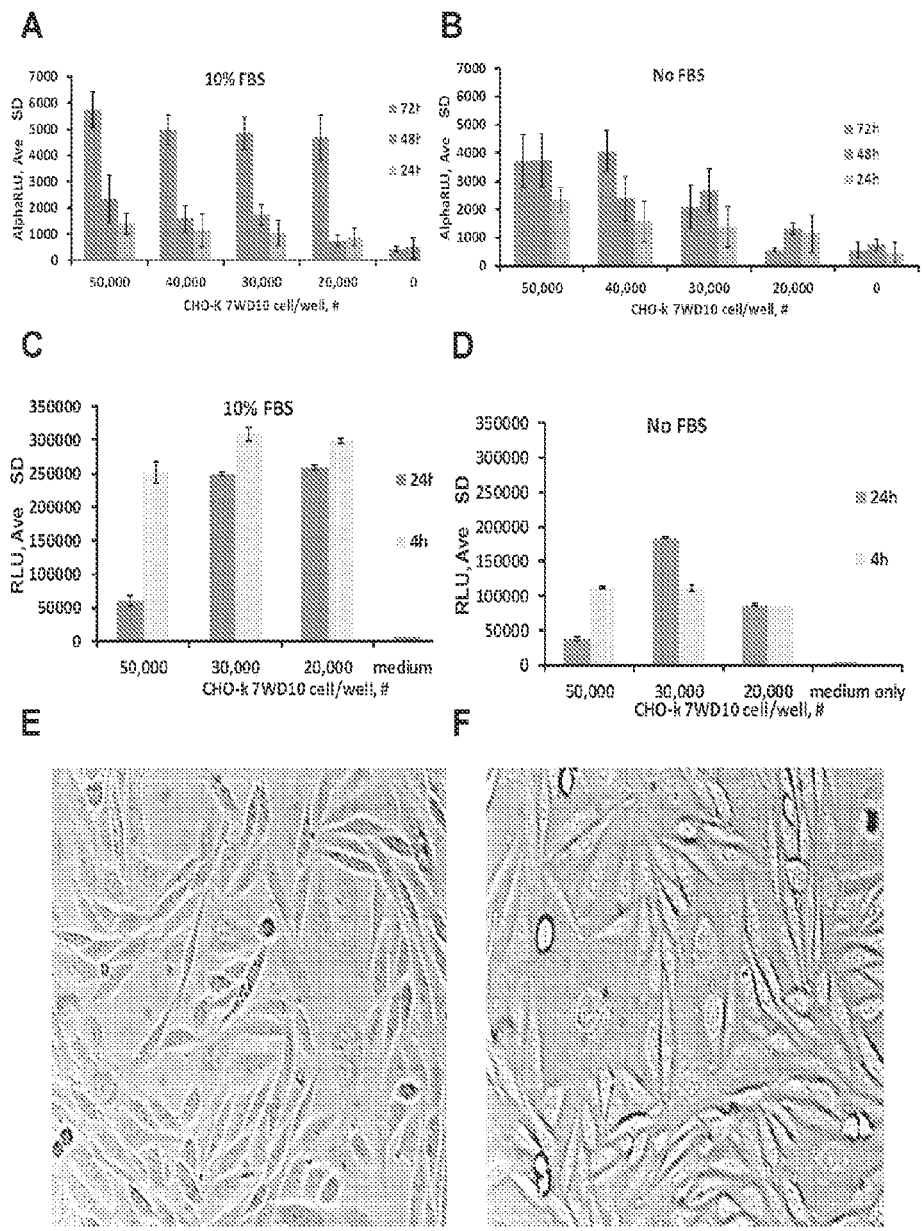
FIG. 2.3

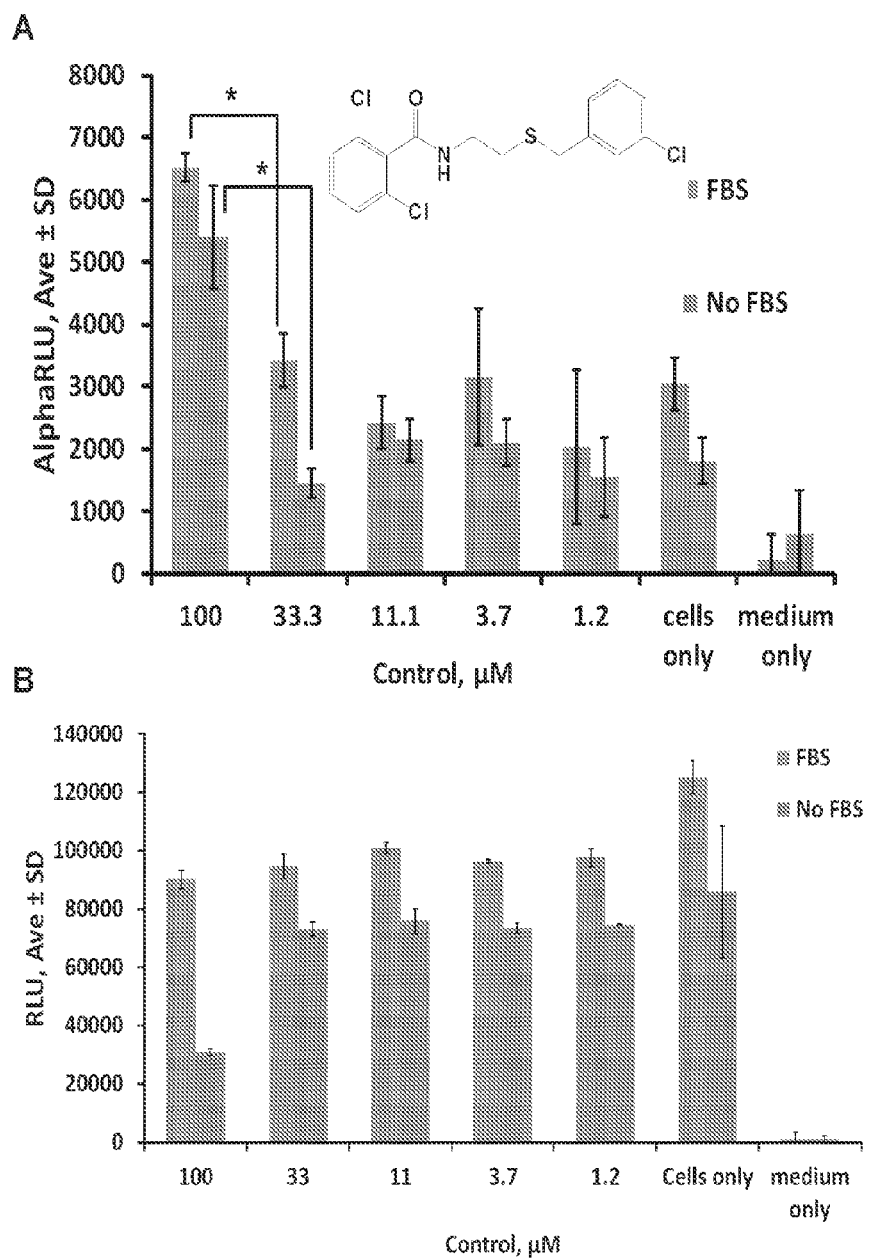
FIG. 2.4

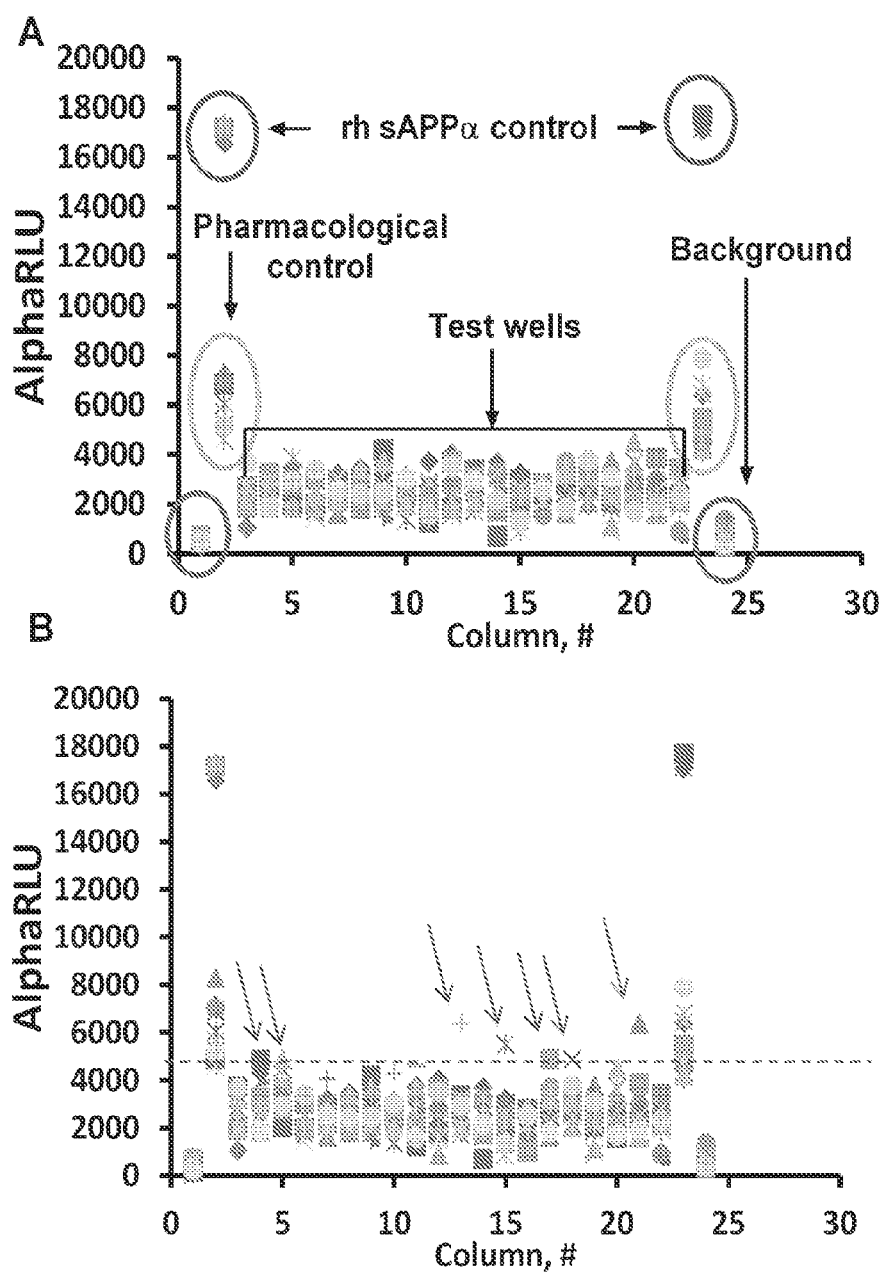
FIG. 2.5

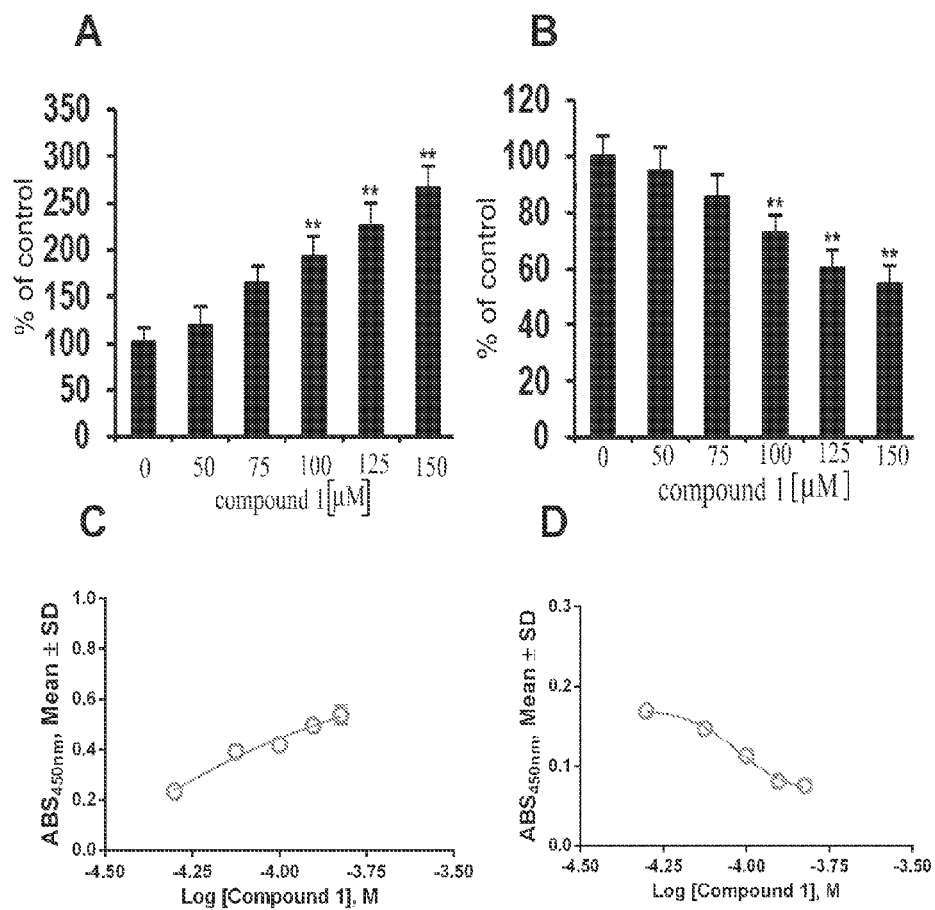
FIG. 2.6

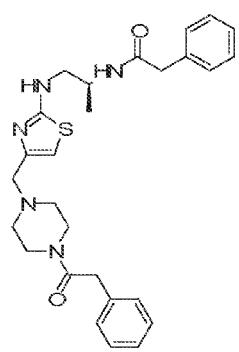
Molecular Weight: 491.65
2055-201
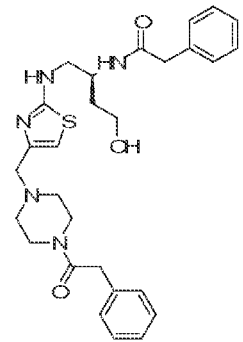
Molecular Weight: 521.67
2055-202
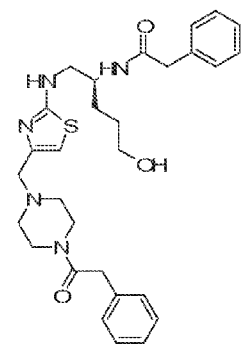
Molecular Weight: 535.70
2055-203
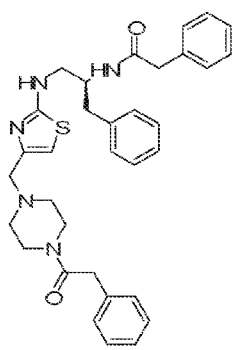
Molecular Weight: 567.74
2055-204
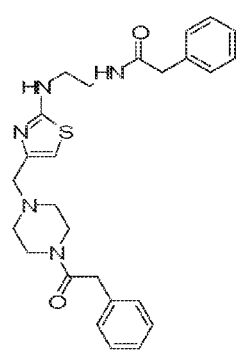
Molecular Weight: 477.62
2055-205
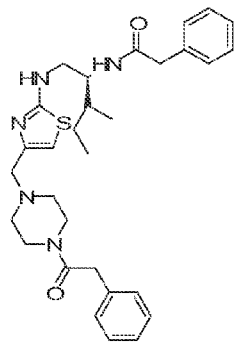
Molecular Weight: 533.73
2055-206
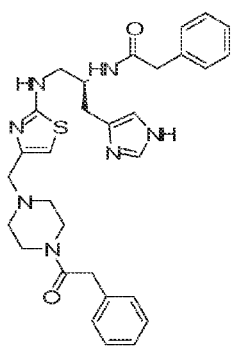
Molecular Weight: 557.71
2055-207
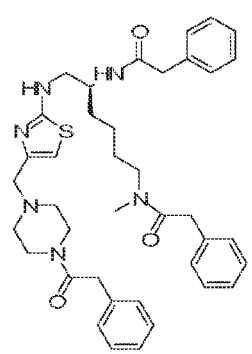
Molecular Weight: 680.90
2055-208
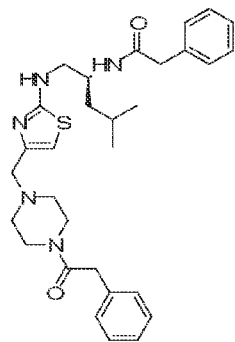
Molecular Weight: 533.73
2055-209
FIG. 3.1A

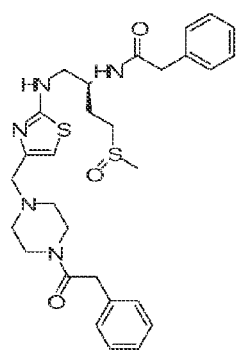
Molecular Weight: 567.77
2055-210
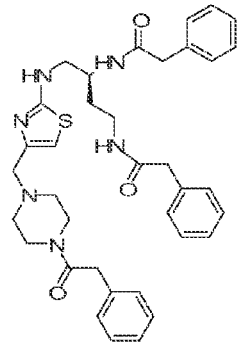
Molecular Weight: 638.82
2055-211
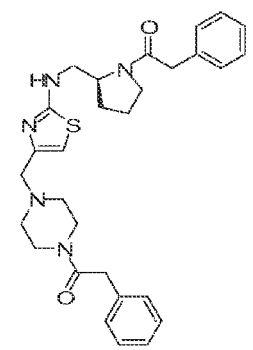
Molecular Weight: 517.69
2055-212
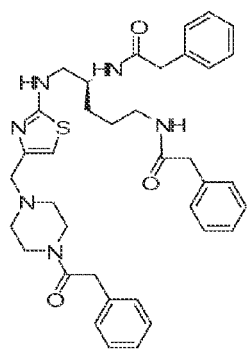
Molecular Weight: 652.85
2055-213
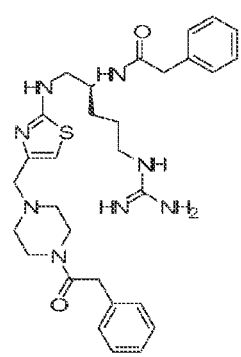
Molecular Weight: 576.76
2055-214
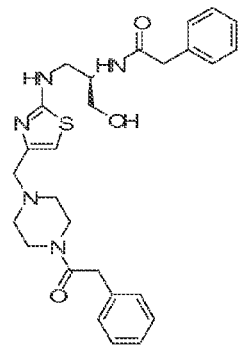
Molecular Weight: 507.65
2055-215
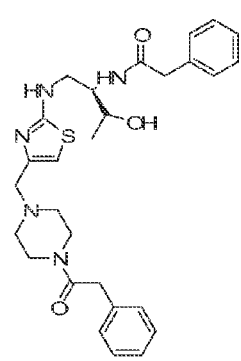
Molecular Weight: 521.67
2055-216
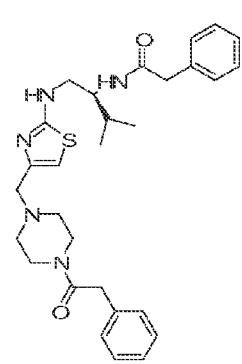
Molecular Weight: 519.70
2055-217
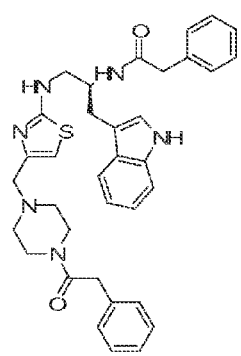
Molecular Weight: 606.78
2055-218
FIG. 3.1B

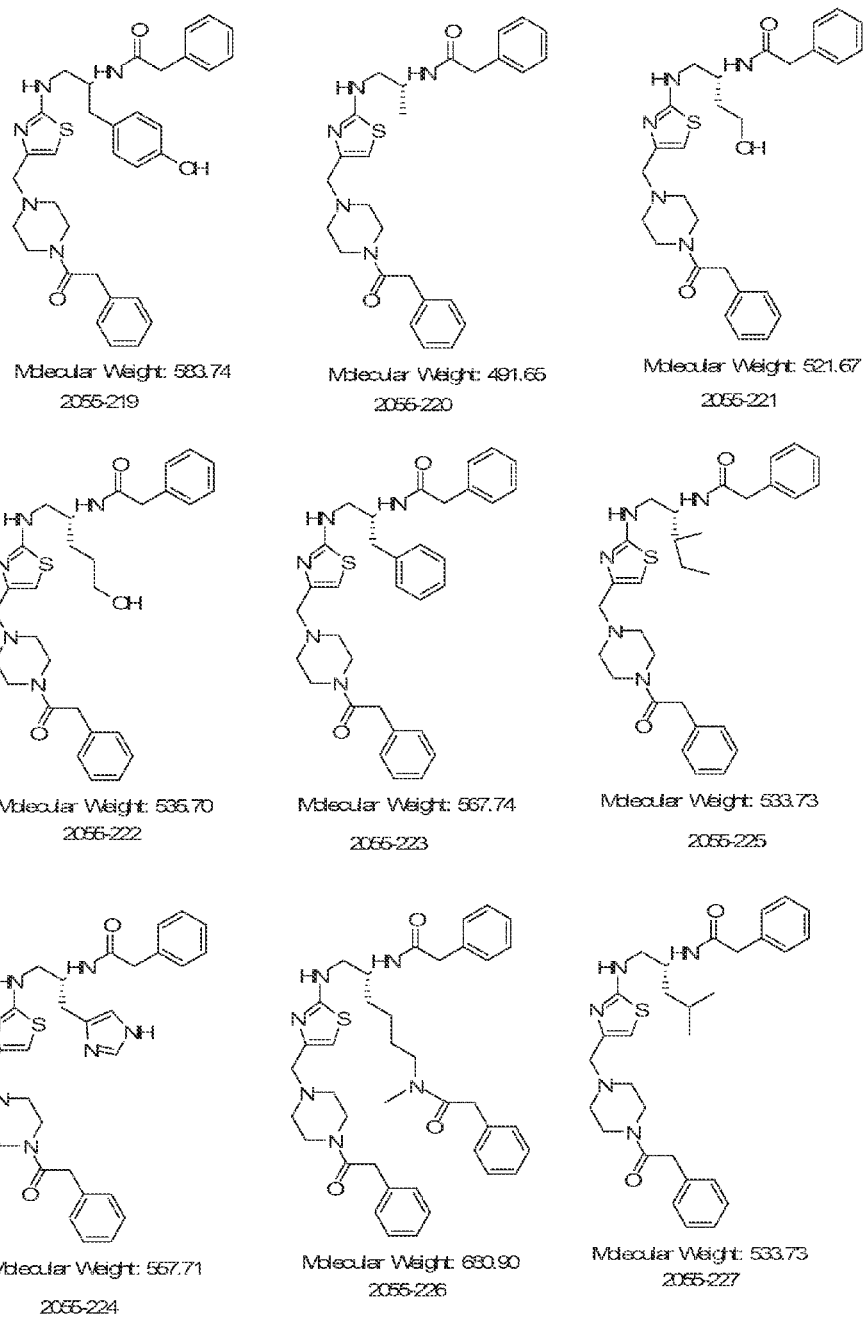
FIG. 3.1C

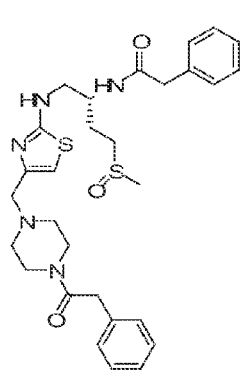
Molecular Weight: 567.77
2055-228
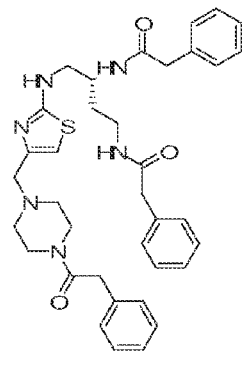
Molecular Weight: 638.82
2055-229
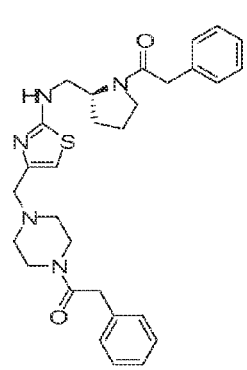
Molecular Weight: 517.69
2055-230
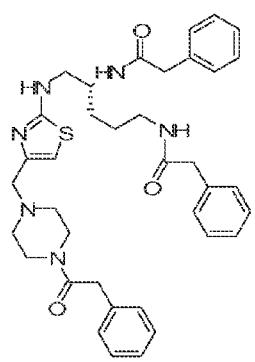
Molecular Weight: 652.85
2055-231
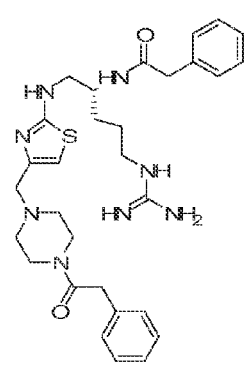
Molecular Weight: 576.76
2055-232
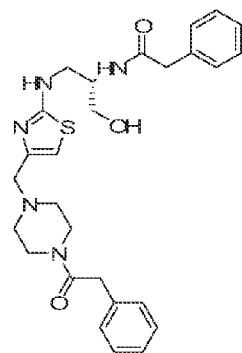
Molecular Weight: 507.65
2055-233
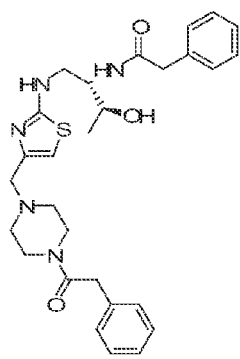
Molecular Weight: 521.67
2055-234
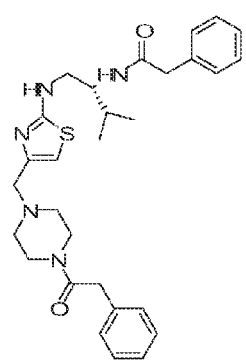
Molecular Weight: 519.70
2055-235
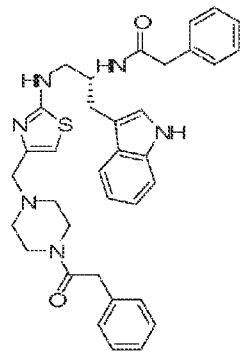
Molecular Weight: 606.78
2055-236
FIG. 3.1D

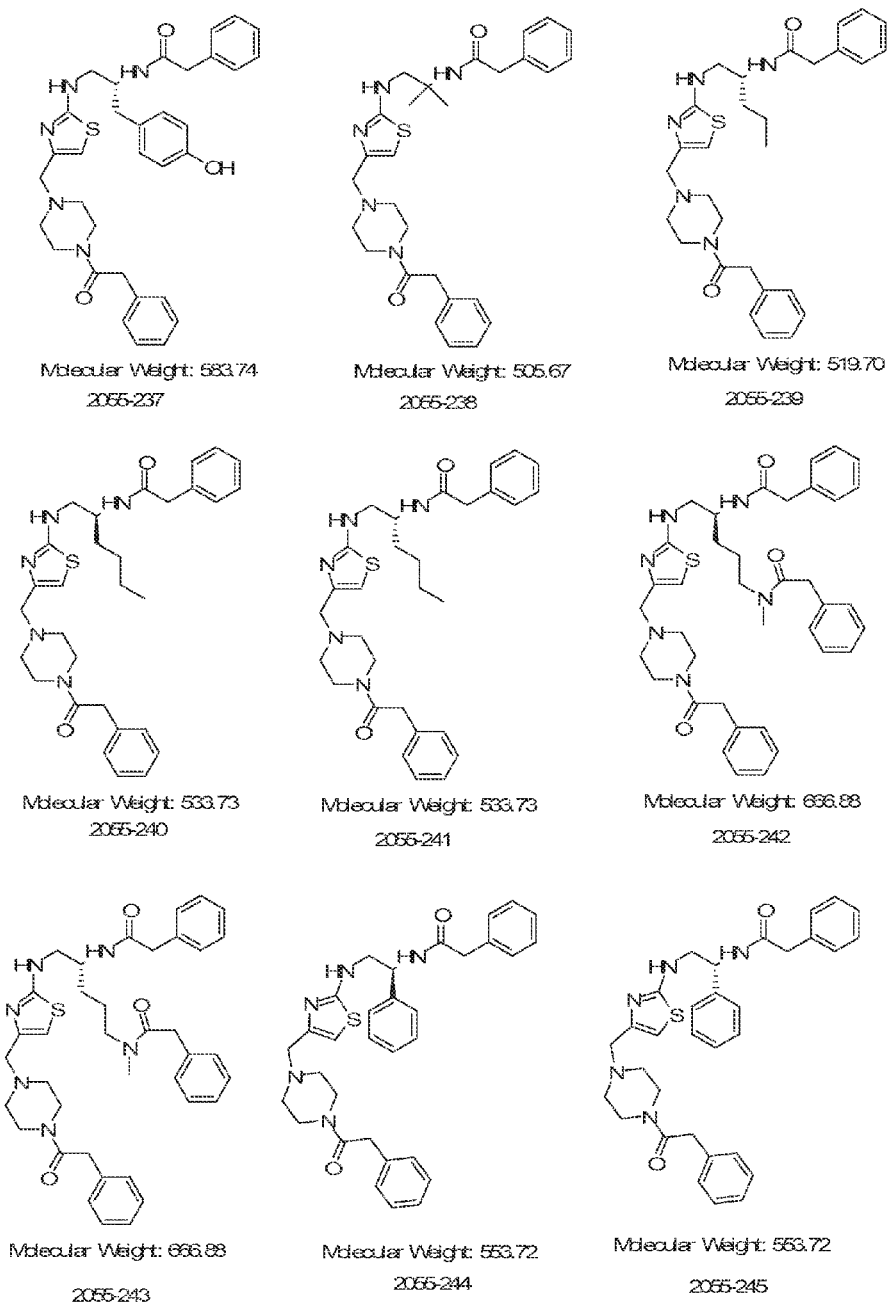
FIG. 3.1E

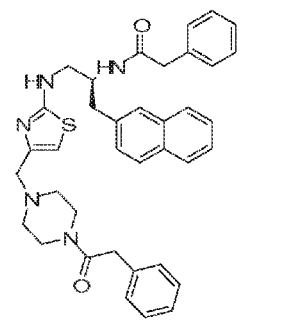
Molecular Weight: 617.80
2055-246
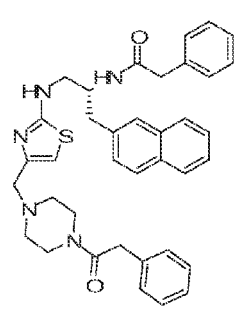
Molecular Weight: 617.80
2055-247
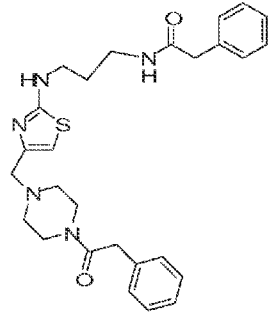
Molecular Weight: 491.65
2055-248
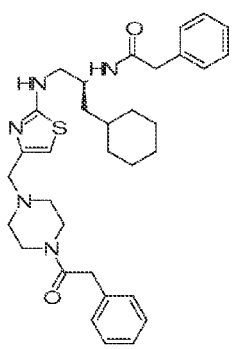
Molecular Weight: 573.79
2055-249
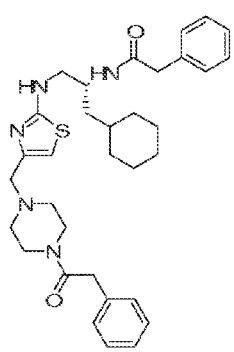
Molecular Weight: 573.79
2055-250
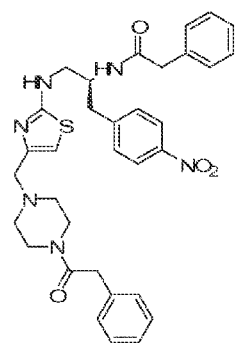
Molecular Weight: 612.74
2055-251
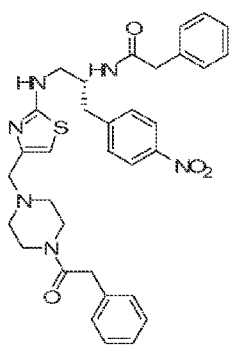
Molecular Weight: 612.74
2055-252
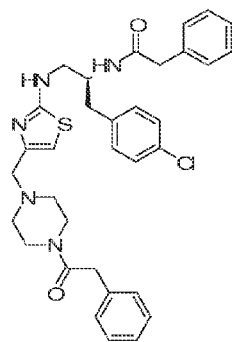
Molecular Weight: 602.19
2055-253
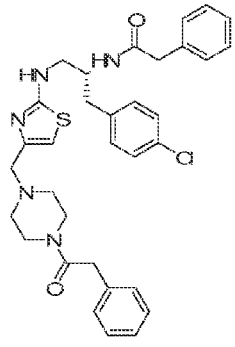
Molecular Weight: 602.19
2055-254
FIG. 3.1F

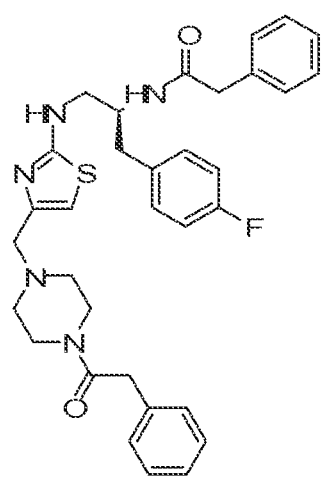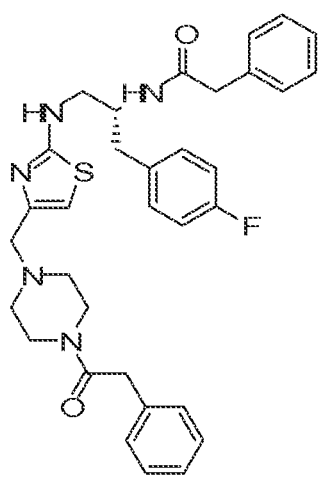
Molecular Weight: 585.73
2055-255
Molecular Weight: 585.73
2055-256
FIG. 3.1G

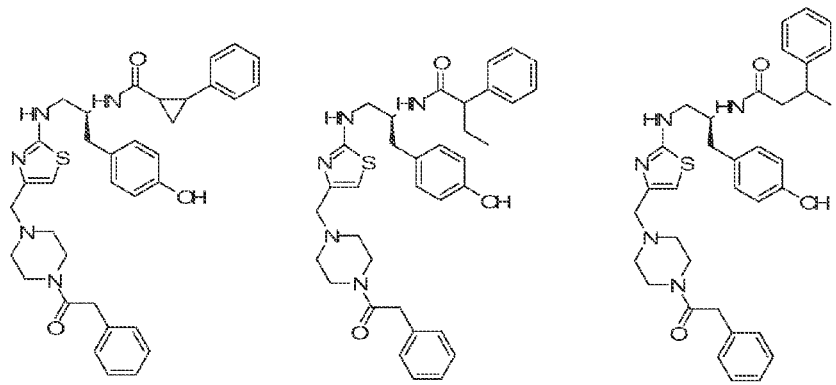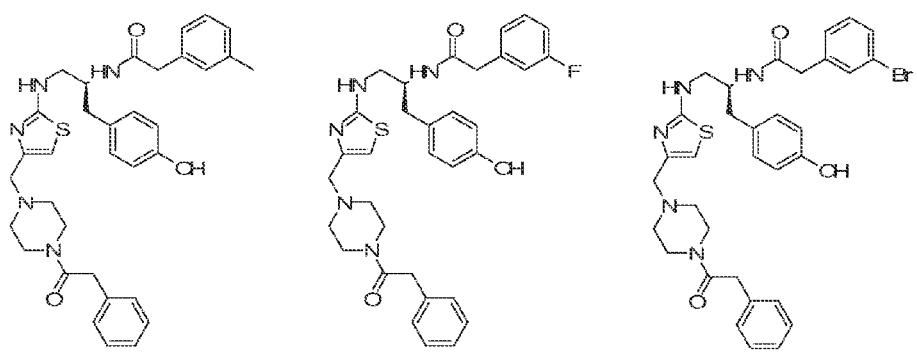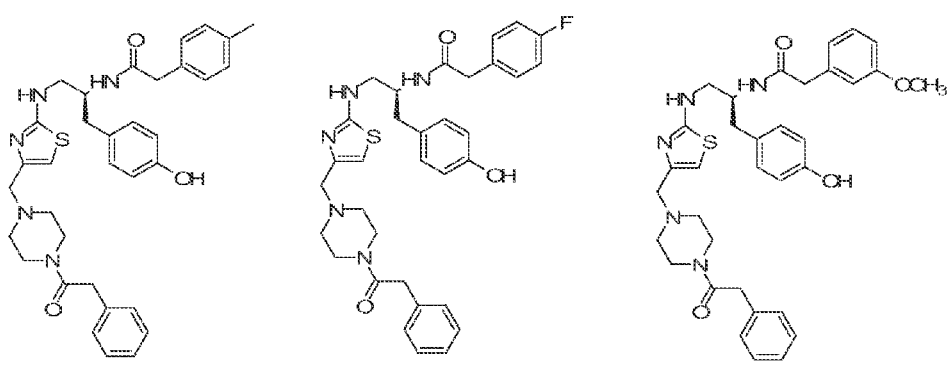
FIG. 3.1H

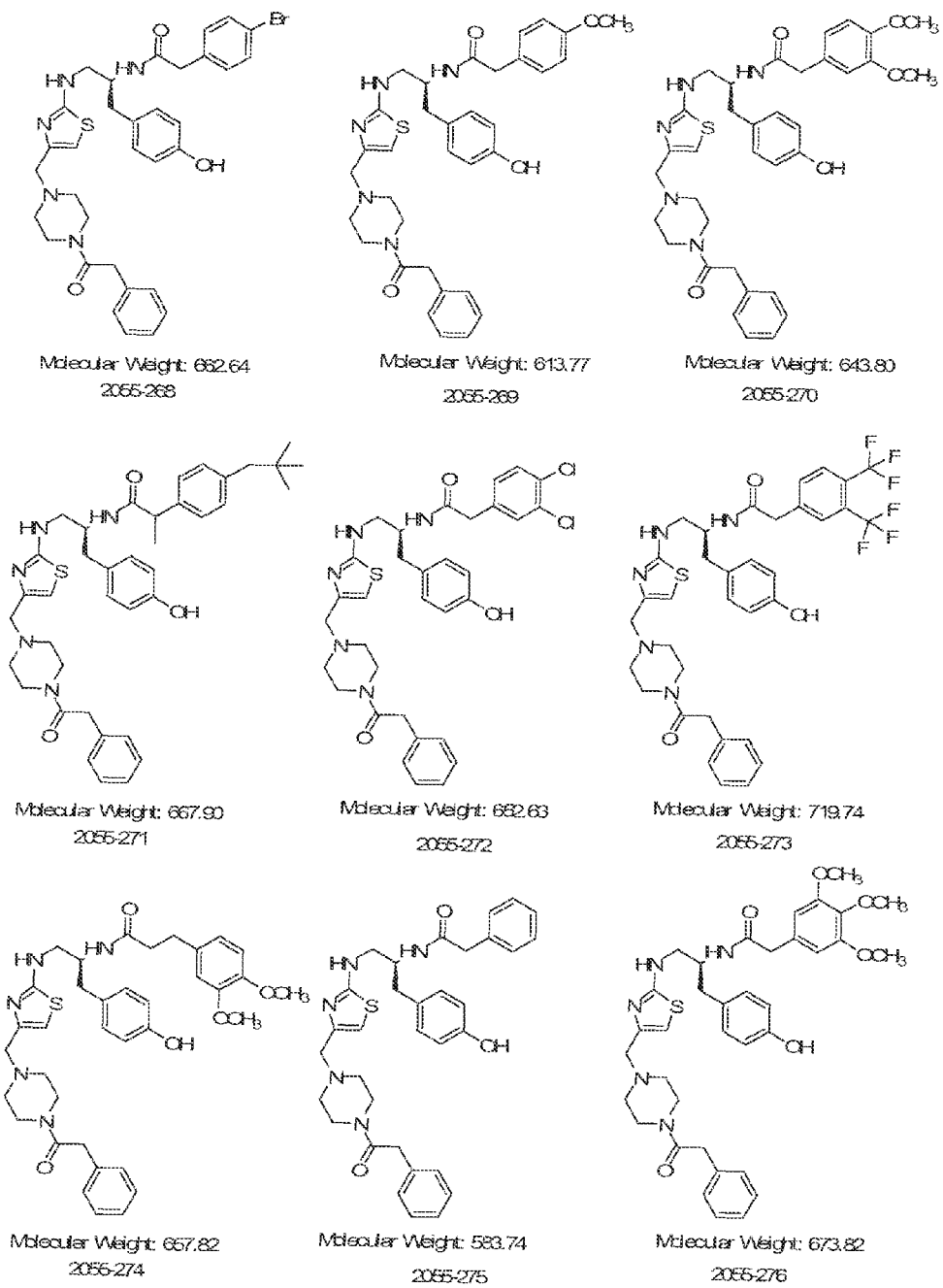
FIG. 3.1I

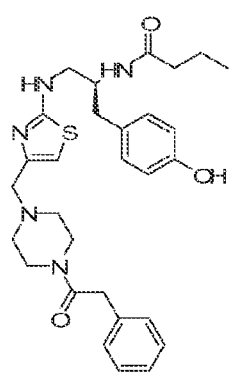
Molecular Weight: 535.70
2055-277
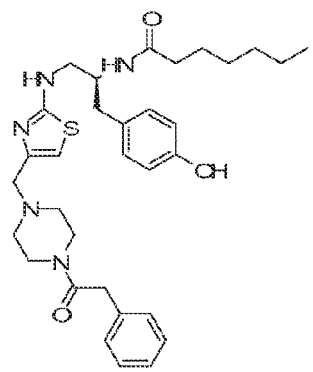
Molecular Weight: 577.78
2055-278
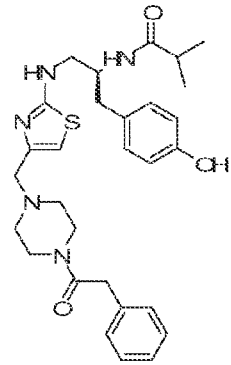
Molecular Weight: 535.70
2055-279
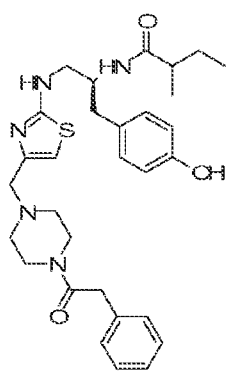
Molecular Weight: 549.73
2055-280
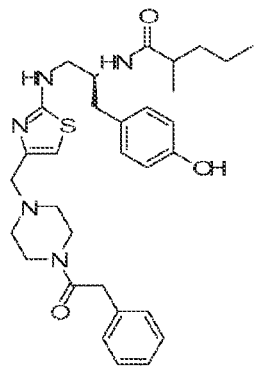
Molecular Weight: 563.75
2055-281
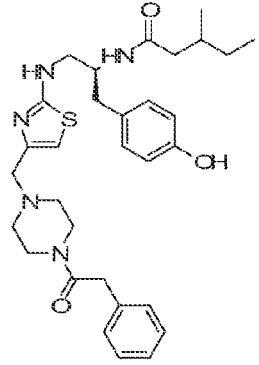
Molecular Weight: 563.75
2055-282
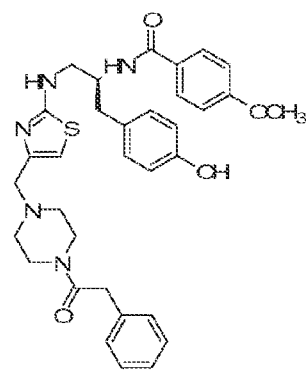
Molecular Weight: 599.74
2055-283
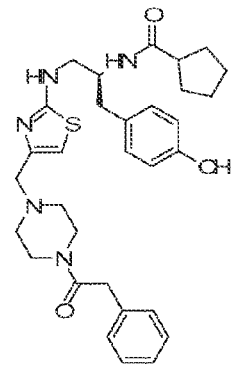
Molecular Weight: 561.74
2055-284
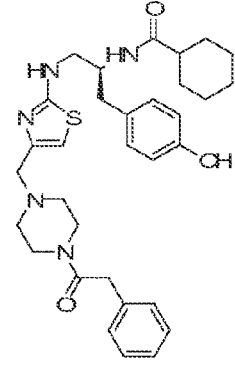
Molecular Weight: 575.76
2055-285
FIG. 3.1J

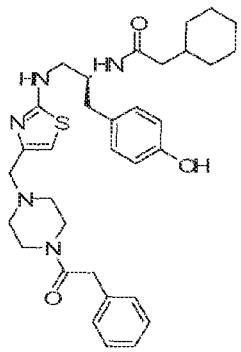
Molecular Weight: 589.79
2055-286
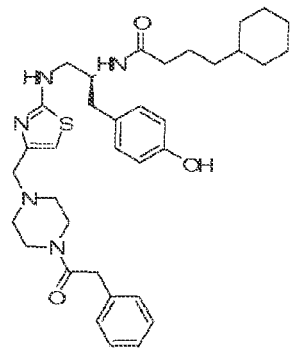
Molecular Weight: 617.84
2055-287
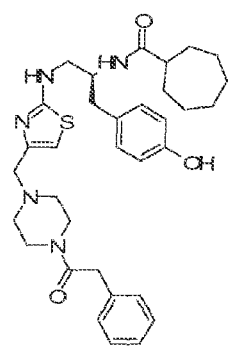
Molecular Weight: 589.79
2055-288
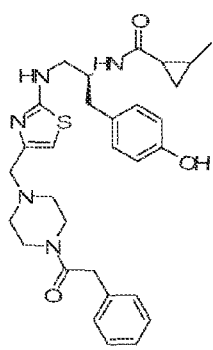
Molecular Weight: 547.71
2055-289
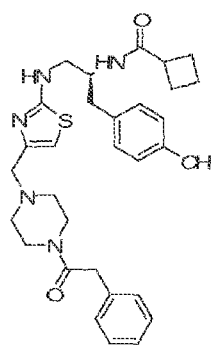
Molecular Weight: 547.71
2055-290
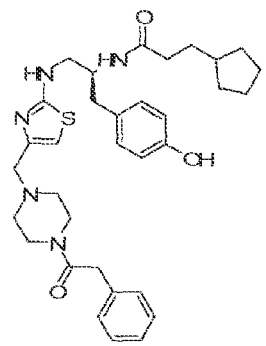
Molecular Weight: 589.79
2055-291
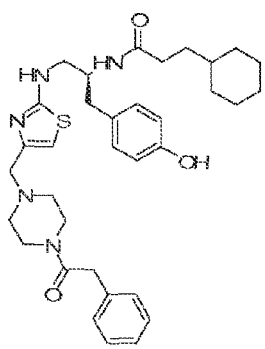
Molecular Weight: 603.82
2055-292
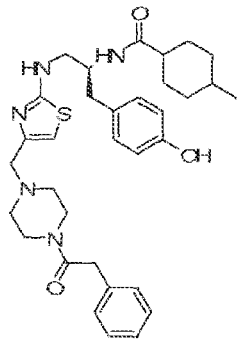
Molecular Weight: 589.79
2055-293
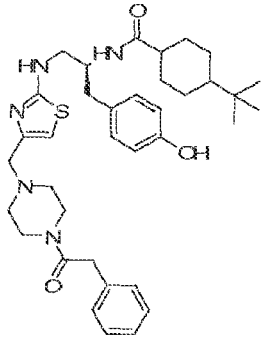
Molecular Weight: 631.87
2055-294
FIG. 3.1K

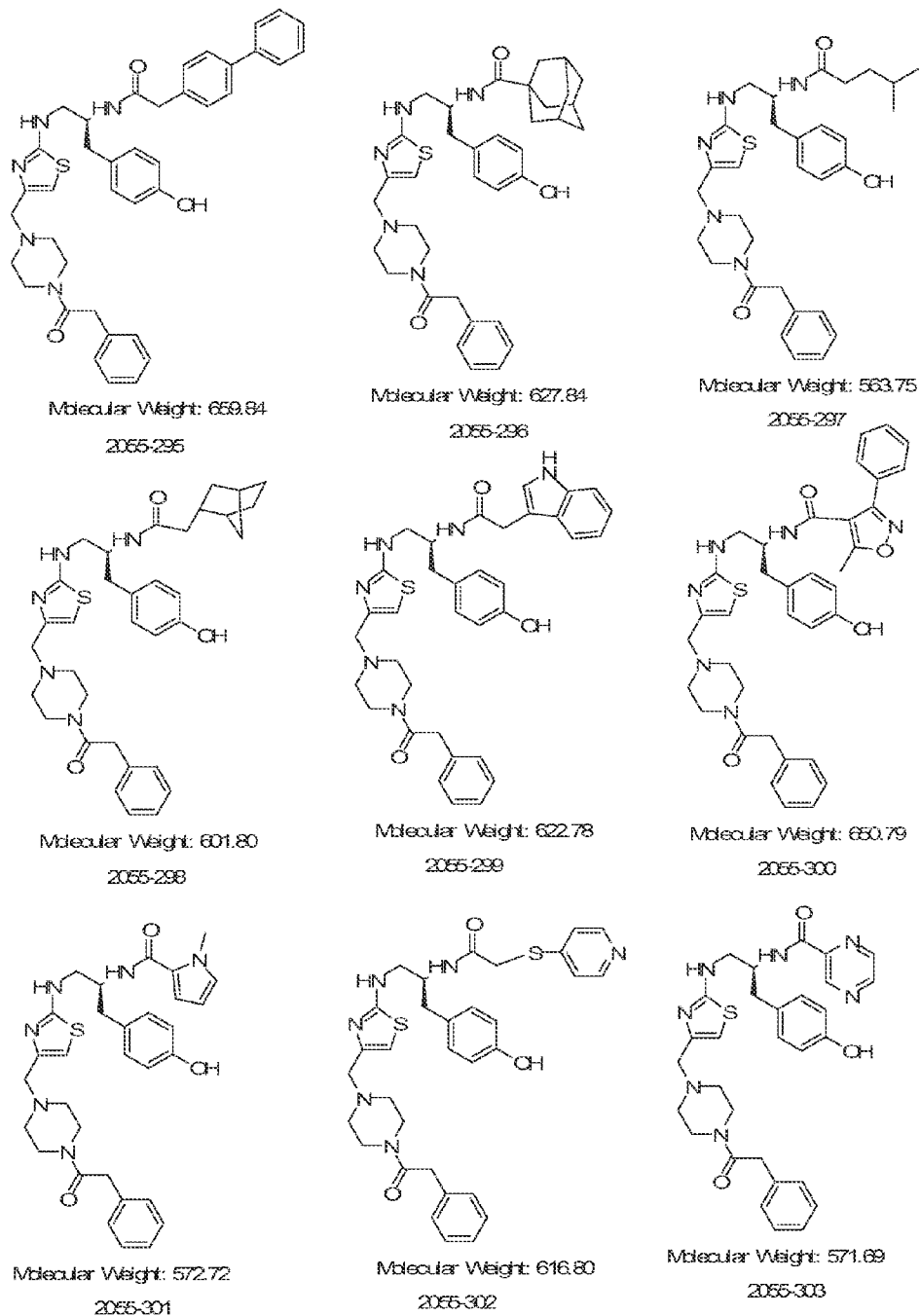
FIG. 3.1L

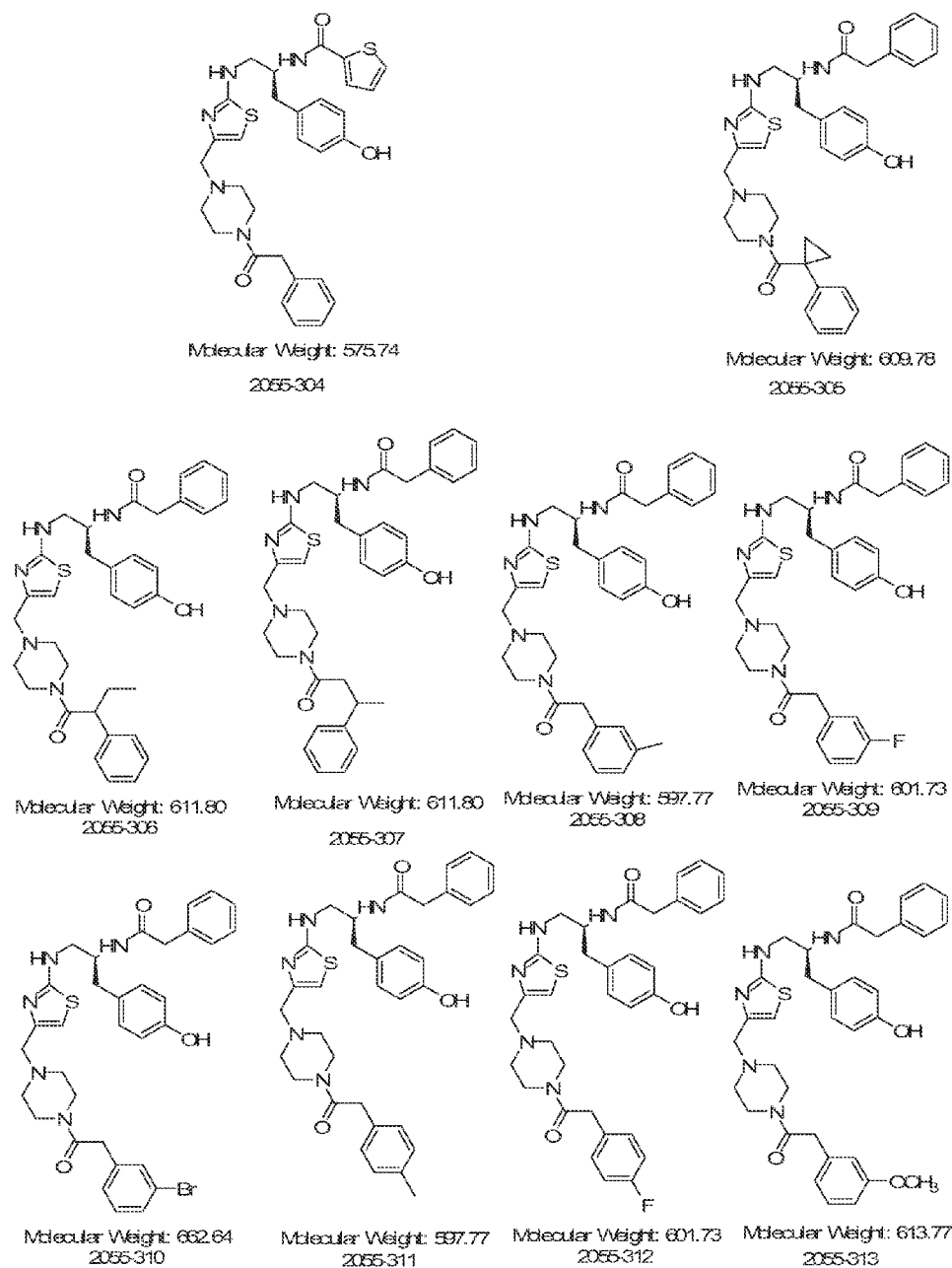
FIG. 3.1M

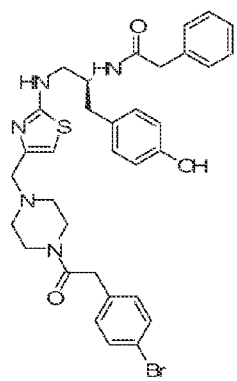
Molecular Weight: 662.64
2055-314
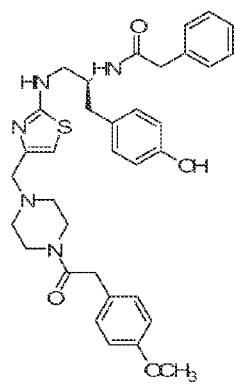
Molecular Weight: 613.77
2055-315
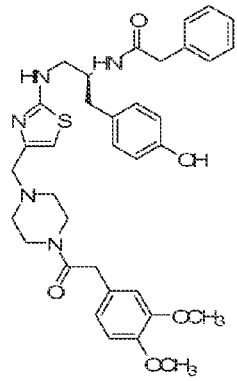
Molecular Weight: 643.80
2055-316
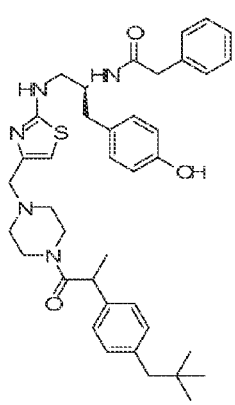
Molecular Weight: 667.90
2055-317
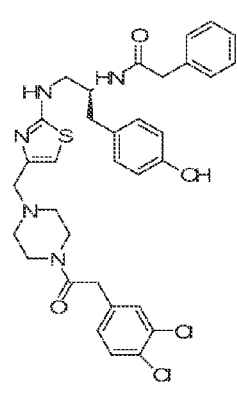
Molecular Weight: 652.63
2055-318
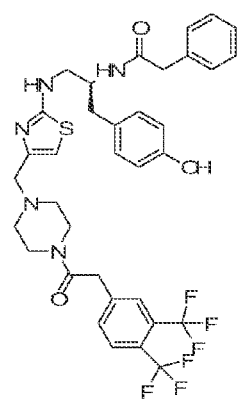
Molecular Weight: 719.74
2055-319
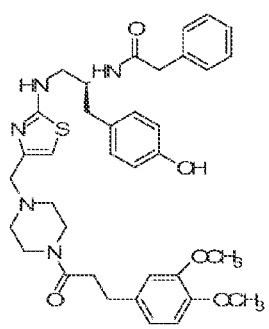
Molecular Weight: 657.82
2055-320
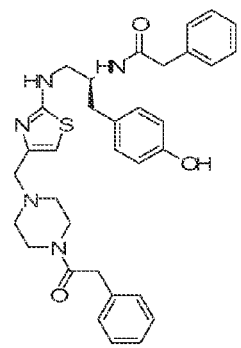
Molecular Weight: 583.74
2055-321
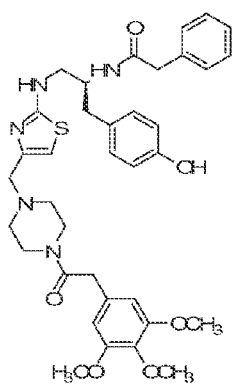
Molecular Weight: 673.82
2055-322
FIG. 3.1N

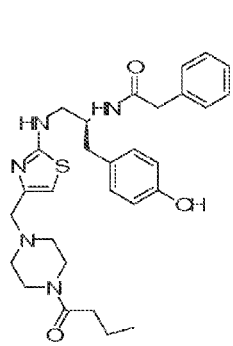
Molecular Weight: 535.70
2055-323
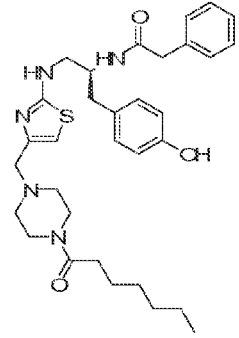
Molecular Weight: 577.78
2055-324
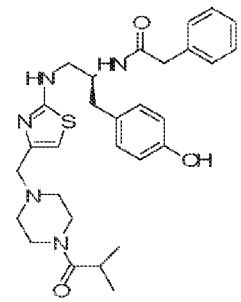
Molecular Weight: 535.70
2055-325
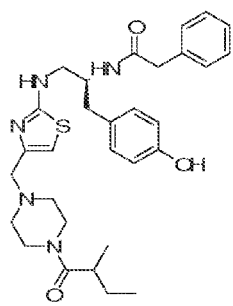
Molecular Weight: 549.73
2055-326
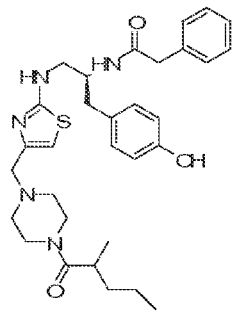
Molecular Weight: 563.75
2055-327
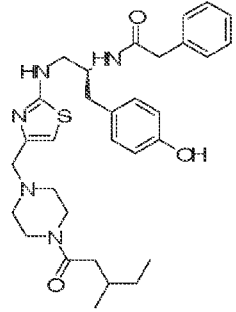
Molecular Weight: 563.75
2055-328
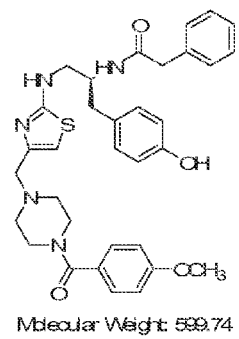
Molecular Weight: 599.74
2055-329
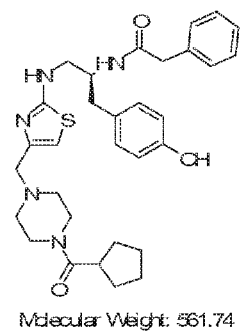
Molecular Weight: 561.74
2055-330
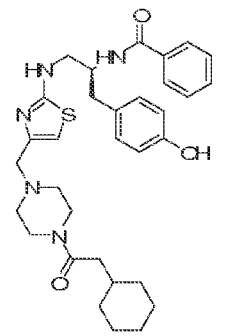
Molecular Weight: 575.76
2055-331
FIG. 3.1O

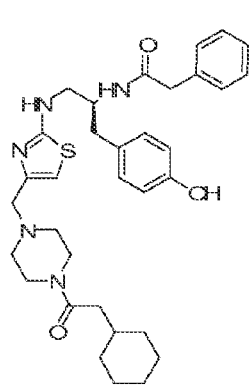
Molecular Weight: 589.79
2055-332
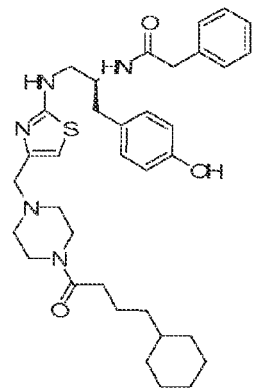
Molecular Weight: 617.84
2055-333
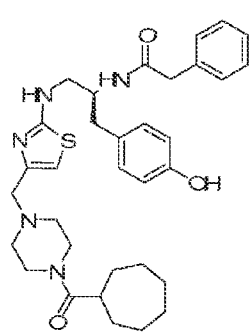
Molecular Weight: 589.79
2055-334
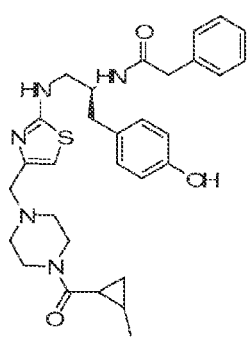
Molecular Weight: 547.71
2055-335
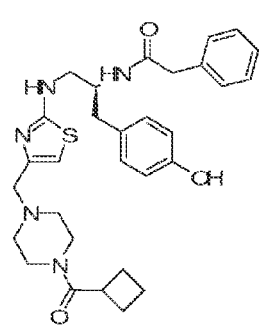
Molecular Weight: 547.71
2055-336
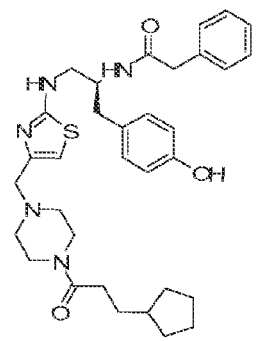
Molecular Weight: 589.79
2055-337
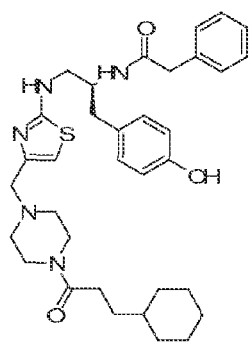
Molecular Weight: 603.82
2055-338
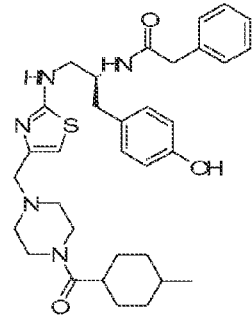
Molecular Weight: 589.79
2055-339
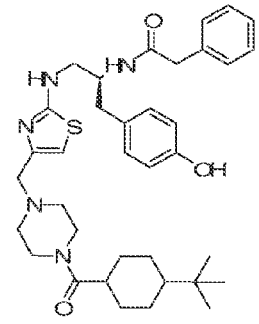
Molecular Weight: 631.87
2055-340
FIG. 3.1P

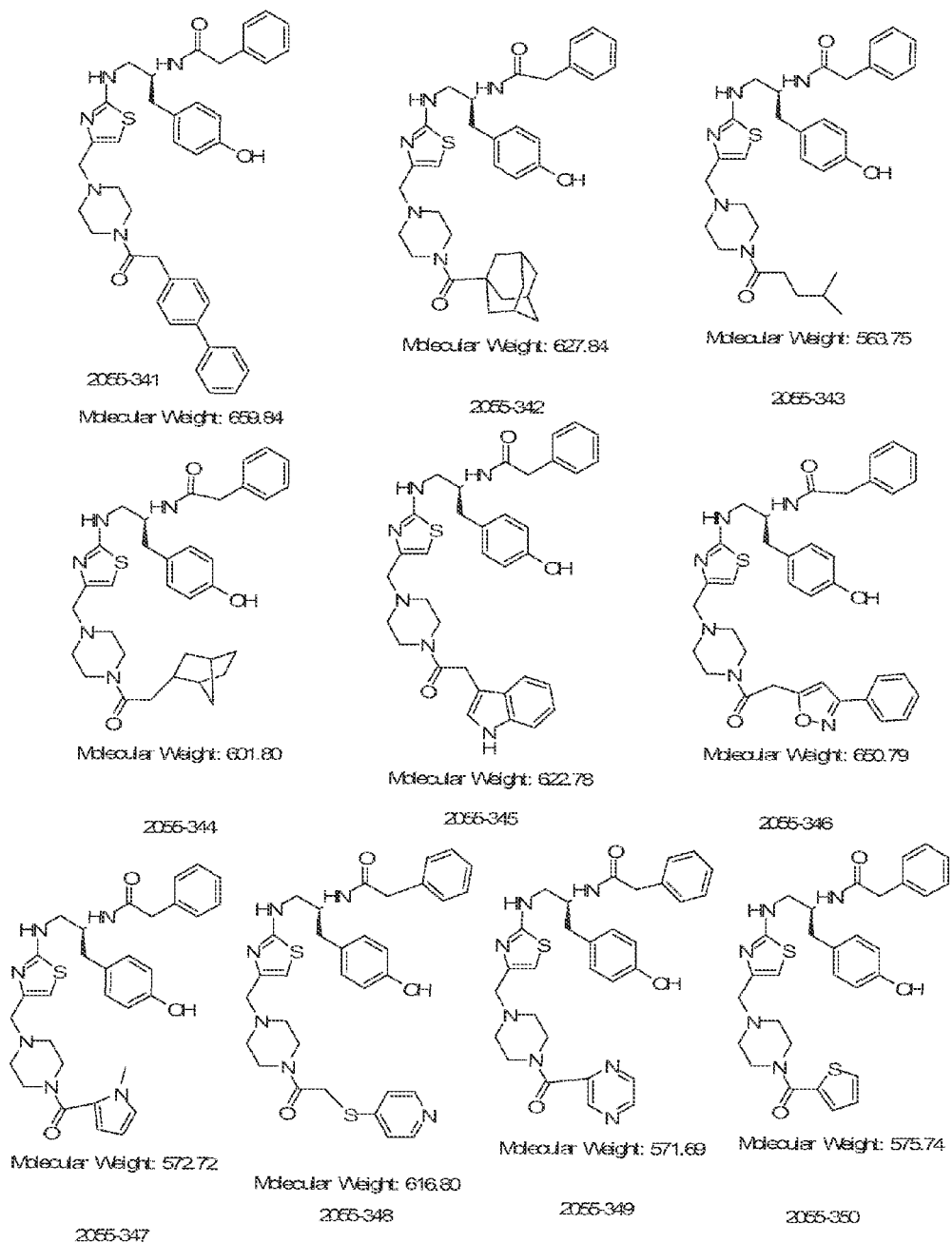
FIG. 3.1Q

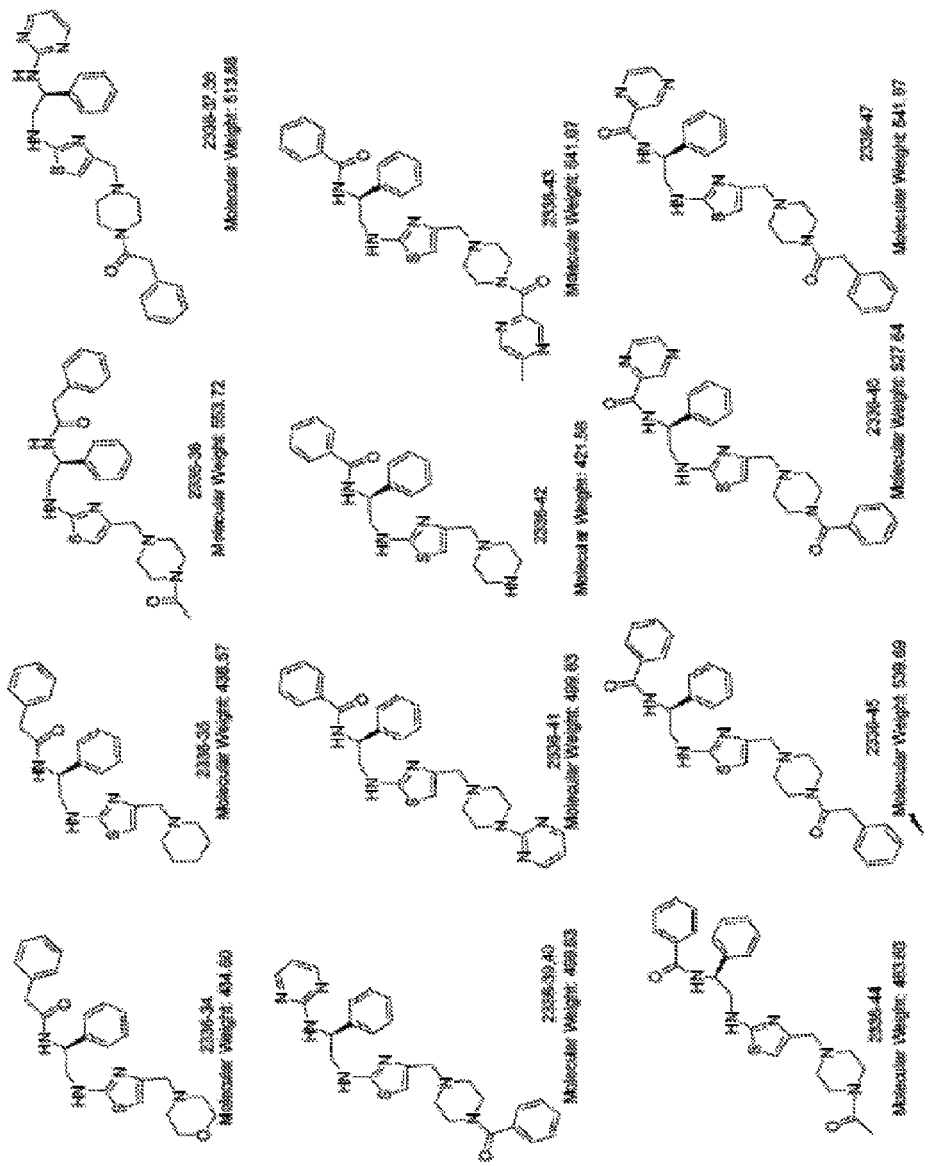
FIG. 4.1A

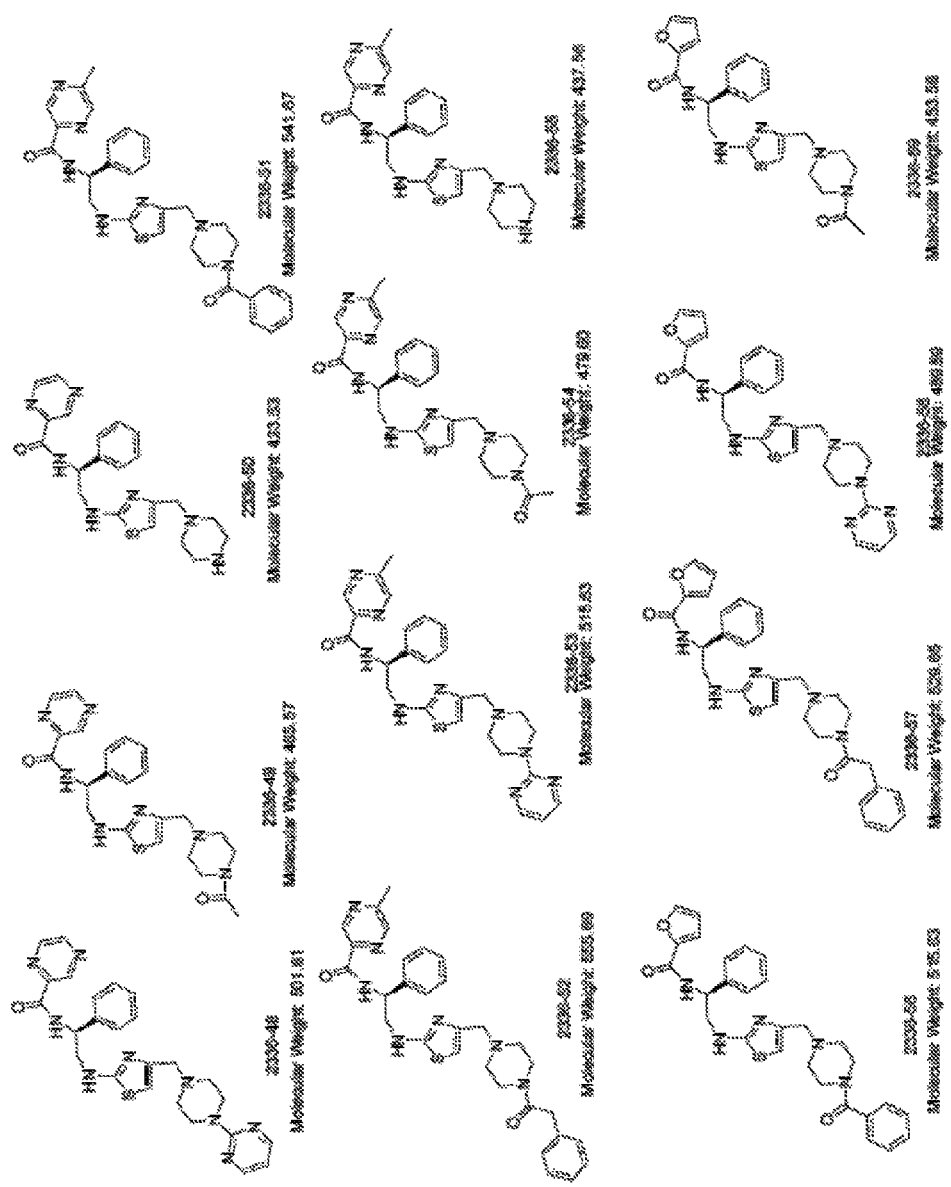
FIG. 4.1B

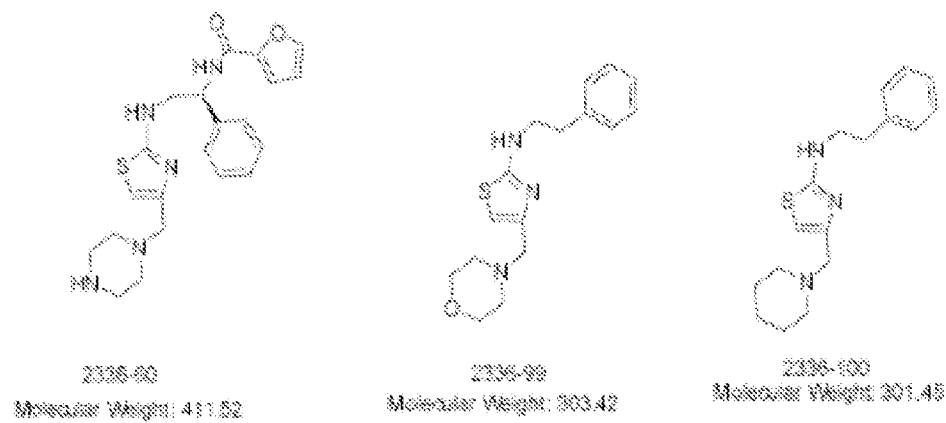
FIG. 4.1C

| Analogs of TPI2055-244 (THPI-244)* | | | | |
|---|---|---|---|---|
| TPI | R1 | R2 | R3 | MW |
| 2336-34 | S-phenyl | phenyl methyl | treated with morpholine | 434.6 |
| 2336-35 | S-phenyl | phenyl methyl | treated with piperidine | 436.57 |
| 2336-36 | S-phenyl | phenyl methyl | Acetic anhydride | 553.72 |
| 2336-37 | S-phenyl | pyrimidine | Phenylacetic acid | 513.66 |
| 2336-39 | S-phenyl | pyrimidine | Benzoic acid | 499.63 |
| 2336-40 | S-phenyl | pyrimidine | Benzoic acid | 499.63 |
| 2336-41 | S-phenyl | phenyl ethyl | Chloropyrimidine | 500 |
| 2336-42 | S-phenyl | benzoic acid | H | 422 |
| 2336-43 | S-phenyl | benzoic acid | 5-methylpyrazine-2-car | 421 |
| 2336-44 | S-phenyl | benzoic acid | acetic anhydride | 464 |
| 2336-45 | S-phenyl | benzoic acid | Phenylacetic acid | 539.69 |
| 2336-46 | S-phenyl | 2-pyrazine | Benzoic acid | 527.64 |
| 2336-47 | S-phenyl | 2-pyrazine | Phenylacetic acid | 541.67 |
| 2336-48 | S-phenyl | 2-pyrazine | Chloropyrimidine | 501.61 |
| 2336-49 | S-phenyl | 2-pyrazine | Acetic anhydride | 465.57 |
| 2336-50 | S-phenyl | 2-pyrazine | H | 424 |
| 2336-51 | S-phenyl | 5-methyl-2-pyrazine | Benzoic acid | 541.67 |
| 2336-52 | S-phenyl | 5-methyl-2-pyrazine | Phenylacetic acid | 555.69 |
| 2336-53 | S-phenyl | 5-methyl-2-pyrazine | Chloropyrimidine | 515.63 |
| 2336-54 | S-phenyl | 5-methyl-2-pyrazine | Acetic anhydride | 480 |
| 2336-55 | S-phenyl | 5-methyl-2-pyrazine | H | 438 |
| 2336-56 | S-phenyl | 2-furane | Benzoic acid | 515.63 |
| 2336-57 | S-phenyl | 2-furane | Phenylacetic acid | 529.65 |
| 2336-58 | S-phenyl | 2-furane | Chloropyrimidine | 489.59 |
| 2336-59 | S-phenyl | 2-furane | Acetic anhydride | 454 |
| 2336-60 | S-phenyl | 2-furane | H | 412 |
| 2336-99 | Phenyl Acetic acid | NA | NA | 303.42 |
| 2336-100 | Phenyl Acetic acid | NA | NA | 301.45 |

FIG. 5.1

| TPI | R1 | R2 | R3 | MW |
|---|---|---|---|---|
| 2336-34 | Boc-Phg-OH | phenyl acetic acid | treated with morpholine | NA | 434.6 |
| 2336-35 | Boc-Phg-OH | phenyl acetic acid | treated with piperidine | NA | 436.57 |
| 2336-36 | Boc-Phg-OH | phenyl acetic acid | piperazine | Acetic anhydride | 553.72 |
| 2336-37 | Boc-Phg-OH | 2-chloropyrimidine | piperazine | Phenylacetic acid | 513.66 |
| 2336-39 | Boc-Phg-OH | 2-chloropyrimidine | piperazine | Benzoic acid | 499.63 |
| 2336-40 | Boc-Phg-OH | 2-chloropyrimidine | piperazine | Benzoic acid | 499.63 |
| 2336-41 | Boc-Phg-OH | benzoic acid | piperazine | Chloropyrimidine | 500 |
| 2336-42 | Boc-Phg-OH | benzoic acid | piperazine | H | 422 |
| 2336-43 | Boc-Phg-OH | benzoic acid | piperazine | 5-methylpyrazine-2-carbo | 421 |
| 2336-44 | Boc-Phg-OH | benzoic acid | piperazine | acetic anhydride | 464 |
| 2336-45 | Boc-Phg-OH | benzoic acid | piperazine | Phenylacetic acid | 539.69 |
| 2336-46 | Boc-Phg-OH | 2-pyrazine carboxylic acid | piperazine | Benzoic acid | 527.64 |
| 2336-47 | Boc-Phg-OH | 2-pyrazine carboxylic acid | piperazine | Phenylacetic acid | 541.67 |
| 2336-48 | Boc-Phg-OH | 2-pyrazine carboxylic acid | piperazine | Chloropyrimidine | 501.61 |
| 2336-49 | Boc-Phg-OH | 2-pyrazine carboxylic acid | piperazine | Acetic anhydride | 465.57 |
| 2336-50 | Boc-Phg-OH | 2-pyrazine carboxylic acid | piperazine | H | 424 |
| 2336-51 | Boc-Phg-OH | 5-methyl-2-pyrazine carboxylic acid | piperazine | Benzoic acid | 541.67 |
| 2336-52 | Boc-Phg-OH | 5-methyl-2-pyrazine carboxylic acid | piperazine | Phenylacetic acid | 555.69 |
| 2336-53 | Boc-Phg-OH | 5-methyl-2-pyrazine carboxylic acid | piperazine | Chloropyrimidine | 515.63 |
| 2336-54 | Boc-Phg-OH | 5-methyl-2-pyrazine carboxylic acid | piperazine | Acetic anhydride | 480 |
| 2336-55 | Boc-Phg-OH | 5-methyl-2-pyrazine carboxylic acid | piperazine | H | 438 |
| 2336-56 | Boc-Phg-OH | 2-furoic acid | piperazine | Benzoic acid | 515.63 |
| 2336-57 | Boc-Phg-OH | 2-furoic acid | piperazine | Phenylacetic acid | 529.65 |
| 2336-58 | Boc-Phg-OH | 2-furoic acid | piperazine | Chloropyrimidine | 489.59 |
| 2336-59 | Boc-Phg-OH | 2-furoic acid | piperazine | Acetic anhydride | 454 |
| 2336-60 | Boc-Phg-OH | 2-furoic acid | piperazine | H | 412 |
| 2336-99 | Phenyl Acetic acid | NA | treated with morpholine | NA | 303.42 |
| 2336-100 | Phenyl Acetic acid | NA | treated with piperidine | NA | 301.45 |

FIG. 6.1

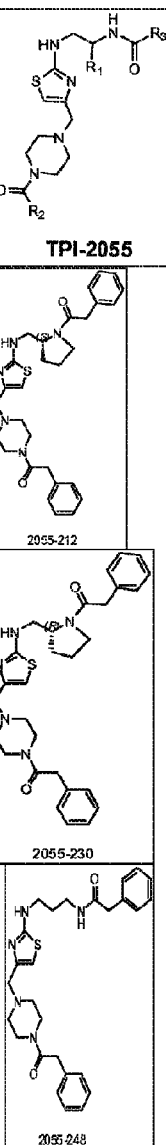

| Controls | R1 | R2 | R3 | MW |
|---|---|---|---|---|
| 2055-201 | Boc-L-Ala-OH | Phenylacetic acid | Phenylacetic acid | 491.65 |
| 2055-202 | Boc-L-Asp(OBzl)-OH | Phenylacetic acid | Phenylacetic acid | 521.67 |
| 2055-203 | Boc-L-Glu(OBzl)-OH | Phenylacetic acid | Phenylacetic acid | 535.7 |
| 2055-204 | Boc-L-Phe-OH | Phenylacetic acid | Phenylacetic acid | 567.74 |
| 2055-205 | Boc-Gly-OH | Phenylacetic acid | Phenylacetic acid | 477.62 |
| 2055-206 | Boc-L-Ile-OH | Phenylacetic acid | Phenylacetic acid | 533.73 |
| 2055-207 | Boc-L-His(Tos)-OH | Phenylacetic acid | Phenylacetic acid | 557.71 |
| 2055-208 | Boc-L-Lys(ClZ)-OH | Phenylacetic acid | Phenylacetic acid | 548.74 |
| 2055-209 | Boc-L-Leu-OH | Phenylacetic acid | Phenylacetic acid | 533.73 |
| 2055-210 | Boc-L-Met(O)-OH | Phenylacetic acid | Phenylacetic acid | 567.77 |
| 2055-211 | Boc-L-Asn-OH | Phenylacetic acid | Phenylacetic acid | 520.69 |
| 2055-212 | Boc-L-Pro-OH | Phenylacetic acid | Phenylacetic acid | 517.69 |
| 2055-213 | Boc-L-Gln-OH | Phenylacetic acid | Phenylacetic acid | 534.72 |
| 2055-214 | Boc-L-Arg(Tos)-OH | Phenylacetic acid | Phenylacetic acid | 576.76 |
| 2055-215 | Boc-L-Ser(Bzl)-OH | Phenylacetic acid | Phenylacetic acid | 507.65 |
| 2055-216 | Boc-L-Thr(Bzl)-OH | Phenylacetic acid | Phenylacetic acid | 521.67 |
| 2055-217 | Boc-L-Val-OH | Phenylacetic acid | Phenylacetic acid | 519.7 |
| 2055-218 | Boc-L-Trp-OH | Phenylacetic acid | Phenylacetic acid | 606.78 |
| 2055-219 | Boc-L-Tyr(2-Br-Z)-OH | Phenylacetic acid | Phenylacetic acid | 583.74 |
| 2055-220 | Boc-D-Ala-OH | Phenylacetic acid | Phenylacetic acid | 491.65 |
| 2055-221 | Boc-D-Asp(OBzl)-OH | Phenylacetic acid | Phenylacetic acid | 521.67 |
| 2055-222 | Boc-D-Glu(OBzl)-OH | Phenylacetic acid | Phenylacetic acid | 535.7 |
| 2055-223 | Boc-D-Phe-OH | Phenylacetic acid | Phenylacetic acid | 567.74 |
| 2055-224 | Boc-D-His(Tos)-OH | Phenylacetic acid | Phenylacetic acid | 557.71 |
| 2055-225 | Boc-D-Ile-OH | Phenylacetic acid | Phenylacetic acid | 533.73 |
| 2055-226 | Boc-D-Lys(ClZ)-OH | Phenylacetic acid | Phenylacetic acid | 548.74 |
| 2055-227 | Boc-D-Leu-OH | Phenylacetic acid | Phenylacetic acid | 533.73 |
| 2055-228 | Boc-D-Met(O)-OH | Phenylacetic acid | Phenylacetic acid | 567.77 |
| 2055-229 | Boc-D-Asn-OH | Phenylacetic acid | Phenylacetic acid | 520.69 |
| 2055-230 | Boc-D-Pro-OH | Phenylacetic acid | Phenylacetic acid | 517.69 |
| 2055-231 | Boc-D-Gln-OH | Phenylacetic acid | Phenylacetic acid | 534.72 |
| 2055-232 | Boc-D-Arg(Tos)-OH | Phenylacetic acid | Phenylacetic acid | 576.76 |
| 2055-233 | Boc-D-Ser(Bzl)-OH | Phenylacetic acid | Phenylacetic acid | 507.65 |
| 2055-234 | Boc-D-Thr(Bzl)-OH | Phenylacetic acid | Phenylacetic acid | 521.67 |
| 2055-235 | Boc-D-Val-OH | Phenylacetic acid | Phenylacetic acid | 519.7 |
| 2055-236 | Boc-D-Trp-OH | Phenylacetic acid | Phenylacetic acid | 606.78 |
| 2055-237 | Boc-D-Tyr(2-Br-Z)-OH | Phenylacetic acid | Phenylacetic acid | 583.74 |
| 2055-238 | Boc-L-Aib-OH | Phenylacetic acid | Phenylacetic acid | 505.67 |
| 2055-239 | Boc-D-Nva-OH | Phenylacetic acid | Phenylacetic acid | 519.7 |
| 2055-240 | Boc-L-Nle-OH | Phenylacetic acid | Phenylacetic acid | 533.7 |
| 2055-241 | Boc-D-Nle-OH | Phenylacetic acid | Phenylacetic acid | 533.73 |
| 2055-242 | Boc-L-Orn(ClZ)-OH | Phenylacetic acid | Phenylacetic acid | 534.72 |
| 2055-243 | Boc-D-Orn(ClZ)-OH | Phenylacetic acid | Phenylacetic acid | 534.72 |
| 2055-244 | Boc-L-Phg-OH | Phenylacetic acid | Phenylacetic acid | 553.72 |
| 2055-245 | Boc-D-Phg-OH | Phenylacetic acid | Phenylacetic acid | 553.72 |
| 2055-246 | Boc-L-2-Naphtylala-OH | Phenylacetic acid | Phenylacetic acid | 617.8 |
| 2055-247 | Boc-D-2-Naphtylala-OH | Phenylacetic acid | Phenylacetic acid | 617.8 |
| 2055-248 | Boc-b-Ala-OH | Phenylacetic acid | Phenylacetic acid | 477.62 |
| 2055-249 | Boc-L-Cha-OH | Phenylacetic acid | Phenylacetic acid | 573.79 |
| 2055-250 | Boc-D-Cha-OH | Phenylacetic acid | Phenylacetic acid | 573.79 |
| 2055-251 | Boc-L-p-Nitro-Phenylalanine | Phenylacetic acid | Phenylacetic acid | 612.74 |
| 2055-252 | Boc-D-p-Nitro-Phenylalanine | Phenylacetic acid | Phenylacetic acid | 612.74 |
| 2055-253 | Boc-L-4-Chlorophenylalanine | Phenylacetic acid | Phenylacetic acid | 602.19 |
| 2055-254 | Boc-D-4-Chlorophenylalanine | Phenylacetic acid | Phenylacetic acid | 602.19 |
| 2055-255 | Boc-L-4-Fluorophenylalanine | Phenylacetic acid | Phenylacetic acid | 585.73 |
| 2055-256 | Boc-D-4-Fluorophenylalanine | Phenylacetic acid | Phenylacetic acid | 585.73 |

FIG. 7.1A

| | | | | |
|---|---|---|---|---|
| 2055-259 | Boc-Tyr-OH | 1-phenyl-1-cyclopropanecarboxylic acid | Phenylacetic acid | 609.78 |
| 2055-260 | Boc-Tyr-OH | 2-Phenylbutyric Acid | Phenylacetic acid | 611.8 |
| 2055-261 | Boc-Tyr-OH | 3-Phenylbutyric Acid | Phenylacetic acid | 611.8 |
| 2055-262 | Boc-Tyr-OH | m-Tolylacetic acid | Phenylacetic acid | 597.77 |
| 2055-263 | Boc-Tyr-OH | 3-Fluorophenylacetic Acid | Phenylacetic acid | 601.73 |
| 2055-264 | Boc-Tyr-OH | 3-Bromophenylacetic Acid | Phenylacetic acid | 662.64 |
| 2055-265 | Boc-Tyr-OH | p-Tolyacetic acid | Phenylacetic acid | 597.77 |
| 2055-266 | Boc-Tyr-OH | 4-Fluorophenylacetic acid | Phenylacetic acid | 601.73 |
| 2055-267 | Boc-Tyr-OH | 3-Methoxyphenylacetic acid | Phenylacetic acid | 613.77 |
| 2055-268 | Boc-Tyr-OH | 4-Bromophenylacetic acid | Phenylacetic acid | 662.64 |
| 2055-269 | Boc-Tyr-OH | 4-Methoxyphenylacetic acid | Phenylacetic acid | 613.77 |
| 2055-270 | Boc-Tyr-OH | 3,4-Dimethoxyphenyl acetic acid | Phenylacetic acid | 643.8 |
| 2055-271 | Boc-Tyr-OH | 4-isobutyl-alpha-Methylphenylacetic Acid | Phenylacetic acid | 667.9 |
| 2055-272 | Boc-Tyr-OH | 3,4-Dichlorophenylacetic acid | Phenylacetic acid | 652.63 |
| 2055-273 | Boc-Tyr-OH | 3,5-Bis(Trifluoromethyl)-Phenylacetic acid | Phenylacetic acid | 719.74 |
| 2055-274 | Boc-Tyr-OH | 3-(3,4-Dimethoxyphenyl)-propionic Acid | Phenylacetic acid | 657.82 |
| 2055-275 | Boc-Tyr-OH | Phenylacetic acid | Phenylacetic acid | 583.74 |
| 2055-276 | Boc-Tyr-OH | 3,4,5-Trimethoxybenzoic acid | Phenylacetic acid | 673.82 |
| 2055-277 | Boc-Tyr-OH | Butyric Acid | Phenylacetic acid | 535.7 |
| 2055-278 | Boc-Tyr-OH | Heptanoic Acid | Phenylacetic acid | 577.78 |
| 2055-279 | Boc-Tyr-OH | Isobutyric Acid | Phenylacetic acid | 535.7 |
| 2055-280 | Boc-Tyr-OH | 2-Methylbutiric Acid | Phenylacetic acid | 549.73 |
| 2055-281 | Boc-Tyr-OH | Isovaleric acid | Phenylacetic acid | 563.75 |
| 2055-282 | Boc-Tyr-OH | 3-Methylvaleric acid | Phenylacetic acid | 563.75 |
| 2055-283 | Boc-Tyr-OH | p-Toluic Acid | Phenylacetic acid | 599.74 |
| 2055-284 | Boc-Tyr-OH | cyclopentanecarboxylic acid. | Phenylacetic acid | 561.74 |
| 2055-285 | Boc-Tyr-OH | cyclohexanecarboxilic acid | Phenylacetic acid | 575.76 |
| 2055-286 | Boc-Tyr-OH | cyclohexylacetic acid | Phenylacetic acid | 589.79 |
| 2055-287 | Boc-Tyr-OH | cyclohexanebutyric acid | Phenylacetic acid | 617.84 |
| 2055-288 | Boc-Tyr-OH | cycloheptanecarboxylic acid | Phenylacetic acid | 589.79 |
| 2055-289 | Boc-Tyr-OH | 2-Methylcyclopropanecarboxylic acid | Phenylacetic acid | 547.71 |
| 2055-290 | Boc-Tyr-OH | cyclobutanecarboxylic acid | Phenylacetic acid | 547.71 |
| 2055-291 | Boc-Tyr-OH | 3-cyclopentylpropionic acid | Phenylacetic acid | 589.79 |
| 2055-292 | Boc-Tyr-OH | cyclohexanepropionic acid | Phenylacetic acid | 603.82 |
| 2055-293 | Boc-Tyr-OH | 4-methyl-1-cyclohexanecarboxylic acid | Phenylacetic acid | 589.79 |
| 2055-294 | Boc-Tyr-OH | 4-tert-butyl-cyclohexanecarboxylic acid | Phenylacetic acid | 631.87 |
| 2055-295 | Boc-Tyr-OH | 4-biphenylacetic acid | Phenylacetic acid | 659.84 |
| 2055-296 | Boc-Tyr-OH | 1-Adamantanecarboxylic acid | Phenylacetic acid | 627.84 |
| 2055-297 | Boc-Tyr-OH | 4-Methylvaleric acid | Phenylacetic acid | 563.75 |
| 2055-298 | Boc-Tyr-OH | 2-norbornaneacetic acid | Phenylacetic acid | 601.8 |
| 2055-299 | Boc-Tyr-OH | indole-3-acetic acid | Phenylacetic acid | 522.78 |
| 2055-300 | Boc-Tyr-OH | 5-methyl-3-phenylisoxazole-4-carboxy | Phenylacetic acid | 650.79 |
| 2055-301 | Boc-Tyr-OH | 1-methyl-2-pyrrole carboxylic acid | Phenylacetic acid | 572.72 |
| 2055-302 | Boc-Tyr-OH | (4-pyridylthio) acetic acid | Phenylacetic acid | 616.8 |
| 2055-303 | Boc-Tyr-OH | 2-pyrazine carboxylic acid | Phenylacetic acid | 571.69 |
| 2055-304 | Boc-Tyr-OH | 2-thiophenecarboxylic acid | Phenylacetic acid | 575.74 |

FIG. 7.1B

| | | | | |
|---|---|---|---|---|
| 2055-305 | Boc-Tyr-OH | Phenylacetic acid | 1-phenyl-1-cyclopropanecarboxylic acid | 609.78 |
| 2055-306 | Boc-Tyr-OH | Phenylacetic acid | 2-Phenylbutyric Acid | 611.8 |
| 2055-307 | Boc-Tyr-OH | Phenylacetic acid | 3-Phenylbutyric Acid | 611.8 |
| 2055-308 | Boc-Tyr-OH | Phenylacetic acid | m-Tolylacetic acid | 597.77 |
| 2055-309 | Boc-Tyr-OH | Phenylacetic acid | 3-Fluorophenylacetic Acid | 601.73 |
| 2055-310 | Boc-Tyr-OH | Phenylacetic acid | 3-Bromophenylacetic Acid | 662.64 |
| 2055-311 | Boc-Tyr-OH | Phenylacetic acid | p-Tolyacetic acid | 597.77 |
| 2055-312 | Boc-Tyr-OH | Phenylacetic acid | 4-Fluorophenylacetic acid | 601.73 |
| 2055-313 | Boc-Tyr-OH | Phenylacetic acid | 3-Methoxyphenylacetic acid | 613.77 |
| 2055-314 | Boc-Tyr-OH | Phenylacetic acid | 4-Bromophenylacetic acid | 662.64 |
| 2055-315 | Boc-Tyr-OH | Phenylacetic acid | 4-Methoxyphenylacetic acid | 613.77 |
| 2055-316 | Boc-Tyr-OH | Phenylacetic acid | 3,4-Dimethoxyphenyl acetic acid | 643.8 |
| 2055-317 | Boc-Tyr-OH | Phenylacetic acid | 4-isobutyl-alpha-Methylphenylacetic Acid | 667.9 |
| 2055-318 | Boc-Tyr-OH | Phenylacetic acid | 3,4-Dichlorophenylacetic acid | 652.63 |
| 2055-319 | Boc-Tyr-OH | Phenylacetic acid | 3,5-Bis(Trifluoromethyl)-Phenylacetic acid | 695.96 |
| 2055-320 | Boc-Tyr-OH | Phenylacetic acid | 3-(3,4-Dimethoxyphenyl)-propionic Acid | 657.82 |
| 2055-321 | Boc-Tyr-OH | Phenylacetic acid | Phenylacetic acid | 583.74 |
| 2055-322 | Boc-Tyr-OH | Phenylacetic acid | 3,4,5-Trimethoxybenzoic acid | 673.82 |
| 2055-323 | Boc-Tyr-OH | Phenylacetic acid | Butyric Acid | 535.7 |
| 2055-324 | Boc-Tyr-OH | Phenylacetic acid | Heptanoic Acid | 577.78 |
| 2055-325 | Boc-Tyr-OH | Phenylacetic acid | Isobutyric Acid | 535.7 |
| 2055-326 | Boc-Tyr-OH | Phenylacetic acid | 2-Methylbutiric Acid | 549.73 |
| 2055-327 | Boc-Tyr-OH | Phenylacetic acid | isovaleric acid | 563.75 |
| 2055-328 | Boc-Tyr-OH | Phenylacetic acid | 3-Methylvaleric acid | 563.75 |
| 2055-329 | Boc-Tyr-OH | Phenylacetic acid | p-Toluic Acid | 599.74 |
| 2055-330 | Boc-Tyr-OH | Phenylacetic acid | cyclopentanecarboxylic acid. | 561.74 |
| 2055-331 | Boc-Tyr-OH | Phenylacetic acid | cyclohexanecarboxilic acid | 575.76 |
| 2055-332 | Boc-Tyr-OH | Phenylacetic acid | cyclohexylacetic acid | 589.79 |
| 2055-333 | Boc-Tyr-OH | Phenylacetic acid | cyclohexanebutyric acid | 617.84 |
| 2055-334 | Boc-Tyr-OH | Phenylacetic acid | cycloheptanecarboxylic acid | 589.79 |
| 2055-335 | Boc-Tyr-OH | Phenylacetic acid | 2-Methylcyclopropanecarboxylic acid | 547.71 |
| 2055-336 | Boc-Tyr-OH | Phenylacetic acid | cyclobutanecarboxylic acid | 547.71 |
| 2055-337 | Boc-Tyr-OH | Phenylacetic acid | 3-cyclopentylpropionic acid | 589.79 |
| 2055-338 | Boc-Tyr-OH | Phenylacetic acid | cyclohexanepropionic acid | 603.82 |
| 2055-339 | Boc-Tyr-OH | Phenylacetic acid | 4-methyl-1-cyclohexanancarboxylic acid | 589.79 |
| 2055-340 | Boc-Tyr-OH | Phenylacetic acid | 4-tert-butyl-cyclohexanoocarboxylic acid | 631.87 |
| 2055-341 | Boc-Tyr-OH | Phenylacetic acid | 4-biphenylacetic acid | 659.84 |
| 2055-342 | Boc-Tyr-OH | Phenylacetic acid | 1-Adamantanecarboxylic acid | 627.84 |
| 2055-343 | Boc-Tyr-OH | Phenylacetic acid | 4-Methylvaleric acid | 563.75 |
| 2055-344 | Boc-Tyr-OH | Phenylacetic acid | 2-norbornaneacetic acid | 601.8 |
| 2055-345 | Boc-Tyr-OH | Phenylacetic acid | indole-3-acetic acid | 622.78 |
| 2055-346 | Boc-Tyr-OH | Phenylacetic acid | 5-methyl-3-phenylisoxazole-4-carboxylic acid | 650.79 |
| 2055-347 | Boc-Tyr-OH | Phenylacetic acid | 1-methyl-2-pyrrole carboxylic acid | 572.72 |
| 2055-348 | Boc-Tyr-OH | Phenylacetic acid | (4-pyridithio) acetic acid | 616.8 |
| 2055-349 | Boc-Tyr-OH | Phenylacetic acid | 2-pyrazine carboxylic acid | 571.69 |
| 2055-350 | Boc-Tyr-OH | Phenylacetic acid | 2-thiophenecarboxylic acid | 575.74 |

FIG. 7.1C

| Controls | R1 | R2 | R3 | MW |
|---|---|---|---|---|
| 2055-201 | S-methyl | Phenylethyl | Phenylethyl | 491.65 |
| 2055-202 | S-2-hydroxyethyl | Phenylethyl | Phenylethyl | 521.67 |
| 2055-203 | S-3-hydroxypropyl | Phenylethyl | Phenylethyl | 535.7 |
| 2055-204 | S-benzyl | Phenylethyl | Phenylethyl | 567.74 |
| 2055-205 | hydrogen | Phenylethyl | Phenylethyl | 477.62 |
| 2055-206 | S-2-butyl | Phenylethyl | Phenylethyl | 533.73 |
| 2055-207 | S-4-methylimidazole | Phenylethyl | Phenylethyl | 557.71 |
| 2055-208 | S-N-butyl-N-methyl-2-phenyla | Phenylethyl | Phenylethyl | 548.74 |
| 2055-209 | S-isobutyl | Phenylethyl | Phenylethyl | 533.73 |
| 2055-210 | S-Ethyl-methyl-sulfane | Phenylethyl | Phenylethyl | 567.77 |
| 2055-211 | S-N-ethyl-2-phenylacetamide | Phenylethyl | Phenylethyl | 520.69 |
| 2055-212 | s-Pyrrolidine | Phenylethyl | Phenylethyl | 517.69 |
| 2055-213 | S-2-phenyl-N-propylacetamide | Phenylethyl | Phenylethyl | 534.72 |
| 2055-214 | S-1-propylguanidine | Phenylethyl | Phenylethyl | 576.76 |
| 2055-215 | R-hydroxy-methyl | Phenylethyl | Phenylethyl | 507.65 |
| 2055-216 | R-1-hydroxy-ethyl | Phenylethyl | Phenylethyl | 521.67 |
| 2055-217 | S-isopropyl | Phenylethyl | Phenylethyl | 519.7 |
| 2055-218 | S-3-methyl-1H-indole | Phenylethyl | Phenylethyl | 606.78 |
| 2055-219 | S-4-hydroxybenzyl | Phenylethyl | Phenylethyl | 583.74 |
| 2055-220 | R-methyl | Phenylethyl | Phenylethyl | 491.65 |
| 2055-221 | S-2-hydroxyethyl | Phenylethyl | Phenylethyl | 521.67 |
| 2055-222 | S-3-hydroxypropyl | Phenylethyl | Phenylethyl | 535.7 |
| 2055-223 | R-benzyl | Phenylethyl | Phenylethyl | 567.74 |
| 2055-224 | R-4-methylimidazole | Phenylethyl | Phenylethyl | 557.71 |
| 2055-225 | R-2-butyl | Phenylethyl | Phenylethyl | 533.73 |
| 2055-226 | R-N-butyl-N-methyl-2-phenyla | Phenylethyl | Phenylethyl | 548.74 |
| 2055-227 | R-isobutyl | Phenylethyl | Phenylethyl | 533.73 |
| 2055-228 | R-Ethyl-methyl-sulfane | Phenylethyl | Phenylethyl | 567.77 |
| 2055-229 | R-N-ethyl-2-phenylacetamide | Phenylethyl | Phenylethyl | 520.69 |
| 2055-230 | R-Pyrrolidine | Phenylethyl | Phenylethyl | 517.69 |
| 2055-231 | R-2-phenyl-N-propylacetamide | Phenylethyl | Phenylethyl | 534.72 |
| 2055-232 | R-1-propylguanidine | Phenylethyl | Phenylethyl | 576.76 |
| 2055-233 | S-hydroxy-methyl | Phenylethyl | Phenylethyl | 507.65 |
| 2055-234 | S-1-hydroxy-ethyl | Phenylethyl | Phenylethyl | 521.67 |
| 2055-235 | R-isopropyl | Phenylethyl | Phenylethyl | 519.7 |
| 2055-236 | R-3-methyl-1H-indole | Phenylethyl | Phenylethyl | 606.78 |
| 2055-237 | R-4-hydroxybenzyl | Phenylethyl | Phenylethyl | 583.74 |
| 2055-238 | S-dimethyl | Phenylethyl | Phenylethyl | 505.67 |
| 2055-239 | R-propyl | Phenylethyl | Phenylethyl | 519.7 |
| 2055-240 | S-butyl | Phenylethyl | Phenylethyl | 533.7 |
| 2055-241 | R-butyl | Phenylethyl | Phenylethyl | 533.73 |
| 2055-242 | S-N-proyl-N-methyl-2-phenyla | Phenylethyl | Phenylethyl | 534.72 |
| 2055-243 | R-N-propyl-N-methyl-2-pheny | Phenylethyl | Phenylethyl | 534.72 |
| 2055-244 | S-phenyl | Phenylethyl | Phenylethyl | 553.72 |
| 2055-245 | D-phenyl | Phenylethyl | Phenylethyl | 553.72 |
| 2055-246 | S-2-methylnaphthalene | Phenylethyl | Phenylethyl | 617.8 |
| 2055-247 | R-2-methylnaphthalene | Phenylethyl | Phenylethyl | 617.8 |
| 2055-248 | SPECIAL STRUCTURE | Phenylethyl | Phenylethyl | 477.62 |
| 2055-249 | S-cyclohexyl-methyl | Phenylethyl | Phenylethyl | 573.79 |
| 2055-250 | R-cyclohexyl-methyl | Phenylethyl | Phenylethyl | 573.79 |
| 2055-251 | S-p-nitrobenzyl | Phenylethyl | Phenylethyl | 612.74 |
| 2055-252 | R-p-nitrobenzyl | Phenylethyl | Phenylethyl | 612.74 |
| 2055-253 | S-4-cholorobenzyl | Phenylethyl | Phenylethyl | 602.19 |
| 2055-254 | R-4-cholorobenzyl | Phenylethyl | Phenylethyl | 602.19 |
| 2055-255 | S-4-Fluorobenzyl | Phenylethyl | Phenylethyl | 585.73 |
| 2055-256 | D-4-Fluorobenzyl | Phenylethyl | Phenylethyl | 585.73 |

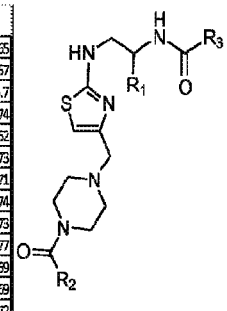

TPI-2055

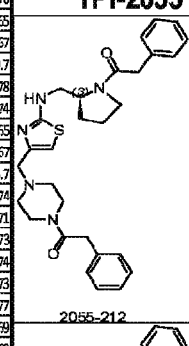

2055-212

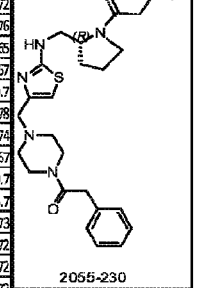

2055-230

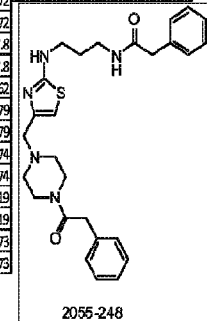

| | | | | |
|---|---|---|---|---|
| 2055-259 | 4-hydroxyphenylmethyl | (1-phenyl-cyclopropyl)-methyl | Phenylethyl | 609.78 |
| 2055-260 | 4-hydroxyphenylmethyl | 2-phenylbutyl | Phenylethyl | 611.8 |
| 2055-261 | 4-hydroxyphenylmethyl | 3-Phenylbutyric Acid | Phenylethyl | 611.8 |
| 2055-262 | 4-hydroxyphenylmethyl | m-tolylethyl | Phenylethyl | 597.77 |
| 2055-263 | 4-hydroxyphenylmethyl | 3-Fluorophenylethyl | Phenylethyl | 601.73 |
| 2055-264 | 4-hydroxyphenylmethyl | 3-Bromophenylethyl | Phenylethyl | 662.64 |
| 2055-265 | 4-hydroxyphenylmethyl | p-tolylethyl | Phenylethyl | 597.77 |
| 2055-266 | 4-hydroxyphenylmethyl | 4-Fluorophenylethyl | Phenylethyl | 601.73 |
| 2055-267 | 4-hydroxyphenylmethyl | 3-Methoxyphenylethyl | Phenylethyl | 613.77 |
| 2055-268 | 4-hydroxyphenylmethyl | 4-Bromophenylethyl | Phenylethyl | 662.64 |
| 2055-269 | 4-hydroxyphenylmethyl | 4-Methoxyphenylethyl | Phenylethyl | 613.77 |
| 2055-270 | 4-hydroxyphenylmethyl | 3,4-Dimethoxyphenylethyl | Phenylethyl | 643.8 |
| 2055-271 | 4-hydroxyphenylmethyl | 4-Isobutyl-alpha-Methylphenyle | Phenylethyl | 667.9 |
| 2055-272 | 4-hydroxyphenylmethyl | 3,4-Dichlorophenylethyl | Phenylethyl | 652.63 |
| 2055-273 | 4-hydroxyphenylmethyl | 3,5-Bis(Trifluoromethyl)-Phenyle | Phenylethyl | 719.74 |
| 2055-274 | 4-hydroxyphenylmethyl | 3-(3,4-Dimethoxyphenyl)-propyl | Phenylethyl | 657.82 |
| 2055-275 | 4-hydroxyphenylmethyl | phenethyl | Phenylethyl | 583.74 |
| 2055-276 | 4-hydroxyphenylmethyl | 3,4,5-Trimethoxybenzyl | Phenylethyl | 673.82 |
| 2055-277 | 4-hydroxyphenylmethyl | butyl | Phenylethyl | 535.7 |
| 2055-278 | 4-hydroxyphenylmethyl | heptyl | Phenylethyl | 577.78 |
| 2055-279 | 4-hydroxyphenylmethyl | isobutyl | Phenylethyl | 535.7 |
| 2055-280 | 4-hydroxyphenylmethyl | 2-Methylbutyl | Phenylethyl | 549.73 |
| 2055-281 | 4-hydroxyphenylmethyl | 3-methylbutyl | Phenylethyl | 563.75 |
| 2055-282 | 4-hydroxyphenylmethyl | 2-Methylbutyl | Phenylethyl | 563.75 |
| 2055-283 | 4-hydroxyphenylmethyl | 4-methylbenzyl | Phenylethyl | 599.74 |
| 2055-284 | 4-hydroxyphenylmethyl | cyclopentyl-methyl | Phenylethyl | 561.74 |
| 2055-285 | 4-hydroxyphenylmethyl | cyclohexyl-methyl | Phenylethyl | 575.76 |
| 2055-286 | 4-hydroxyphenylmethyl | cyclohexyl-ethyl | Phenylethyl | 589.79 |
| 2055-287 | 4-hydroxyphenylmethyl | cyclohexyl-butyl | Phenylethyl | 617.84 |
| 2055-288 | 4-hydroxyphenylmethyl | cycloheptyl-methyl | Phenylethyl | 589.79 |
| 2055-289 | 4-hydroxyphenylmethyl | (2-methylcyclopropyl)methyl | Phenylethyl | 547.71 |
| 2055-290 | 4-hydroxyphenylmethyl | cyclobutylmethyl | Phenylethyl | 547.71 |
| 2055-291 | 4-hydroxyphenylmethyl | 3-cyclopentylpropyl | Phenylethyl | 589.79 |
| 2055-292 | 4-hydroxyphenylmethyl | 3-cyclohexylpropyl | Phenylethyl | 603.82 |
| 2055-293 | 4-hydroxyphenylmethyl | 4-methyl-1-cyclohexylmethyl | Phenylethyl | 589.79 |
| 2055-294 | 4-hydroxyphenylmethyl | 4-tert-butyl-cyclohexylmethyl | Phenylethyl | 631.87 |
| 2055-295 | 4-hydroxyphenylmethyl | 2-([1,1'-biphenyl]-4-yl)ethyl | Phenylethyl | 659.84 |
| 2055-296 | 4-hydroxyphenylmethyl | 1-Adamantylmethyl | Phenylethyl | 627.84 |
| 2055-297 | 4-hydroxyphenylmethyl | 4-methylpentyl | Phenylethyl | 563.75 |
| 2055-298 | 4-hydroxyphenylmethyl | 2-norbornylethyl | Phenylethyl | 601.8 |
| 2055-299 | 4-hydroxyphenylmethyl | 2-(1H-indol-3-yl)ethyl | Phenylethyl | 622.78 |
| 2055-300 | 4-hydroxyphenylmethyl | (5-methyl-3-phenylisoxazol-4-yl) | Phenylethyl | 650.79 |
| 2055-301 | 4-hydroxyphenylmethyl | (1-methyl-1H-pyrrol-2-yl)methyl | Phenylethyl | 572.72 |
| 2055-302 | 4-hydroxyphenylmethyl | 2-(pyridin-4-ylthio)ethyl | Phenylethyl | 616.8 |
| 2055-303 | 4-hydroxyphenylmethyl | pyrazin-2-ylmethyl | Phenylethyl | 571.69 |
| 2055-304 | 4-hydroxyphenylmethyl | thiophen-2-ylmethyl | Phenylethyl | 575.74 |

FIG. 8.1B

| | | | | |
|---|---|---|---|---|
| 2055-305 | 4-hydroxyphenylmethyl | phenylethyl | (1-phenyl-cyclopropyl)-methyl | 609.78 |
| 2055-306 | 4-hydroxyphenylmethyl | phenylethyl | 2-phenylbutyl | 611.8 |
| 2055-307 | 4-hydroxyphenylmethyl | phenylethyl | 3-Phenylbutyric Acid | 611.8 |
| 2055-308 | 4-hydroxyphenylmethyl | phenylethyl | m-tolylethyl | 597.77 |
| 2055-309 | 4-hydroxyphenylmethyl | phenylethyl | 3-Fluorophenylethyl | 601.73 |
| 2055-310 | 4-hydroxyphenylmethyl | phenylethyl | 3-Bromophenylethyl | 662.64 |
| 2055-311 | 4-hydroxyphenylmethyl | phenylethyl | p-tolylethyl | 597.77 |
| 2055-312 | 4-hydroxyphenylmethyl | phenylethyl | 4-Fluorophenylethyl | 601.73 |
| 2055-313 | 4-hydroxyphenylmethyl | phenylethyl | 3-Methoxyphenylethyl | 613.77 |
| 2055-314 | 4-hydroxyphenylmethyl | phenylethyl | 4-Bromophenylethyl | 662.64 |
| 2055-315 | 4-hydroxyphenylmethyl | phenylethyl | 4-Methoxyphenylethyl | 613.77 |
| 2055-316 | 4-hydroxyphenylmethyl | phenylethyl | 3,4-Dimethoxyphenylethyl | 643.8 |
| 2055-317 | 4-hydroxyphenylmethyl | phenylethyl | 4-isobutyl-alpha-Methylphen | 667.9 |
| 2055-318 | 4-hydroxyphenylmethyl | phenylethyl | 3,4-Dichlorophenylethyl | 652.63 |
| 2055-319 | 4-hydroxyphenylmethyl | phenylethyl | 3,5-Bis(Trifluoromethyl)-Pher | 695.96 |
| 2055-320 | 4-hydroxyphenylmethyl | phenylethyl | 3-(3,4-Dimethoxyphenyl)-pro | 657.82 |
| 2055-321 | 4-hydroxyphenylmethyl | phenylethyl | phenethyl | 583.74 |
| 2055-322 | 4-hydroxyphenylmethyl | phenylethyl | 3,4,5-Trimethoxybenzyl | 673.82 |
| 2055-323 | 4-hydroxyphenylmethyl | phenylethyl | butyl | 535.7 |
| 2055-324 | 4-hydroxyphenylmethyl | phenylethyl | heptyl | 577.78 |
| 2055-325 | 4-hydroxyphenylmethyl | phenylethyl | isobutyl | 535.7 |
| 2055-326 | 4-hydroxyphenylmethyl | phenylethyl | 2-Methylbutyl | 549.73 |
| 2055-327 | 4-hydroxyphenylmethyl | phenylethyl | 3-methylbutyl | 563.75 |
| 2055-328 | 4-hydroxyphenylmethyl | phenylethyl | 2-Methylbutyl | 563.75 |
| 2055-329 | 4-hydroxyphenylmethyl | phenylethyl | 4-methylbenzyl | 599.74 |
| 2055-330 | 4-hydroxyphenylmethyl | phenylethyl | cyclopenty-methyl | 561.74 |
| 2055-331 | 4-hydroxyphenylmethyl | phenylethyl | cyclohexyl-methyl | 575.76 |
| 2055-332 | 4-hydroxyphenylmethyl | phenylethyl | cyclohexyl-ethyl | 589.79 |
| 2055-333 | 4-hydroxyphenylmethyl | phenylethyl | cyclohexyl-butyl | 617.84 |
| 2055-334 | 4-hydroxyphenylmethyl | phenylethyl | cycloheptyl-methyl | 589.79 |
| 2055-335 | 4-hydroxyphenylmethyl | phenylethyl | (2-methylcyclopropyl)methyl | 547.71 |
| 2055-336 | 4-hydroxyphenylmethyl | phenylethyl | cyclobutylmethyl | 547.71 |
| 2055-337 | 4-hydroxyphenylmethyl | phenylethyl | 3-cyclopentylpropyl | 589.79 |
| 2055-338 | 4-hydroxyphenylmethyl | phenylethyl | 3-cyclohexylpropyl | 603.82 |
| 2055-339 | 4-hydroxyphenylmethyl | phenylethyl | 4-methyl-1-cyclohexylmethyl | 589.79 |
| 2055-340 | 4-hydroxyphenylmethyl | phenylethyl | 4-tert-butyl-cyclohexylmethyl | 631.87 |
| 2055-341 | 4-hydroxyphenylmethyl | phenylethyl | 2-([1,1'-biphenyl]-4-yl)ethyl | 659.84 |
| 2055-342 | 4-hydroxyphenylmethyl | phenylethyl | 1-Adamantylmethyl | 627.84 |
| 2055-343 | 4-hydroxyphenylmethyl | phenylethyl | 4-methylpentyl | 563.75 |
| 2055-344 | 4-hydroxyphenylmethyl | phenylethyl | 2-norbornylethyl | 601.8 |
| 2055-345 | 4-hydroxyphenylmethyl | phenylethyl | 2-(1H-indol-3-yl)ethyl | 622.78 |
| 2055-346 | 4-hydroxyphenylmethyl | phenylethyl | (5-methyl-3-phenylisoxazol-4 | 650.79 |
| 2055-347 | 4-hydroxyphenylmethyl | phenylethyl | (1-methyl-1H-pyrrol-2-yl)met | 572.72 |
| 2055-348 | 4-hydroxyphenylmethyl | phenylethyl | 2-(pyridin-4-ylthio)ethyl | 616.8 |
| 2055-349 | 4-hydroxyphenylmethyl | phenylethyl | pyrazin-2-ylmethyl | 571.69 |
| 2055-350 | 4-hydroxyphenylmethyl | phenylethyl | thiophen-2-ylmethyl | 575.74 |

FIG. 8.1C

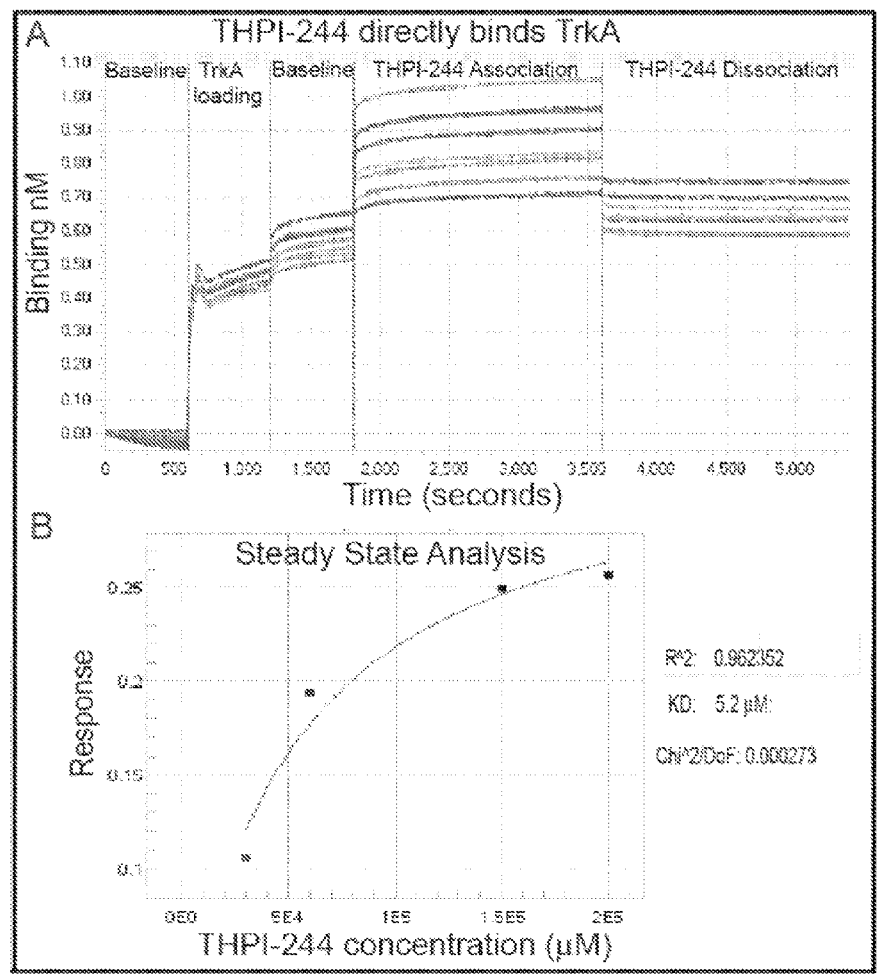
FIG. 9.1

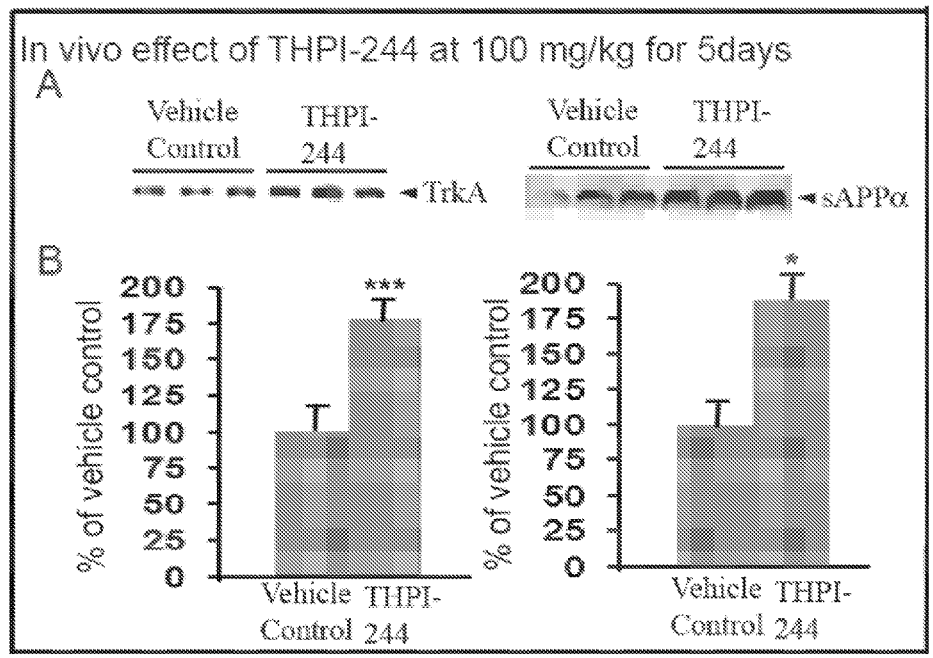
FIG. 9.2

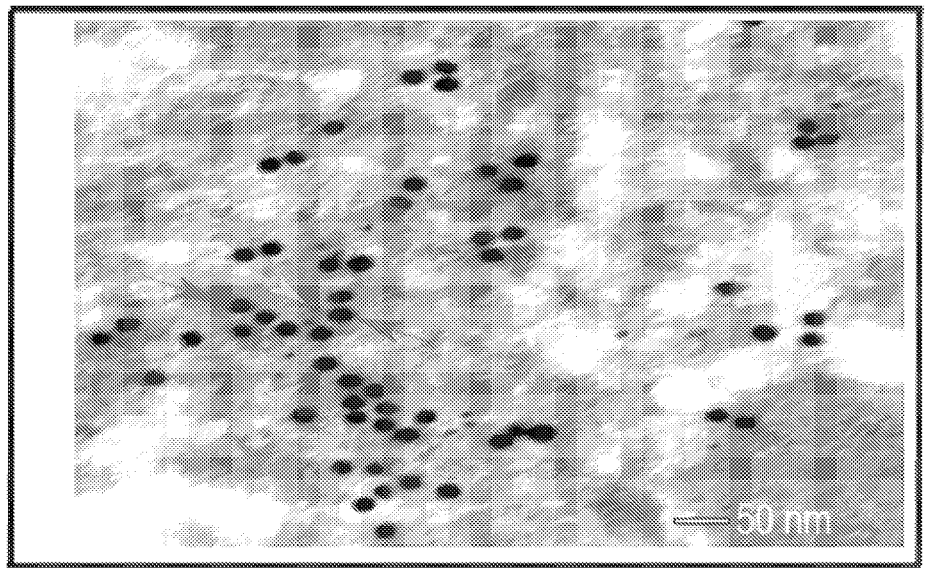
FIG. 9.3
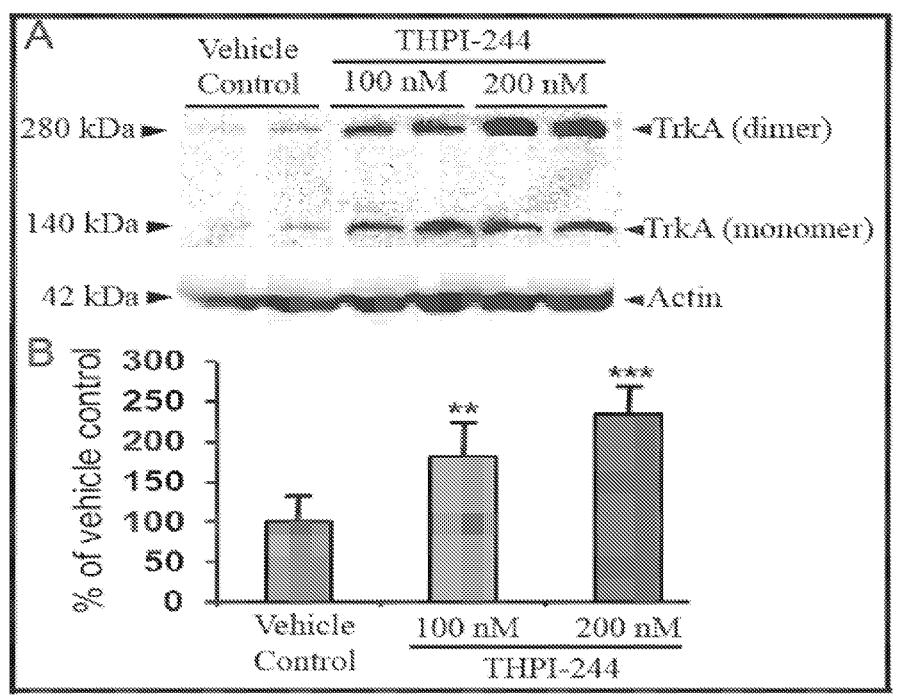
FIG. 9.4

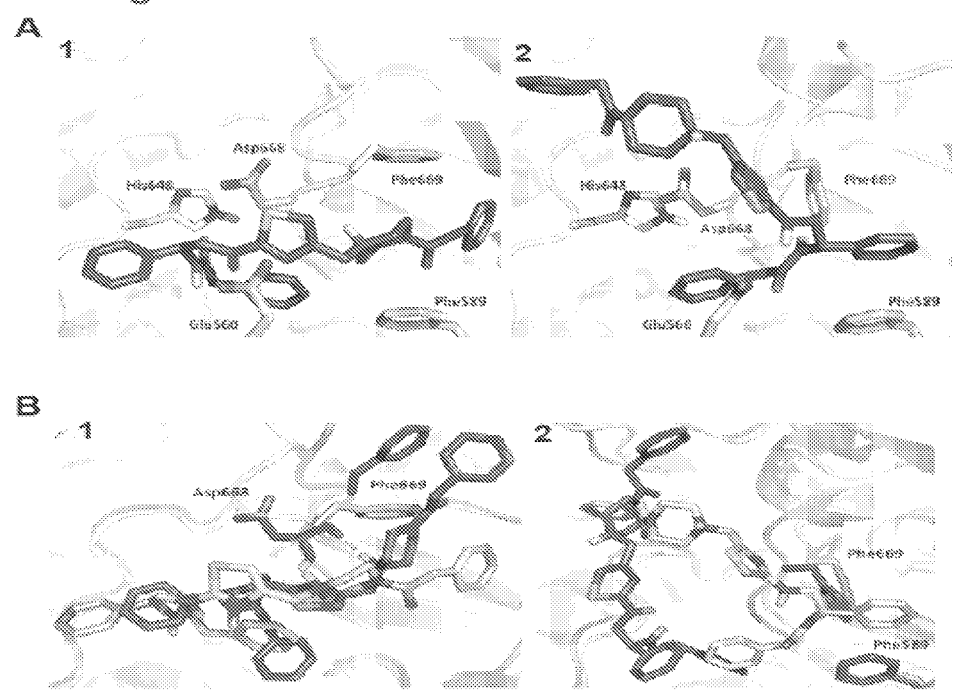
FIG. 9.5

COMPOUNDS AND METHODS OF TREATING NEUROLOGICAL DISORDERS

CLAIM OF PRIORITY TO RELATED APPLICATION

This application is the 35 U.S.C. § 371 national stage application of PCT Application No. PCT/US2015/028739, filed May 1, 2015, where the PCT claims priority to U.S. provisional application entitled "COMPOUNDS AND METHODS OF TREATING NEUROLOGICAL DISORDERS" having Ser. No. 61/987,525, filed on May 2, 2014, both of which are entirely incorporated herein by reference.

BACKGROUND

A recent report estimated that nearly 35.6 million patients are affected by Alzheimer's disease (AD) worldwide and that about 4.6 million new cases are added up each year causing tremendous economic and social burden (Wimo, A et al., 2010, *Alzheimer's Dementia* 6, 98-103). In the US alone about 5.3 million Americans are affected by AD requiring about 148 billion dollars in annual costs for the care and treatment of affected patients (*Alzheimer's Association*, 2010, *Alzheimer's Dement.* 7, 208-244). Perhaps even worse is that every sixty eight seconds a new case of AD is diagnosed and AD is also the sixth leading cause of death (*Alzheimer's Association*, 2010, *Alzheimer's Dement.* 7, 208-244). For this reason AD is considered the second most feared disease after cancer. Although in the last two decades remarkable advances have been made in understanding the biological underpinnings of AD, we have completely failed to bring even a single truly disease modifying drug for therapy (Salomone, S et al., 2012, *Br. J. Clin. Pharmacol.* 73, 504-517). So far secretase inhibitors were considered the holy grail of AD. But anti-amyloid therapy based on secretase inhibition including the most recent semagacestat (Cummings, J, 2010, *Biol Psych.* 68, 876-878; Extance, A. 2010, *Nat. rev. Drug. Discov.* 9, 749-751), homotaurine (Swanoski, M T, 2009, *Am. J. Health Syst. Pharm.* 66, 1950-1953) and tarenfurbil (Green, R C. et al. 2009, *JAMA*, 302, 2557-2564), have all failed in clinical trials due to unacceptable levels of side effects and lack of potency. Because both γ- and β-secretase substrates are involved in vital functions (Haapasalo, A and Kovacs, D M. 2011, *J. Alzheimer's Dis.* 25, 3-28; Citron, M. 2004, *Trends Pharmacol. Sci.* 25, 92-97; Cole, S L. And Vassar, R. 2007, *Mol. Neurodegen.* 2, 22-47), the reported toxicity was not unexpected. Alternative strategies that may modulate APP processing without directly inhibiting secretases are therefore the need of the hour. So, if no effective disease modifying therapy is found in near future, it is predicted that by 2050 more than 100 million individuals will have AD worldwide (Wimo, A et al., 2010, *Alzheimer's Dementia* 6, 98-103; *Alzheimer's Association*, 2010, *Alzheimer's Dement.* 7, 208-244). Thus the unmet medical need for a therapy to treat AD is enormous.

SUMMARY

Embodiments of the present disclosure provide for compositions including a compound (shown below), pharmaceutical compositions including the compound, methods of treatment of a disease or related condition (e.g., neurological disease on condition), methods of treatment using compositions or pharmaceutical compositions, and the like.

An embodiment of the present disclosure includes a composition, among others, that includes: a compound having the following structure:

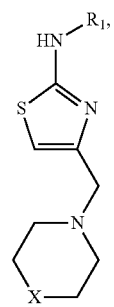

wherein X is $CR_2R_3$, $NR_4$, O, S, SO, or $SO_2$, wherein $R_1$ is selected from the group consisting of: H, a straight or branched, saturated or unsaturated, cyclic or acyclic, chiral or achiral hydrocarbyl group with up to 20 carbon atoms, where each hydrocarbyl group is optionally substituted with a hydroxyl group, an alkoxy group, an amino group, a substituted amino group, a thio group, an alkylthio group, a guanidine group, an ureido group, a heterocyclyl group, an aryl group, and a heteroaryl group, wherein $R_2$ and $R_3$ are each independently selected from the group consisting of: H, a straight or branched, saturated or unsaturated, cyclic or acyclic, chiral or achiral hydrocarbyl group with up to 20 carbon atoms, where each hydrocarbyl group is optionally substituted with a hydroxyl group, an alkoxy group, an amino group, a substituted amino group, a thio group, an alkylthio group, a guanidine group, an ureido group, a heterocyclyl group, an aryl group, and a heteroaryl group, and wherein $R_4$ is selected from the group consisting of: H, a straight or branched, saturated or unsaturated, cyclic or acyclic, chiral or achiral hydrocarbyl group with up to 20 carbon atoms, where each hydrocarbyl group is optionally substituted with a hydroxyl group, an alkoxy group, an amino group, a substituted amino group, a thio group, an alkylthio group, a guanidine group, an ureido group, a heterocyclyl group, an aryl group, and a heteroaryl group. In an embodiment, X is $CH_2$, NH, O, or

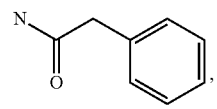

and $R_1$ is

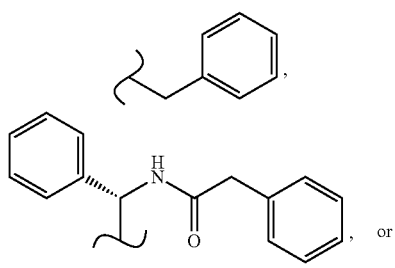

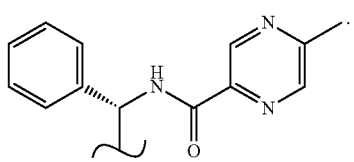

In an embodiment, the compound can have the following structure:

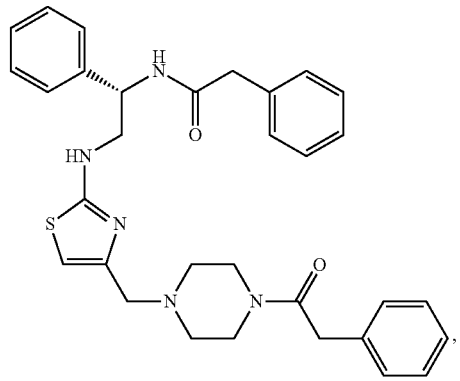 [SMILES: O=C(Cc1ccccc1)N[C@H](CNc1nc(CN2CCN(C(=O)Cc3ccccc3)CC2)cs1)c1ccccc1]

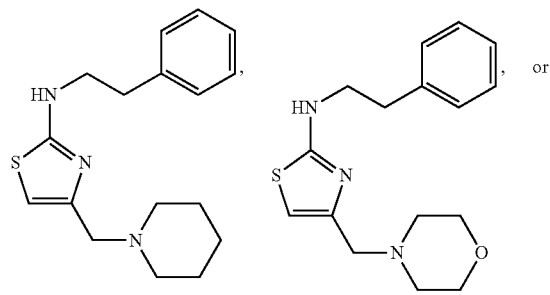

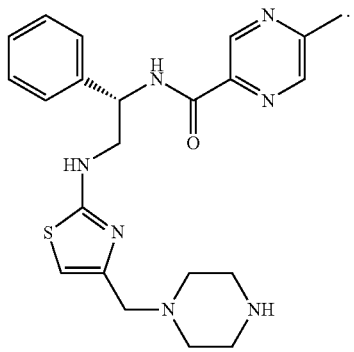 [SMILES: Cc1cnc(C(=O)N[C@H](CNc2nc(CN3CCNCC3)cs2)c2ccccc2)cn1]

An embodiment of the present disclosure includes a pharmaceutical composition, among others, that includes: a therapeutically effective amount of a compound, or a pharmaceutically acceptable salt of the compound, and a pharmaceutically acceptable carrier, to treat a disease, wherein the compound has the following structure:

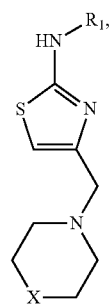

wherein X is $CR_2R_3$, $NR_4$, O, S, SO, or $SO_2$, wherein $R_1$ is selected from the group consisting of: H, a straight or branched, saturated or unsaturated, cyclic or acyclic, chiral or achiral hydrocarbyl group with up to 20 carbon atoms, where each hydrocarbyl group is optionally substituted with a hydroxyl group, an alkoxy group, an amino group, a substituted amino group, a thio group, an alkylthio group, a guanidine group, an ureido group, a heterocyclyl group, an aryl group, and a heteroaryl group, wherein $R_2$ and $R_3$ are each independently selected from the group consisting of: H, a straight or branched, saturated or unsaturated, cyclic or acyclic, chiral or achiral hydrocarbyl group with up to 20 carbon atoms, where each hydrocarbyl group is optionally substituted with a hydroxyl group, an alkoxy group, an amino group, a substituted amino group, a thio group, an alkylthio group, a guanidine group, an ureido group, a heterocyclyl group, an aryl group, and a heteroaryl group, and wherein $R_4$ is selected from the group consisting of: H, a straight or branched, saturated or unsaturated, cyclic or acyclic, chiral or achiral hydrocarbyl group with up to 20 carbon atoms, where each hydrocarbyl group is optionally substituted with a hydroxyl group, an alkoxy group, an amino group, a substituted amino group, a thio group, an alkylthio group, a guanidine group, an ureido group, a heterocyclyl group, an aryl group, and a heteroaryl group.

An embodiment of the present disclosure includes a method of treating a disease, among others, that includes: delivering to a subject in need thereof, a pharmaceutical composition, wherein the pharmaceutical composition includes a therapeutically effective amount of a compound, or a pharmaceutically acceptable salt of the compound, and a pharmaceutically acceptable carrier, to treat the disease, wherein the compound has the following structure:

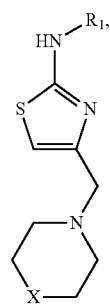

wherein X is $CR_2R_3$, $NR_4$, O, S, SO, or $SO_2$, wherein $R_1$ is selected from the group consisting of: H, a straight or branched, saturated or unsaturated, cyclic or acyclic, chiral or achiral hydrocarbyl group with up to 20 carbon atoms, where each hydrocarbyl group is optionally substituted with a hydroxyl group, an alkoxy group, an amino group, a substituted amino group, a thio group, an alkylthio group, a guanidine group, an ureido group, a heterocyclyl group, an aryl group, and a heteroaryl group, wherein $R_2$ and $R_3$ are each independently selected from the group consisting of: H, a straight or branched, saturated or unsaturated, cyclic or acyclic, chiral or achiral hydrocarbyl group with up to 20 carbon atoms, where each hydrocarbyl group is optionally substituted with a hydroxyl group, an alkoxy group, an amino group, a substituted amino group, a thio group, an alkylthio group, a guanidine group, an ureido group, a heterocyclyl group, an aryl group, and a heteroaryl group, and wherein $R_4$ is selected from the group consisting of: H, a straight or branched, saturated or unsaturated, cyclic or acyclic, chiral or achiral hydrocarbyl group with up to 20 carbon atoms, where each hydrocarbyl group is optionally substituted with a hydroxyl group, an alkoxy group, an amino group, a substituted amino group, a thio group, an alkylthio group, a guanidine group, an ureido group, a heterocyclyl group, an aryl group, and a heteroaryl group.

BRIEF DESCRIPTION OF THE DRAWINGS

Many aspects of the present disclosure can be better understood with reference to the following drawings. The components in the drawings are not necessarily to scale, with emphasis instead being placed upon clearly illustrating the principles of the disclosure. Moreover, in the drawings, like reference numerals designate corresponding parts throughout the several views.

FIG. 1.1 shows an assay (top plot) performed in full 384 well plate without test compounds. Red ovals: recombinant sAPPα control; green ovals: pharmacological control; blue circles: background. The bottom plot shows results of pilot screen against heterocycles library. Red punctured line: calculated hit cutoff (3 SD+AVE of AlphaRLU); red arrows: hits.

FIG. 1.2 illustrates an embodiment of the compound.

FIG. 1.3 illustrates immunoblot evidence for dose-dependent increase of sAPPα levels by THPI-244 in CHO cells. The top blot is a representative picture of Western blots showing increased levels of sAPPα with no change in the levels of APP-FL. ImageJ quantitation (bottom) revealed significant increase in sAPPα levels. +, $p<0.01$, $, $p<0.001$ by ANOVA (mean±SEM, n+4).

FIG. 1.4 demonstrates that THPI-244 passes through the blood-brain barrier (BBB). Top shows purity of THPI-244; middle shows standard curve used to quantitate the levels of THPI-244 in the mouse brain; bottom shows relative levels of THPI-244 in the mouse brain at different time points after i.p. administration (mean±SEM, n=4 for each time point).

FIG. 1.5 demonstrates the effect of THPI-244 on cytotoxicity in human primary neurons and AD fibroblasts. MTT assay revealed significant toxicity only at concentrations of 40 μM ($p<0.05$) for human neurons and 50 μM for AD fibroblasts by ANOVA (mean±SEM, n=4 for each dose).

FIG. 1.6 illustrates that THPI-244 (100 nM) and Bryostatin (100 nM) but not THPI-222, a structural analog of THPI-244 increases sAPPα levels dose dependently in NT2 cells stably expressing APP751. ELISA quantitation revealed significant increase starting from 10 nM (Bryostatin) and 50 nM (THPI-244). Mean±SEM, n=5. *, $p<0.05$, $, $p<0.001$ by ANOVA.

FIG. 1.7 illustrates that THPI-244 (100 nM) and Bryostatin (100 nM) but not THPI-222, a structural analog of THPI-244 decreases Aβ42 levels dose dependently in NT2 cells stably expressing APP751. ELISA quantitation revealed significant decrease starting from 10 nM (Bryostatin) and 50 nM (THPI-244). Mean±SEM, n=5. *, $p<0.05$, $, $p<0.01$ by ANOVA.

FIG. 1.8 illustrates that THPI-244 (100 nM) and Bryostatin (100 nM) but not THPI-222 increase sAPPα levels dose dependently in AD fibroblasts (top) and human primary neurons transiently expressing APP751 (bottom). ELISA quantitation revealed significant increase starting from 10 nM (Bryostatin) and 50 nM (THPI-244). Mean±SEM, n=5. *, $p<0.05$, $, $p<0.001$ by ANOVA.

FIG. 1.9 shows that THPI-244 increases TrkA receptor protein levels and phosphorylated form of both TrkA and PI3K in NT2 cells. THPI-244 did not alter either p75NTR or its down-stream targets.

FIG. 1.10 shows that THPI-244 increases sAPPα through TrkA receptors independent of PKC. Left, NT2 stable cells expressing APP751 were treated with 100 nM of THPI-244 with or without TrkA inhibitor, which prevented the increased sAPPα. Right, same cells treated with PKC inhibitor did not prevent THPI-244-induced increased TrkA protein.

FIGS. 1.11A-B show that increased dendritic arbor by THPI-244 in human primary neurons is prevented by TrkA inhibitor. In FIG. 1.11A, human neurons were seeded and treated with either vehicle, THPI-244 with or without TrkA-specific inhibitor starting from 2DIV until 6DIV. Representative fields showing robust growth of neurites in THPI-244-treated neurons (middle column) which was greatly reduced by TrkA inhibitor (third column) compared to vehicle controls. In FIG. 1.11B, Sholl analysis of dendritic intersections using ImageJ showed robust increase in THPI-244-treated neurons which was significantly prevented by TrkA inhibitor. Mean+SEM, n=30 neurons in 3 independent experiments. *, $p<0.05$, +, $p<0.01$, $, $p<0.001$ by ANOVA.

FIG. 2.1A illustrates the cleavage of APP by β-secretase leads to amyloidogenic pathway, whereas cleavage by α-secretase leads to non-amyloidogenic pathway. FIG. 2.1B illustrates the detection of the sAPPα occurs via anti-sAPPα antibodies coupled to Acceptor beads. The biotinylated anti-sAPPα is captured by streptavidin Donor beads. Irradiation of the captured reaction products triggers an energy transfer leading to light emission proportional to the release of sAPPα from 7WD10 cells.

FIG. 2.2 illustrates that 7WD10 (CHO) and NT2 (neuroblastoma) cells stably express APP751 and similarly respond to the treatment with pan-HDAC inhibitor SAHA (Vorinostat). Please note similar levels of alterations upon application of SAHA such as increased sAPPα, decreased sAPPβ and Aβ. Also levels of APP-FL are not affected.

FIGS. 2.3A-F illustrates cell number optimization and viability. Cell number effect on assay signal in (FIG. 2.3A) the presence of 10% FBS and (FIG. 2.3B) in the absence of FBS. FIG. 2.3C illustrates the cell viability test in the presence of 10% FBS and FIG. 2.3D illustrates in the absence of FBS. FIG. 2.3E illustrates 20,000 7WD10 cells/well at 4 hours after plating. FIG. 2.3F illustrates 20,000 7WD10 cells/well at 24 hours after plating. Please note that 20,000 7WD10 cells/well form monolayer in low volume 384 well plates at both time points which assures the homogeneity of interaction of cells with test compounds.

FIGS. 2.4A and B illustrate the pharmacological control compound tests. FIG. 2.4A illustrates the effect of compound concentration on release of sAPPα from 7WD10 cells: Compound 1 was tested using 20,000 cells/well in the range of 1.2-100 μM using 3-fold serial dilutions and 24 h incubation as an assay endpoint. Please note that statistically significant (*=$p<0.05$) increase of sAPPα release was observed only in wells where 100 μM of compound 1 was added either with or without FBS. FIG. 2.4B illustrates the effect of pharmacological control compound on CHO 7WD10 cell viability. Viability of cells was also tested using 20,000 cells/well in the presence of 1.2-100 μM of compound 1 to ascertain that the increase of sAPPα release is not due to excessive cell death. In the presence of 1.2-33 μM of compound 1, cells were approximately 10% less viable than untreated control either with or without FBS. 100 μM of compound 1 had a more pronounced effect on cells without FBS (~40% viability) than with FBS (~70% viability) suggesting that the assay needs to be performed in the presence of FBS.

FIGS. 2.5A and B illustrate assay performance study using whole 384 well plate. FIG. 2.5A illustrates assay performed in full 384 well plate without test compounds. Red (darker) ovals: recombinant sAPPα control; Green ovals (lighter): pharmacological control; Blue circles: background. FIG. 2.5B illustrates results of pilot screen against heterocycles library. Red punctured line: calculated hit cut-off (3SD+AVE of AlphaRLU), red arrows: hits.

FIGS. 2.6A to D illustrates ELISA evidence for increased sAPPα levels and decreased Aβ40 levels in supernatants of 7WD10 cells in presence of control compound 1. FIG. 2.6A illustrates dose-dependent increase of sAPPα levels after exposure to compound 1. Quantitation revealed significant increase in the levels of sAPPα at 100, 125, and 150 μM (=p<0.01). FIG. 2.6B illustrates dose-dependent decrease of Aβ40 levels after exposure to compound 1. Quantitation revealed significant increase in the levels of Aβ40 at 100, 125, and 150 μM (=p<0.01). Repeated measures analysis of variance (ANOVA) followed by Dunnett's post hoc test were used to find whether individual doses were significant. Data are Mean±SEM, n=4, per dose. FIG. 2.6C illustrates dose response analysis of sAPPα ELISA data. FIG. 2.6D illustrates dose response analysis of Aβ40 ELISA data.

FIGS. 3.1A-Q includes embodiments of structures of the compound.

FIGS. 4.1A-C includes analogs of TP12055-244.

FIG. 5.1 illustrates reagents to make the noted compounds (Analogs of TPI2055-244).

FIG. 6.1 illustrates compounds that can be made according to FIG. 5.1.

FIGS. 7.1A-C and 8.1A-C illustrates embodiments of structures of the compound.

FIGS. 9.1A and B illustrate that THPI-244 directly binds TrkA receptors as determined by label-free, real-time Octet Red detection system.

FIGS. 9.2A and B illustrate that THPI-244 increases TrkA and sAPPα in the mouse brain.

FIG. 9.3 illustrates THPI-244 and TrkA are colocalized at the nerve terminals as revealed by transmission electron microscopy (TEM). Immunogold labeling of mouse brain hippocampal sections confirmed colocalization of APP (20 nm gold particles, indicated by red (darker) arrow heads) and TrkA (10 nm gold particles, yellow (lighter) arrow heads) at the nerve terminals.

FIGS. 9.4A and B illustrates that THPI-244 increases TrkA dimerization in NT2 cells.

FIG. 9.5A illustrates the predicted binding modes of compound THPI-244 in the binding site of (1) 4PMP and (2) 4PMS TrkA structures. FIG. 9.5B illustrates the initial (gray (lighter)) and final (green (darker)) conformations of the compound THPI-244 inside the (1) 4PMP and (2) 4PMS structures.

DETAILED DESCRIPTION

Before the present disclosure is described in greater detail, it is to be understood that this disclosure is not limited to particular embodiments described, and the embodiment of the disclosure as such may, of course, vary. It is also to be understood that the terminology used herein is for the purpose of describing particular embodiments only, and is not intended to be limiting.

Unless defined otherwise, all technical and scientific terms used herein have the same meaning as commonly understood by one of ordinary skill in the art to which this disclosure belongs.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of pharmacy, synthetic organic chemistry, chemistry, and the like, which are within the skill of the art. Such techniques are explained fully in the literature.

The examples herein are put forth so as to provide those of ordinary skill in the art with an illustrative disclosure and description of how to perform the methods and use the compounds disclosed and claimed herein. Unless indicated otherwise, parts are parts by weight, temperature is in ° C., and pressure is at or near atmospheric. Standard temperature and pressure are defined as 0° C. and 1 atmosphere and standard ambient temperature is 25° C.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a compound" includes a plurality of compounds. In this specification and in the claims that follow, reference will be made to a number of terms that shall be defined to have the following meanings unless a contrary intention is apparent.

Definitions:

The term "substituted" refers to any one or more hydrogens on the designated atom that can be replaced with a selection from the indicated group, provided that the designated atom's normal valence is not exceeded, and that the substitution results in a stable compound. In an embodiment, one or more of the hydrogens can be substituted with a halogen (Cl, Br, I, F), an alkyl group (unsubstituted or substituted), a cycloalkyl group (unsubstituted or substituted), an aryl group (unsubstituted or substituted), and the like.

In particular, the term "substituted," as in "substituted alkyl", "substituted cycloalkyl," substituted aryl," and the like, means that the substituted group may contain in place of one or more hydrogens a group such as a halogen, an alkyl group (unsubstituted or substituted), a cycloalkyl group (unsubstituted or substituted), an aryl group (unsubstituted or substituted), and the like. In an embodiment, each R group can be substituted or unsubstituted.

The term "aliphatic group" refers to a saturated or unsaturated linear or branched hydrocarbon group and encompasses alkyl, alkenyl, and alkynyl groups, for example.

As used herein, "alkyl" or "alkyl group" refers to a saturated aliphatic hydrocarbon radical which can be straight or branched, having 1 to 20 carbon atoms, wherein the stated range of carbon atoms includes each intervening integer individually, as well as sub-ranges. Examples of alkyl include, but are not limited to methyl, ethyl, n-propyl, i-propyl, n-butyl, s-butyl, t-butyl, n-pentyl, and s-pentyl. The term "lower alkyl" means an alkyl group having less than 10 carbon atoms.

As used herein, "alkenyl" or "alkenyl group" refers to an aliphatic hydrocarbon radical which can be straight or branched, containing at least one carbon-carbon double bond, having 2 to 20 carbon atoms, wherein the stated range of carbon atoms includes each intervening integer individually, as well as sub-ranges. Examples of alkenyl groups include, but are not limited to, ethenyl, propenyl, n-butenyl, i-butenyl, 3-methylbut-2-enyl, n-pentenyl, heptenyl, octenyl, decenyl, and the like.

The term "aryl" as used herein, refers to an aromatic monocyclic or multicyclic ring system of about 6 to about 14 carbon atoms, preferably of about 6 to about 10 carbon atoms. Exemplary aryl groups include phenyl or naphthyl, or phenyl substituted or naphthyl substituted.

As used herein, "halo", "halogen", or "halogen radical" refers to a fluorine, chlorine, bromine, and iodine, and radicals thereof. Further, when used in compound words, such as "haloalkyl" or "haloalkenyl", "halo" refers to an alkyl or alkenyl radical in which one or more hydrogens are substituted by halogen radicals. Examples of haloalkyl include, but are not limited to, trifluoromethyl, trichloromethyl, pentafluoroethyl, and pentachloroethyl.

As used herein, "treat", "treatment", "treating", and the like refer to acting upon a disease. The improvement or alteration may include an improvement in symptoms or an alteration in the physiologic pathways associated with the disease. "Treatment," as used herein, covers one or more treatments of a disease in a subject (e.g., a mammal, typically a human or non-human animal of veterinary interest), and includes: treating a disease.

As used herein, the terms "prophylactically treat" or "prophylactically treating" refers completely or partially preventing (e.g., about 50% or more, about 60% or more, about 70% or more, about 80% or more, about 90% or more, about 95% or more, or about 99% or more) a disease.

The term "therapeutically effective amount" as used herein refers to that amount of an embodiment of the composition or pharmaceutical formulation being administered that will relieve to some extent one or more of the symptoms of the disease being treated, and/or that amount that will prevent, to some extent, one or more of the symptoms of the disease that the subject being treated has or is at risk of developing.

The term "unit dosage form," as used herein, refers to physically discrete units suitable as unitary dosages for human and/or animal subjects, each unit containing a predetermined quantity of a compound calculated in an amount sufficient (e.g., weight of host, disease, severity of the disease, etc.) to produce the desired effect in association with a pharmaceutically acceptable diluent, carrier or vehicle. The specifications for unit dosage forms depend on the particular compound employed, the route and frequency of administration, and the effect to be achieved, and the pharmacodynamics associated with each compound in the host.

The terms "effective amount" or "effective dose" as used herein refers to that amount of an embodiment of the present disclosure being administered to treat the disease.

By "administration" is meant introducing an embodiment of the present disclosure into a subject. Administration can include routes, such as, but not limited to, intravenous, oral, topical, subcutaneous, intraperitoneal, intraarterial, inhalation, vaginal, rectal, nasal, introduction into the cerebrospinal fluid, or instillation into body compartments can be used. A preferred route is oral administration.

As used herein, the term "subject" includes humans, mammals (e.g., cats, dogs, horses, etc.), and other living animals. In particular, the host is a human subject. Typical subjects to which embodiments of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like.

As used herein, a "pharmaceutical composition" refers to a composition, as described herein, suitable for administration to a subject, such as a mammal, especially a human. In general a "pharmaceutical composition" is sterile, and preferably free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, intravenous, buccal, rectal, parenteral, intraperitoneal, intradermal, intracheal, intramuscular, subcutaneous, inhalational and the like.

A "pharmaceutically acceptable excipient," "pharmaceutically acceptable diluent," "pharmaceutically acceptable carrier," or "pharmaceutically acceptable adjuvant" means an excipient, diluent, carrier, and/or adjuvant that are useful in preparing a pharmaceutical composition that are generally safe, non-toxic and neither biologically nor otherwise undesirable, and include an excipient, diluent, carrier, and adjuvant that are acceptable for veterinary use and/or human pharmaceutical use.

The term "pharmaceutically acceptable salts" refers to a compound of the present disclosure that can be modified by making acid or base salts thereof. Pharmaceutically acceptable salt refers to those salts that retain the biological effectiveness and optionally other properties of the free bases and that are obtained by reaction with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid, malic acid, maleic acid, succinic acid, tartaric acid, citric acid, and the like. Examples of pharmaceutically acceptable salts include, but are not limited to, mineral or organic acid salts of basic residues such as amines; and alkali or organic salts of acidic residues such as carboxylic acids.

In the event that embodiments of the present disclosure form salts, these salts are within the scope of the present disclosure. Reference to an agent of any of the formulas herein is understood to include reference to salts thereof, unless otherwise indicated. The term "salt(s)", as employed herein, denotes acidic and/or basic salts formed with inorganic and/or organic acids and bases. In addition, when an agent contains both a basic moiety and an acidic moiety, zwitterions ("inner salts") may be formed and are included within the term "salt(s)" as used herein. Pharmaceutically acceptable (e.g., non-toxic, physiologically acceptable) salts are preferred, although other salts are also useful, e.g., in isolation or purification steps which may be employed during preparation. Salts of the compounds of an agent may be formed, for example, by reacting the agent with an amount of acid or base, such as an equivalent amount, in a medium such as one in which the salt precipitates or in an aqueous medium followed by lyophilization.

Embodiments of the present disclosure that contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Embodiments of the agents that contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine, and the like.

All stereoisomers of the compounds of the composition or pharmaceutical composition of the present disclosure, such as those that may exist due to asymmetric carbons on the various substituents, including enantiomeric forms (which may exist even in the absence of asymmetric carbons) and diastereomeric forms are contemplated within the scope of this disclosure. Individual stereoisomers of the compounds of the disclosure may, for example, be substantially free of other isomers, or may be admixed, for example, as racemates or with all other, or other selected, stereoisomers. The stereogenic centers of the compounds of the present disclosure can have the S or R configuration as defined by the IUPAC 1974 Recommendations.

The term "prodrug" refers to an inactive precursor of the compounds of the composition or pharmaceutical composition of the present disclosure that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis. Harper, N. J. (1962). Drug Latentiation in Jucker, ed. Progress in Drug Research, 4:221-294; Morozowich et al. (1977). Application of Physical Organic Principles to Prodrug Design in E. B. Roche ed. Design of Biopharmaceutical Properties through Prodrugs and Analogs, APhA; Acad. Pharm. Sci.; E. B. Roche, ed. (1977). Bioreversible Carriers in Drug in Drug Design, Theory and Application, APhA; H. Bundgaard, ed. (1985) Design of Prodrugs, Elsevier; Wang et al. (1999) Prodrug approaches to the improved delivery of peptide drug, Curr. Pharm. Design. 5(4):265-287; Pauletti et al. (1997). Improvement in peptide bioavailability: Peptidomimetics and Prodrug Strategies, Adv. Drug. Delivery Rev. 27:235-256; Mizen et al. (1998). The Use of Esters as Prodrugs for Oral Delivery of β-Lactam antibiotics, Pharm. Biotech. 11, 345-365; Gaignault et al. (1996). Designing Prodrugs and Bioprecursors I. Carrier Prodrugs, Pract. Med. Chem. 671-696; M. Asgharnejad (2000). Improving Oral Drug Transport Via Prodrugs, in G. L. Amidon, P. I. Lee and E. M. Topp, Eds., Transport Processes in Pharmaceutical Systems, Marcell Dekker, p. 185-218; Balant et al. (1990) Prodrugs for the improvement of drug absorption via different routes of administration, Eur. J. Drug Metab. Pharmacokinet, 15(2): 143-53; Balimane and Sinko (1999). Involvement of multiple transporters in the oral absorption of nucleoside analogues, Adv. Drug Delivery Rev., 39(1-3):183-209; Browne (1997). Fosphenytoin (Cerebyx), Clin. Neuropharmacol. 20(1): 1-12; Bundgaard (1979). Bioreversible derivatization of drugs—principle and applicability to improve the therapeutic effects of drugs, Arch. Pharm. Chemi. 86(1): 1-39; H. Bundgaard, ed. (1985) Design of Prodrugs, New York: Elsevier; Fleisher et al. (1996). Improved oral drug delivery: solubility limitations overcome by the use of prodrugs, Adv. Drug Delivery Rev. 19(2): 115-130; Fleisher et al. (1985). Design of prodrugs for improved gastrointestinal absorption by intestinal enzyme targeting, Methods Enzymol. 112: 360-81; Farquhar D, et al. (1983). Biologically Reversible Phosphate-Protective Groups, J. Pharm. Sci., 72(3): 324-325; Han, H. K. et al. (2000). Targeted prodrug design to optimize drug delivery, AAPS PharmSci., 2(1): E6; Sadzuka Y. (2000). Effective prodrug liposome and conversion to active metabolite, Curr. Drug Metab., 1(1):31-48; D. M. Lambert (2000) Rationale and applications of lipids as prodrug carriers, Eur. J. Pharm. Sci., 11 Suppl 2:S15-27; Wang, W. et al. (1999) Prodrug approaches to the improved delivery of peptide drugs. Curr. Pharm. Des., 5(4):265-87.

The term "disease" can refer to neurological diseases such as Alzheimer's disease (AD), Parkinson's disease (PD), Huntington's disease (HD), Amyotrophic lateral sclerosis (ALS), Retinal neurodegenerative diseases such as Glaucoma, Diabetic retinopathy and Macular degeneration, and the like.

Discussion:

Embodiments of the present disclosure provide for compositions including a compound (shown below), pharmaceutical compositions including the compound, methods of treatment of a disease or related condition (e.g., neurological disease on condition), methods of treatment using compositions or pharmaceutical compositions, and the like. Embodiments of the compounds are described in the Examples. Embodiments for making the compounds are described in the Examples as well.

An embodiment of the present disclosure includes a composition and pharmaceutical composition including a compound having the following structure:

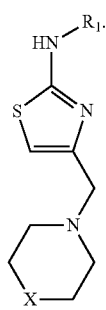

In an embodiment, X can be $CR_2R_3$, $NR_4$, O, S, SO, or $SO_2$. In an embodiment, X can be $CH_2$, NH, O, or

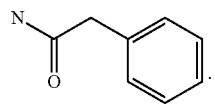

In an embodiment, $R_1$ can be a group selected from: H, a straight or branched, saturated or unsaturated, cyclic or acyclic, chiral or achiral hydrocarbyl group with up to 20 carbon atoms, where each hydrocarbyl group is optionally substituted with a hydroxyl group, an alkoxy group, an amino group, a substituted amino group, a thio group, an alkylthio group, a guanidine group, an ureido group, a heterocyclyl group, an aryl group, and a heteroaryl group. In an embodiment, R1 can be

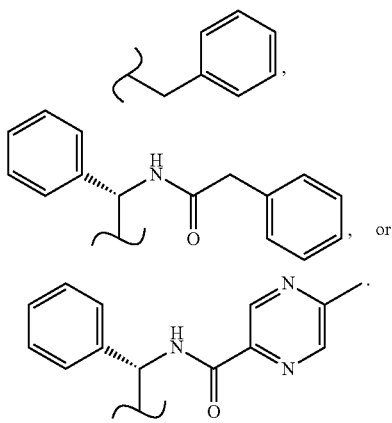

In an embodiment, $R_2$ and $R_3$ can each independently be a group selected from: H, a straight or branched, saturated or unsaturated, cyclic or acyclic, chiral or achiral hydrocarbyl group with up to 20 carbon atoms, where each hydrocarbyl group is optionally substituted with a hydroxyl group, an alkoxy group, an amino group, a substituted amino group, a thio group, an alkylthio group, a guanidine group, an ureido group, a heterocyclyl group, an aryl group, and a heteroaryl group.

In an embodiment, $R_4$ can be a group selected from: H, a straight or branched, saturated or unsaturated, cyclic or acyclic, chiral or achiral hydrocarbyl group with up to 20 carbon atoms, where each hydrocarbyl group is optionally substituted with a hydroxyl group, an alkoxy group, an amino group, a substituted amino group, a thio group, an alkylthio group, a guanidine group, an ureido group, a heterocyclyl group, an aryl group, and a heteroaryl group.

In particular embodiments, the compound can be one of the following:

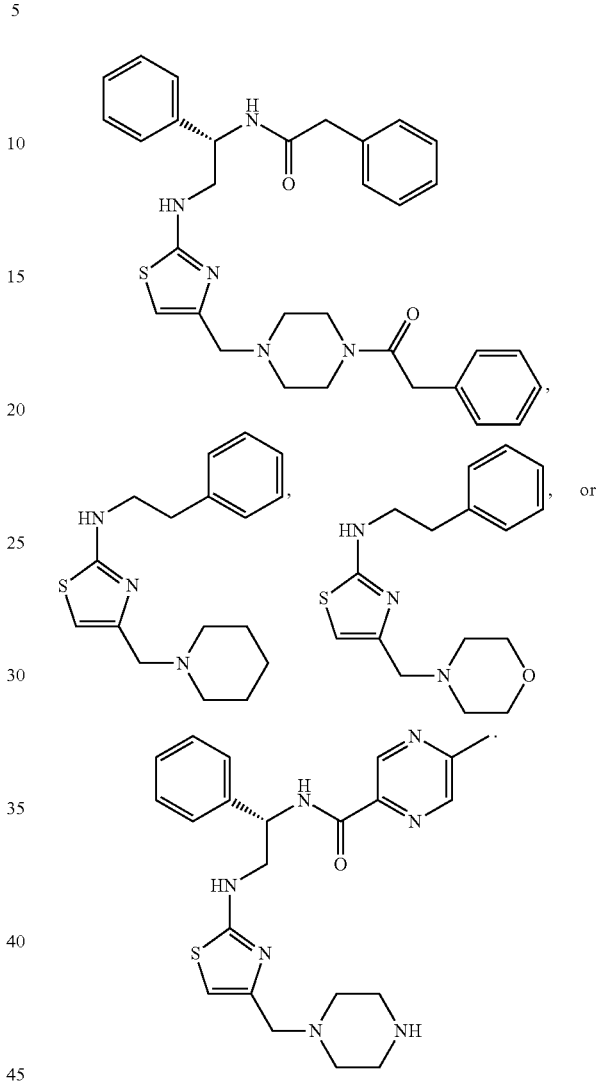

In an embodiment, the pharmaceutical composition and the method of treatment (e.g., of a disease such a neurological disease (e.g., AD)) includes a therapeutically effective amount of the compound, or a pharmaceutically acceptable salt of the compound, and a pharmaceutically acceptable carrier, to treat a disease (e.g., AD).

As mentioned above, embodiments of the present disclosure include a method of treating a disease or condition. The method can include delivering to a subject in need thereof, a pharmaceutical composition that includes a therapeutically effective amount of the compound, or a pharmaceutically acceptable salt of the compound, and a pharmaceutically acceptable carrier, to treat the disease or condition. In an embodiment, the compound can be given to the subject periodically (e.g., hourly, daily, weekly, depending upon the disease) as needed to treat the disease or condition. In addition, the compound can be given to a subject prophylactically, where the subject may have a risk of disease or condition.

It should be noted that the therapeutically effective amount to result in uptake of the compound into the subject can depend upon a variety of factors, including for example, the age, body weight, general health, sex, and diet of the host; the time of administration; the route of administration; the rate of excretion of the specific compound employed; the duration of the treatment; the existence of other drugs used in combination or coincidental with the specific composition employed; and like factors well known in the medical arts.

Pharmaceutical Formulations and Routes of Administration

Embodiments of the present disclosure include the composition containing the compound as identified herein and can be formulated with one or more pharmaceutically acceptable excipients, diluents, carriers and/or adjuvants. In addition, embodiments of the present disclosure include the compound formulated with one or more pharmaceutically acceptable auxiliary substances. In particular the compound can be formulated with one or more pharmaceutically acceptable excipients, diluents, carriers, and/or adjuvants to provide an embodiment of a composition of the present disclosure.

A wide variety of pharmaceutically acceptable excipients are known in the art. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In an embodiment of the present disclosure, the compound can be administered to the host using any means capable of resulting in the desired effect. Thus, the compound can be incorporated into a variety of formulations for therapeutic administration. For example, the compound can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

In pharmaceutical dosage forms, the compound may be administered in the form of its pharmaceutically acceptable salts, or a subject active composition may be used alone or in appropriate association, as well as in combination, with other pharmaceutically active compounds. The following methods and excipients are merely exemplary and are in no way limiting.

For oral preparations, the compound can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

Embodiments of the compound can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Embodiments of the compound can be utilized in aerosol formulation to be administered via inhalation. Embodiments of the compound can be formulated into pressurized acceptable propellants such as dichlorodifluoromethane, propane, nitrogen and the like.

Furthermore, embodiments of the compound can be made into suppositories by mixing with a variety of bases such as emulsifying bases or water-soluble bases. Embodiments of the compound can be administered rectally via a suppository. The suppository can include vehicles such as cocoa butter, carbowaxes and polyethylene glycols, which melt at body temperature, yet are solidified at room temperature.

Unit dosage forms for oral or rectal administration, such as syrups, elixirs, and suspensions, may be provided wherein each dosage unit, for example, teaspoonful, tablespoonful, tablet or suppository, contains a predetermined amount of the composition containing one or more compositions. Similarly, unit dosage forms for injection or intravenous administration may comprise the compound in a composition as a solution in sterile water, normal saline or another pharmaceutically acceptable carrier.

Embodiments of the compound can be formulated in an injectable composition in accordance with the disclosure. Typically, injectable compositions are prepared as liquid solutions or suspensions; solid forms suitable for solution in, or suspension in, liquid vehicles prior to injection may also be prepared. The preparation may also be emulsified or the active ingredient (triamino-pyridine derivative and/or the labeled triamino-pyridine derivative) encapsulated in liposome vehicles in accordance with the present disclosure.

In an embodiment, the compound can be formulated for delivery by a continuous delivery system. The term "continuous delivery system" is used interchangeably herein with "controlled delivery system" and encompasses continuous (e.g., controlled) delivery devices (e.g., pumps) in combination with catheters, injection devices, and the like, a wide variety of which are known in the art.

Mechanical or electromechanical infusion pumps can also be suitable for use with the present disclosure. Examples of such devices include those described in, for example, U.S. Pat. Nos. 4,692,147; 4,360,019; 4,487,603; 4,360,019; 4,725,852; 5,820,589; 5,643,207; 6,198,966; and the like. In general, delivery of the compound can be accomplished using any of a variety of refillable, pump systems. Pumps provide consistent, controlled release over time. In some embodiments, the compound can be in a liquid formulation in a drug-impermeable reservoir, and is delivered in a continuous fashion to the individual.

In one embodiment, the drug delivery system is an at least partially implantable device. The implantable device can be implanted at any suitable implantation site using methods and devices well known in the art. An implantation site is a site within the body of a subject at which a drug delivery device is introduced and positioned. Implantation sites include, but are not necessarily limited to, a subdermal, subcutaneous, intramuscular, or other suitable site within a subject's body. Subcutaneous implantation sites are used in some embodiments because of convenience in implantation and removal of the drug delivery device.

Drug release devices suitable for use in the disclosure may be based on any of a variety of modes of operation. For example, the drug release device can be based upon a diffusive system, a convective system, or an erodible system (e.g., an erosion-based system). For example, the drug release device can be an electrochemical pump, osmotic pump, an electroosmotic pump, a vapor pressure pump, or osmotic bursting matrix, e.g., where the drug is incorporated into a polymer and the polymer provides for release of drug formulation concomitant with degradation of a drug-impregnated polymeric material (e.g., a biodegradable, drug-impregnated polymeric material). In other embodiments, the drug release device is based upon an electrodiffusion system, an electrolytic pump, an effervescent pump, a piezoelectric pump, a hydrolytic system, etc.

Drug release devices based upon a mechanical or electromechanical infusion pump can also be suitable for use with the present disclosure. Examples of such devices include those described in, for example, U.S. Pat. Nos. 4,692,147; 4,360,019; 4,487,603; 4,360,019; 4,725,852, and the like. In general, a subject treatment method can be accomplished using any of a variety of refillable, non-exchangeable pump systems. Pumps and other convective systems are generally preferred due to their generally more consistent, controlled release over time. Osmotic pumps are used in some embodiments due to their combined advantages of more consistent controlled release and relatively small size (see, e.g., PCT published application no. WO 97/27840 and U.S. Pat. Nos. 5,985,305 and 5,728,396). Exemplary osmotically-driven devices suitable for use in the disclosure include, but are not necessarily limited to, those described in U.S. Pat. Nos. 3,760,984; 3,845,770; 3,916,899; 3,923,426; 3,987,790; 3,995,631; 3,916,899; 4,016,880; 4,036,228; 4,111,202; 4,111,203; 4,203,440; 4,203,442; 4,210,139; 4,327,725; 4,627,850; 4,865,845; 5,057,318; 5,059,423; 5,112,614; 5,137,727; 5,234,692; 5,234,693; 5,728,396; and the like.

In some embodiments, the drug delivery device is an implantable device. The drug delivery device can be implanted at any suitable implantation site using methods and devices well known in the art. As noted herein, an implantation site is a site within the body of a subject at which a drug delivery device is introduced and positioned. Implantation sites include, but are not necessarily limited to a subdermal, subcutaneous, intramuscular, or other suitable site within a subject's body.

In some embodiments, an active agent (e.g., the compound) can be delivered using an implantable drug delivery system, e.g., a system that is programmable to provide for administration of the agent. Exemplary programmable, implantable systems include implantable infusion pumps. Exemplary implantable infusion pumps, or devices useful in connection with such pumps, are described in, for example, U.S. Pat. Nos. 4,350,155; 5,443,450; 5,814,019; 5,976,109; 6,017,328; 6,171,276; 6,241,704; 6,464,687; 6,475,180; and 6,512,954. A further exemplary device that can be adapted for the present disclosure is the Synchromed infusion pump (Medtronic).

Suitable excipient vehicles for the compound are, for example, water, saline, dextrose, glycerol, ethanol, or the like, and combinations thereof. In addition, if desired, the vehicle may contain minor amounts of auxiliary substances such as wetting or emulsifying agents or pH buffering agents. Methods of preparing such dosage forms are known, or will be apparent upon consideration of this disclosure, to those skilled in the art. See, e.g., Remington's Pharmaceutical Sciences, Mack Publishing Company, Easton, Pa., 17th edition, 1985. The composition or formulation to be administered will, in any event, contain a quantity of the compound adequate to achieve the desired state in the subject being treated.

Compositions of the present disclosure can include those that comprise a sustained-release or controlled release matrix. In addition, embodiments of the present disclosure can be used in conjunction with other treatments that use sustained-release formulations. As used herein, a sustained-release matrix is a matrix made of materials, usually polymers, which are degradable by enzymatic or acid-based hydrolysis or by dissolution. Once inserted into the body, the matrix is acted upon by enzymes and body fluids. A sustained-release matrix desirably is chosen from biocompatible materials such as liposomes, polylactides (polylactic acid), polyglycolide (polymer of glycolic acid), polylactide co-glycolide (copolymers of lactic acid and glycolic acid), polyanhydrides, poly(ortho)esters, polypeptides, hyaluronic acid, collagen, chondroitin sulfate, carboxcylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. Illustrative biodegradable matrices include a polylactide matrix, a polyglycolide matrix, and a polylactide co-glycolide (co-polymers of lactic acid and glycolic acid) matrix.

In another embodiment, the pharmaceutical composition of the present disclosure (as well as combination compositions) can be delivered in a controlled release system. For example, the compound may be administered using intravenous infusion, an implantable osmotic pump, a transdermal patch, liposomes, or other modes of administration. In one embodiment, a pump may be used (Sefton (1987). *CRC Crit. Ref. Biomed. Eng.* 14:201; Buchwald et al. (1980). *Surgery* 88:507; Saudek et al. (1989). *N. Engl. J. Med.* 321:574). In another embodiment, polymeric materials are used. In yet another embodiment a controlled release system is placed in proximity of the therapeutic target thus requiring only a fraction of the systemic dose. In yet another embodiment, a controlled release system is placed in proximity of the therapeutic target, thus requiring only a fraction of the systemic. Other controlled release systems are discussed in the review by Langer (1990). *Science* 249:1527-1533.

In another embodiment, the compositions of the present disclosure (as well as combination compositions separately or together) include those formed by impregnation of the compound described herein into absorptive materials, such as sutures, bandages, and gauze, or coated onto the surface of solid phase materials, such as surgical staples, zippers and catheters to deliver the compositions. Other delivery systems of this type will be readily apparent to those skilled in the art in view of the instant disclosure.

Dosages

Embodiments of the compound can be administered to a host in one or more doses. Those of skill will readily appreciate that dose levels can vary as a function of the specific the compound administered, the severity of the symptoms and the susceptibility of the subject to side effects. Preferred dosages for a given compound are readily determinable by those of skill in the art by a variety of means.

In an embodiment, multiple doses of the compound are administered. The frequency of administration of the compound can vary depending on any of a variety of factors, e.g., severity of the symptoms, and the like. For example, in an embodiment, the compound can be administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid). As discussed above, in an embodiment, the compound is administered continuously.

The duration of administration of the compound, e.g., the period of time over which the compound is administered, can vary, depending on any of a variety of factors, e.g., patient response, etc. For example, the compound in combination or separately, can be administered over a period of time of about one day to one week, about two weeks to four weeks, about one month to two months, about two months to four months, about four months to six months, about six months to eight months, about eight months to 1 year, about 1 year to 2 years, or about 2 years to 4 years, or more.

Routes of Administration

Embodiments of the present disclosure provide methods and compositions for the administration of the active agent (e.g., the compound) to a host (e.g., a human) using any available method and route suitable for drug delivery, including in vivo and ex vivo methods, as well as systemic and localized routes of administration.

Routes of administration include intranasal, intramuscular, intratracheal, subcutaneous, intradermal, topical application, intravenous, rectal, nasal, oral, and other enteral and parenteral routes of administration. Routes of administration may be combined, if desired, or adjusted depending upon the agent and/or the desired effect. An active agent (e.g., the compound) can be administered in a single dose or in multiple doses.

Embodiments of the compound can be administered to a host using available conventional methods and routes suitable for delivery of conventional drugs, including systemic or localized routes. In general, routes of administration contemplated by the disclosure include, but are not limited to, enteral, parenteral, or inhalational routes.

Parenteral routes of administration other than inhalation administration include, but are not limited to, topical, transdermal, subcutaneous, intramuscular, intraorbital, intracapsular, intraspinal, intrasternal, and intravenous routes, i.e., any route of administration other than through the alimentary canal. Parenteral administration can be conducted to effect systemic or local delivery of the compound. Where systemic delivery is desired, administration typically involves invasive or systemically absorbed topical or mucosal administration of pharmaceutical preparations.

In an embodiment, the compound can also be delivered to the subject by enteral administration. Enteral routes of administration include, but are not limited to, oral and rectal (e.g., using a suppository) delivery.

Methods of administration of the compound through the skin or mucosa include, but are not limited to, topical application of a suitable pharmaceutical preparation, transdermal transmission, injection and epidermal administration. For transdermal transmission, absorption promoters or iontophoresis are suitable methods. Iontophoretic transmission may be accomplished using commercially available "patches" that deliver their product continuously via electric pulses through unbroken skin for periods of several days or more.

While embodiments of the present disclosure are described in connection with the Examples and the corresponding text and figures, there is no intent to limit the disclosure to the embodiments in these descriptions. On the contrary, the intent is to cover all alternatives, modifications, and equivalents included within the spirit and scope of embodiments of the present disclosure.

EXAMPLES

Example 1

In the absence of disease modifying therapy for AD, and also because of dismal outcome from the recent clinical trials using secretase inhibitors (Doody, R S. et al., 2013, *N. Eng. J. Med.* 369, 341-350), we wanted to pursue novel mechanisms of action. Multiple lines of evidences now suggest that it is not only increased Aβ, but also decreased sAPPα levels equally play critical role in the pathogenesis of AD (Jonsson, T et al., 2012; 2012, *Nature* 488, 96-99; Kaden, D. et al., 2012, *EMBO Mol. Med.* 4, 647-659; Suh, J. et al., 2013, *Neuron,* 80, 385-401). Therefore, modulation of alternative molecular targets that may increase sAPPα levels without directly altering the activities of α-, β or γ-secretases preferably through trafficking of APP is likely a viable approach. Towards this goal, we developed an HTS-compatible cell-based assay on AlphaLISA technology.

Several thiazole derivatives including benfotiamine, rosiglitazone and pioglitazone have been shown to enhance memory (Pan, X. et al., 2010, *Brain* 133, 1342-1351; Escribano, L et al., 2009, *Biochem. Biophys. Res. Commun.* 379, 406-410; Hanyu, H et al., 2009, *J. Am. Geriatr. Soc,* 57, 177-179). Thus, so far many thiazole derivatives have led to interesting therapeutic leads and drug developments including a neuroprotective agent, Riluzole for amyotrophic lateral sclerosis (Cheah, B C et al., 2010, *Curr. Med. Chem.* 17, 1942-1949). Therefore we synthesized novel derivatives of thiazoles of about 575 compounds plus we obtained more than 100 FDA approved drugs and screened them for their effect on sAPPα levels using AlphaLISA-based HTS assay. The scheme for the synthesis of thiazoles is provided herein.

(1). The pilot screen was performed using five 384 well plates. All plates exhibited Z-factor >0.5 suggesting that the assay was robust. FDA approved oncology set was screened at 10 μM final assay concentration, while thiazole derivatives were screened at 5 μM. Seven hits from thiazole derivatives were identified using Ave+3SD rule (45) as a nominal cutoff for hit determination (FIG. 1.1 (bottom)). The hits represented a novel piperazine thiazole chemotype (FIG. 1.2). None of the compounds from FDA oncology set exhibited activity in the pilot screen.

(2). To ascertain that hits identified as a result of AlphaLISA assay are not due to artifacts of the detection system, the sAPPα levels were measured by Western blots as a secondary assay downstream of primary HTS to confirm hits or discard artifacts of the AlphaLISA assay. The assay was performed using a range of concentrations of hit compounds (10-5,000 nM). A hit compound named thiazole piperazine #244 (THPI-244) and THPI-326 induced dose-dependent increase of sAPPα in supernatants of 7WD10 cells (FIG. 1.3). The 2-fold increase over untreated control cells was observed as low as 10 nM of either compound which correlated well with the AlphaLISA assay results where compounds exhibited approximately a 2-fold increase of Alpha signal at 5 μM. Since compound THPI-244 increased sAPPα levels more than THPI-326, we focused on THPI-244 for further validation.

(3). Since blood brain barrier (BBB) is the main obstacle for drug development for any CNS disorders, we first wanted to verify whether compound THPI-244 enters the brain. We followed protocols exactly as published previously from our laboratory (Hayes, C D et al., 2013, *BMC Med.* 26, 11.81). The purity of THPI-244 was verified by LC-MS and the data showed a single peak (FIG. 1.4 (top)), suggesting a high purity of the compound. We generated a standard graph (FIG. 1.4 (middle)) to be used in the quantitation of THPI-244 in the brain after intraperitoneal (i.p.) injections at 0.2 mg/kg body weight. THPI-244 entered the brain very fast and reached maximum levels within 5 min and gradually decreased up to 120 min and at 240 min only a negligible amount of THPI-244 remained in the brain (n=4 for each time point (FIG. 1.4 (bottom)). Thus although THPI-244 easily enters the brain it is also cleared modestly fast.

(4). Toxicity is another crucial limitation for successful drug development as evidenced by recent failure of γ-secretase inhibitors at the clinical trials due to cytotoxicity (Cole, S L and Vassar, R, 2007, *Mol. Neurodeg.* 2, 22-47; Doody R S, et al. 2013. *N. Eng. J. Med.* 369, 341-350). Therefore we measured cytotoxicity by very sensitive MTT assay as described previously (Hayes, C D., et al. 2013, *BMC Medicine.* 26, 11.81; 23; Hayes, C D., et al., 2012, *PLoS One* 7, e45841) in human primary neurons obtained from a commercial source (cat #1520, ScienCell, Carlsbad, Calif., USA) and fibroblasts derived directly from AD patients (cat #AG06263C, Coriell Institute Cell repository supported by NINDS, NIH). As shown in FIG. 1.5, 24 h exposure to THPI-244 resulted in significant cytotoxicity starting from only 40 μM for human neurons (n=4) and from 50 μM for human fibroblasts (n=4). We directly used human neurons for toxicity studies so as to reduce the chances of future failure at a later stage due to toxicity.

(5). To confirm the effect of THPI-244 on sAPPα levels in a neuronal cell line and by a tertiary assay, we exposed human Neuron-committed Teratocarcinoma cell line (NT2) stably expressing human APP751 to different concentrations of THPI-244 for 24 h and compared with that of Bryostatin, a classical activator of PKC known to stimulate sAPPα release. We also tested THPI-222, a structural analog of THPI-244 with a comparable molecular weight as a control. Levels of sAPPα were measured by ELISA using commercially available kit (cat #27734, IBL-America, Minneapolis, Minn., USA). NT2 cells also showed dose-dependent increase in sAPPα release and THPI-222 had no effect (FIG. 1.6). While Bryostatin increased sAPPα at low nM concentrations, but then decreased levels dose-dependently. On the other hand, THPI-244 reliably increased sAPPα release up to 2000 nM starting from 50 nM (n=4 independent experiments) (FIG. 1.6). Similar biphasic effect of Bryostatin was confirmed for Aβ42 also, measured again in NT2 stable cells by ELISA (cat #KHB3441, Life Technologies, Grand Island, N.Y., USA). Consistent with sAPPα, THPI-244 decreased Aβ42 levels dose-dependently starting from 50 nM (28%, p<0.05) to 2000 nM (64%, p<0.001) (n=4 independent experiments) (FIG. 1.7). Thus THPI-244 increased non-amyloidogenic processing of APP in NT2 cells.

Discussion:

(1). THPI-244 was directly tested in human primary neurons and fibroblasts derived from AD patients and demonstrated a therapeutic window of 800. In light of a strong disconnect from preclinical results to clinical settings, we next wanted to validate these results in human cells. Therefore, we first used fibroblasts derived from AD patients (AG06263C, Coriell Cell repository, supported by NINDS/NIH) and exposed to THPI-244 for 24 h and measured sAPPα release by ELISA as done above for NT2 cells. Interestingly, for both Bryostatin and THPI-244 the results were precisely reproduced as those for NT2 cells (n=4) (FIG. 1.8 (top)). We also confirmed dose-dependent effect of THPI-244 on sAPPα levels in human primary neurons transiently transfected with APP751 with Swedish mutation which is trafficked differently from WT APP and releases more sAPPα. Human neurons were grown on specially coated glass coverslips (cat #GG-18-PDL, NeuVitro, Germany). We could reproducibly achieve nearly 30% transfection efficiency using a nanoparticle based transfection reagent called Neuromag (cat #NM150299, OZ Biosciences, France). THPI-244 increased sAPPα levels by 171% (p<0.05) at 50 nM and by 301% (p<0.001) at 2000 nM (n=3) (FIG. 1.8 (bottom)). But because of the costs involved in procuring human neurons, we did not test the effect of Bryostatin or the structural analog.

(2). THPI-244 increases sAPPα by a novel mechanism of upregulating TrkA, a neurotrophic receptor. Therefore, in addition to increasing neuroprotective sAPPα and decreasing toxic Aβ, THPI-244 mediated increased TrkA protein levels are expected to provide neurotrophic support. Following the validation of the effect of THPI-244 in increasing sAPPα levels in CHO cells, NT2 cells, AD fibroblasts and human primary neurons, we were interested in identifying the molecular target of THPI-244 for unraveling the molecular mechanism by which it increases sAPPα which in turn can predict toxicity profile and whether to pursue long-term studies. Increased protein levels of both native and phosphorylated form of TrkA in NT2 cells and mouse brains by THPI-244 validated TrkA as the target. Further signal transduction analysis revealed that increased TrkA resulted in the activation of PI3Kα, but not MAPK or PLC-γ pathways (FIG. 1.9). However, THPI-244 did not affect P75NTR, low affinity NGF receptor that transduces cell death signals, or its downstream pathways such as JNK and NF-kB (FIG. 1.9).

(3). THPI-244 increases TrkA receptor levels independent of protein kinase C (PKC). Next to clarify whether increased sAPPα levels depends on increased TrkA activation, NT2 cells were treated with THPI-244 with or without TrkA inhibitor (cat #GW 441756, Tocris Bioscience) at 50 nM final concentration. After 24 h, sAPPα levels were quantified from the conditioned medium by immunoblots. THPI-244 treatment at 100 nM increased sAPPα levels by more than two-fold (245%, p<0.001), but to our surprise, TrkA inhibitor treatment almost completely prevented the increase (132%) (FIG. 1.10 (left)). These results confirm that THPI-244-mediated increase in sAPPα levels is due to activation of TrkA receptors. We next wanted to address whether increased TrkA protein levels by THPI-244 depends on PKC since PKC activators are well-known to induce sAPPα secretion (Etcheberringaray, R., et al., 2004, *PNAS*, 101, 11141-11146). NT2 cells were similarly treated with THPI-244 at 100 nM with or without PKC inhibitor (GF 109203, cat #0741, Tocris Bioscience) at 1.0 nM and TrkA protein levels were quantified by immunoblots as shown in FIG. 1.10 (right). THPI-244 treatment increased TrkA protein levels to 197% (p<0.001, n=4), but PKC inhibitor treatment had no effect and increased TrkA levels to 192% (p<0.001, n=4) (FIG. 1.11B), suggesting that THPI-244 increases TrkA protein levels independent of PKC. Thus increased sAPPα level by THPI-244 is through upregulation of TrkA receptor independent of PKC.

(4). The most important property of THPI-244 is its ability to increase neurite outgrowth and dendritic intersections in human primary neurons. Since both TrkA and sAPPα promote neuron growth and provide trophic support, we tested whether treatment of human primary neurons with THPI-244 induces neurite outgrowth. Neurons were exposed to the compound every day starting from 2DIV until 6DIV and simple observation by phase contrast microscope revealed robust growth of neuritic networks already by 6DIV. Considering an enormous potential for such an excellent results in human neurons, we did systematic analysis by also treating neurons in the presence of TrkA inhibitor to verify if the increased neurite outgrowth is mediated by TrkA receptor. Sholl analysis using ImageJ software of individual neurons (at least 30 per group) immunostained for MAP2 antibody confirmed our initial findings. Remarkably, there was highly significant increase in the number of dendritic intersections in the THPI-244-treated group (FIGS. 1.11A & B). More importantly, TrkA inhibitor almost completely prevented the increased intersections. This confirmed that THPI-244 increases TrkA protein levels which has vital role in regulating neuritic outgrowth.

So far, more than 500 clinical trials have failed to bring an effective therapy for AD. Most failures are due to either lack of efficacy in human or unacceptable levels of toxicity. Since THPI-244 increases two powerful neurotrophic factors such as sAPPα and TrkA receptor levels, THPI-244 is expected to provide strong neurotrophic support to the degenerating neurons in the AD brain. Additionally, since THPI-244 reduces toxic Aβ, it is also expected to reduce amyloid plaques and reverse memory deficits. Also, THPI-244 does not affect any of the secretases and therefore the plethora of side effects attributed to secretase inhibition will be completely absent from THPI-244. Moreover, THPI-244 has powerful effect in promoting neurite outgrowth in human neurons, which is also expected to reverse synaptic damage prevalent in AD brains.

Example 2

Starting from p-methylbenzhydrylamine hydrochloride (MBHA.HCl) resin; we developed different approaches toward the diversity oriented solid-phase parallel synthesis of different aminothiazole compounds 1-6 (Scheme 1) (Micheals, H A et al., 2014, *ACS Comb. Sci.* 16, 1-4; Nefzi, A et al., 2010, *J. Org. Chem.* 75, 7939-7941). 575 thiazole compounds were synthesized and were tested for sAPPα increasing activity using CHO cells stably expressing APP751wt. For initial screenings we used a cell-based human sAPPα ELISA kit (cat #27734, IBL Co., ltd, Japan) following instructions from the manufacturer. The method involves sandwich ELISA and use of two specific antibodies and tetra methyl benzidine as a coloring agent. We used previously generated CHO cells stably expressing APP751wt (7WD10 cells) for the secretion of sAPPα and Aβ in to the conditioned medium (CM). We first optimized the protocol for our cell culture conditions.

Scheme 1

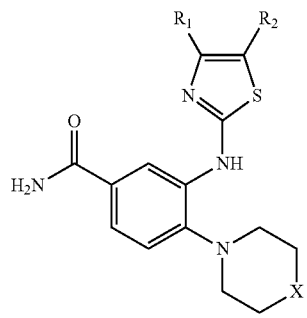

X = O, N 16 compounds

-continued

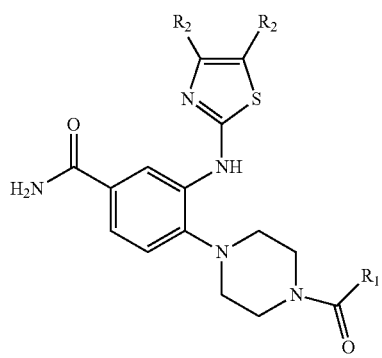

40 compounds

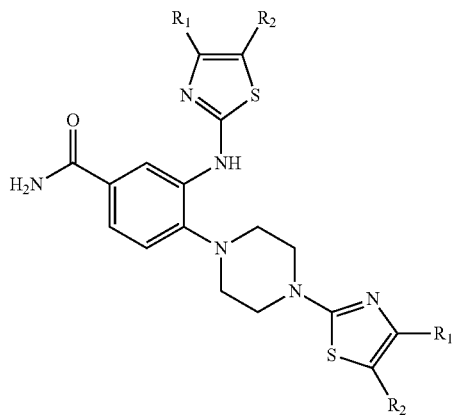

14 compounds

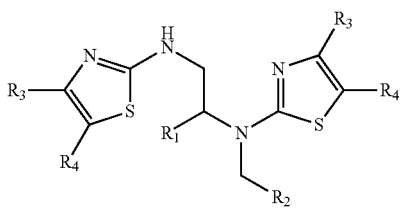

60 compounds

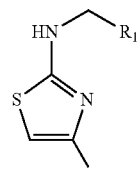

240 compounds

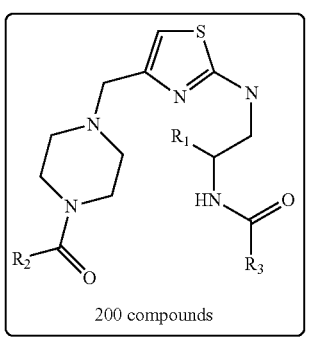

200 compounds

Among about 575 compounds tested, four compounds derived from the same class of thiazole tethered piperazine (THPI) showed promising activity by increasing sAPPα levels and reducing secretion of Aβ peptides in to the conditioned medium (Scheme 2). The most active compound THPI-244 robustly increases sAPPα levels in neuronal cell lines, human primary neurons as well as fibroblasts derived directly from patients with AD. Further, using DARTS as a novel drug target identification method, we also discovered that THPI-244 increases sAPPα levels by increasing levels of TrkA, a high affinity NGF receptor which exerts neurotrophic support, without altering p75NTR, which is generally linked to cell death. Interestingly, no compound has been tested in clinical trials that increase sAPPα by up regulating TrkA protein levels. Thus we have proposed to study THPI-244 with a novel mechanism of action. Because sAPPα is neuroprotective and TrkA signaling provides neurotrophic support, it is very likely that THPI-244 will be very safe in human, unlike the secretase inhibitors.

Scheme 2

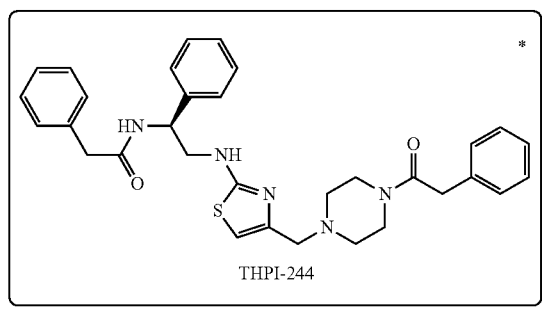

THPI-244

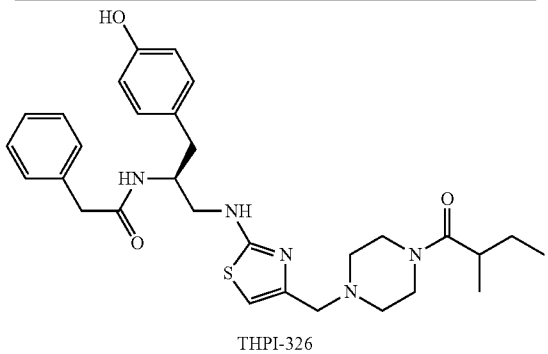

THPI-326

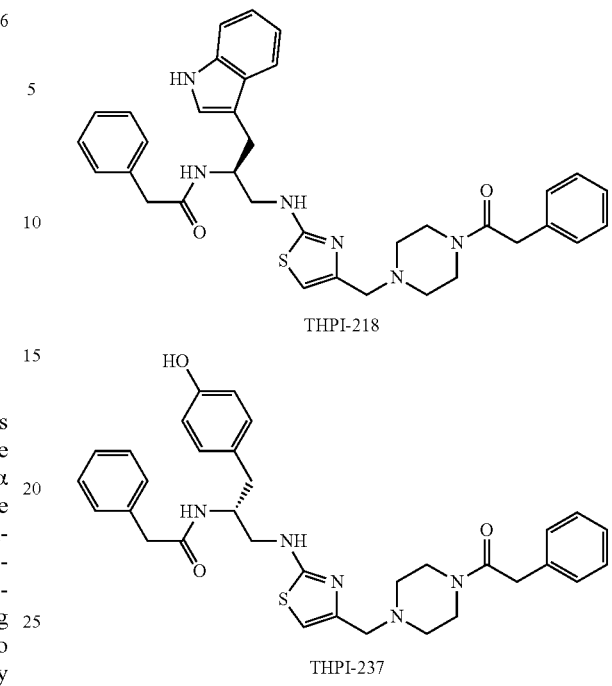

THPI-218

THPI-237

The THPI class of compounds was synthesized following the strategy outlined in Scheme 3. Starting from resin bound amino acid, the amide bond was reduced in the presence of BH$_3$-THF (Nefzi, A et al., 2006, *Bioorg. Med. Chem. Lett.* 16, 4331-4338; Nefzi, A et al., 2004, *J. Org. Chem.* 69, 3603-3609) and the primary amine was selectively protected with Trt-Cl. The treatment of resin-bound protected diamines with Fmoc-isothiocyanate generated thiourea, which was treated with a 1,3-dichloroacetone to afford the resin bound chloromethyl aminothiazole. The chloro group was displaced with freshly prepared Fmoc piperazine, and the Fmoc protecting group was deprotected with piperidine in DMF. The generated free piperazine was acylated with a variety of commercially available carboxylic acids. The Trt group was deprotected in the presence of 2% TFA in DCM and the generated primary amine was acylated with different carboxylic acids to afford following cleavage of the solid support the corresponding aminothiazole thethered piperazine derivatives (THPI). We performed the parallel synthesis of 200 individual compounds.

Scheme 3: (a) Trt—Cl in DMF, (b) BH$_3$—THF, (c) FmosNCS in DMF, (d) 1.3-dichloroacetone, (e) piperazine in DMF, (f) Piperidine in DMF, (g) R$_2$COOH, DIC, (h) 2% TFA in DCM, (i) R$_3$COOH, DIC, (j) HF/anisole.

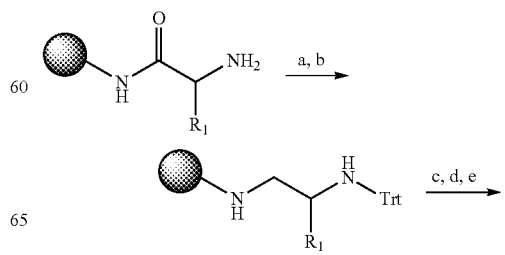

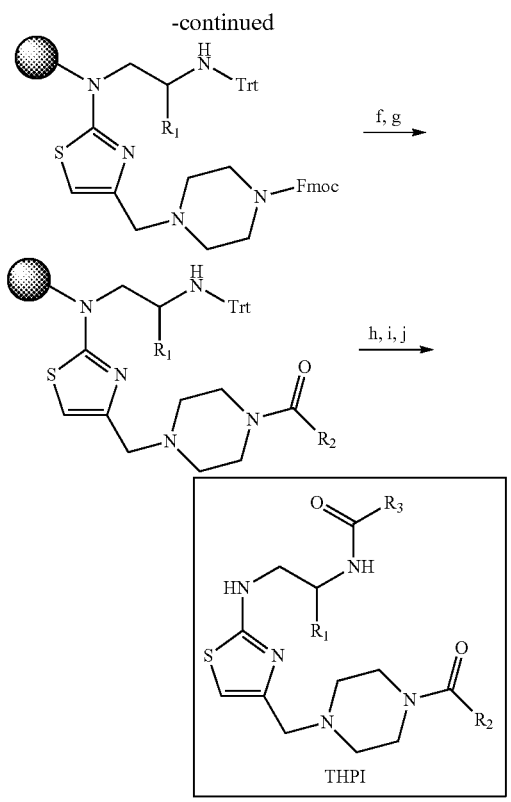

for 30 min and the resin was washed three times with DCM and neutralized with a solution of 5% DIEA in DCM. The resin bound amino acid was reduced in the presence of $BH_3$-THF. Typical reaction conditions consist of the treatment of resin-bound amide with 1M solution of the complex $BH_3$-THF in THF (40 eq) for 72 h at 65° C. The generated resin-bound complexed borane-amines were disproportioned by transamination following overnight treatment of the solid-support complex with neat piperidine at 65° C. The primary amine was selectively protected with Trt-Cl (15 eq) in DMF. The treatment of resin-bound protected diamines with Fmoc-isothiocyanate (6 eq) in DMF anhydrous generated the corresponding resin-bound Fmoc protected thiourea. Following Fmoc deprotection with a solution of 20% piperidine in DMF for 10 min (2 times) and resin wash with DMF (5 times), the free thiourea was treated with a 1,3-dichloroacetone (10 eq) in DMF overnight at 85° C., to afford the resin bound chloromethyl aminothiazole. The chloro group was displaced with piperazine (10 eq) in DMF overnight, and the free amine of the piperazine was acylated with a variety of commercially available carboxylic acids (10 eq) in DMF in the presence of DICI overnight. The Trt group was deprotected in the presence of 2% TFA in DCM and the generated primary amine was acylated with different carboxylic acids (10 eq) in DMF in the presence of DICI overnight to afford, following cleavage of the solid support with anhydrous HF for 90 min the corresponding aminothiazole thethered piperazine derivatives (TPI-2055). Embodiments of this scheme can be used to make other compounds disclosed herein.

Scheme 1: (a) Trt——Cl in DMF, (b) $BH_3$——THF, (c) FmosNCS in DMF, (d) 1.3-dichloroacetone, (e) piperazine in DMF, (f) Piperidine in DMF, (g) $R_2COOH$, DIC, (h) 2% TFA in DCM, (i) $R_3COOH$, DIC, (j) HF/anisole.

Example 3

Studies on Compound THPI-244 to Identify Lethal Dose, 50 (LD50) in Mice:

Wild-type (WT) C57BL/6 mice aged about 6 months were used in the study. The compound THPI-244 was initially dissolved in 100% DMSO and then diluted to final 10% DMSO with phosphate buffered saline (PBS). Injection of compound THPI-244 to 6 mice at 100 mg/kg body weight by intraperitoneal (i.p.) route did not result in the death of any of the 6 mice (monitored for 5 days). Among these 6 mice, 3 mice received repeated injections (i.p) of compound THPI-244 for 5 days. None of the mice showed any lethal effect. A single mouse was given an injection of compound THPI-244 at 200 mg/kg body weight and survived without visible ill effects. Although these results are preliminary, the study does indicate that compound THPI-244 can be injected at elevated doses to achieve the desired biological effects.

Example 4

The TPI-2055 class of compounds was synthesized following the general strategy outlined in Scheme 1. Starting from p-methylbenzhydrylamine hydrochloride (MB-HA.HCl) resin (CHEM-IMPEX INTERNATIONAL 1.15 mequiv/g, 100-200 mesh, 1% DVB), the resin was neutralized following treatment with a solution of 5% diisopropylethylamaine (DIEA) in DCM. Boc-aminoacid (6 eq) was coupled in the presence of diisopropylcarbodiimide (DICI) (6 eq) and hydroxybenzotriazole (HOBt) (6 eq) in DMF for 60 min. The completion of the coupling was monitored by Kaiser (Ninhydrin) test. The Boc group was deprotected with a solution of 55% trifluoroacetic acid (TFA) in DCM

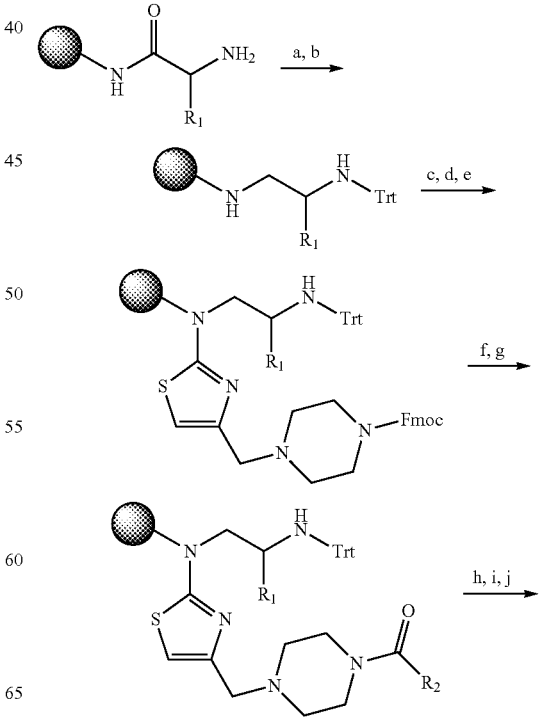

-continued

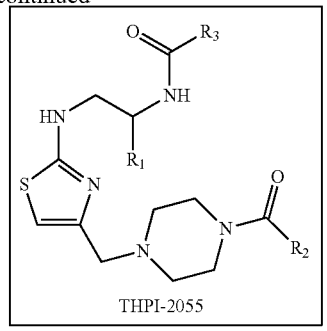

THPI-2055

Example 5

Activation of non-amyloidogenic processing of amyloid precursor protein (APP) has been hypothesized to be a viable approach for Alzheimer's disease drug discovery. However, until recently, the lack of HTS-compatible assay technologies precluded large scale screening efforts to discover molecules that potentiate non-amyloidogenic pathways. We have developed an HTS-compatible assay based on AlphaLISA technology that quantitatively detects soluble APPα (sAPPα), a marker of non-amyloidogenic processing of APP, released from live cells in low volume, 384 well plates. The assay exhibited good QC parameters (Z'>0.5, S/B>2). A pilot screen of 801 compounds yielded a novel chemotype that increased the release of sAPP$_\alpha$ 2-fold at 5 µM. These results suggest that the AlphaLISA-based HTS assay is robust and sensitive and can be used to screen large compound collections to discover molecules that potentiate the release of sAPP$_\alpha$. Additionally, we demonstrated that increase of APP processing by non-amyloidogenic pathway will result in decrease of release of amyloidogenic Aβ40 fragments.

Introduction:

Alzheimer's disease (AD) is an age-dependent disease that affects memory and cognitive functions of the patients to an extent that they are completely dependent on nursing care. AD affects approximately half of the elderly population over age 85 and more than 4 million people in the United States are already diagnosed with AD. The main theory of AD pathogenesis is the so-called "amyloid hypothesis" whereby the increased processing of amyloid precursor protein (APP) into amyloid β peptide (Aβ) by β-secretase and γ-secretase complex leads to formation of senile plaques [1]. One of the strategies to treat AD is to prevent formation of Aβ and senile plaques [2]. This, hypothetically, can be achieved by either inhibiting the enzymes responsible for formation of Aβ and senile plaques [3-6] or by activating a non-amyloidogenic pathway of APP processing [7]. The non-amyloidogenic pathway involves the cleavage of APP by so called α-secretase within the Aβ sequence which precludes Aβ formation and releases APP fragment (soluble APPα, sAPPα) that has neurotrophic and neuroprotective properties (FIG. 2.1A) [8].

Inhibition of β- and γ-secretases has been an area of active research by many pharmaceutical companies [4, 5]; however, this approach has proven to be problematic. Inhibitors of γ-secretase BACE-1 typically are not selective for BACE-2 and also inhibit hydrolysis of other cognate substrates of BACE-1 important for normal function [9], which results in unwanted side effects. Similarly, inhibitors of APP cleavage by γ-secretase also inhibit hydrolysis of Notch, which also leads to the interruption of basic biological functions [10, 11]. So far, no inhibitors of β- and γ-secretase have been approved for AD therapy [12].

An alternative approach that has been increasingly discussed in the recent literature is based on activation or induction of non-amyloidogenic processing of APP [1, 8, 9, 13]. There, however, have not been any reports of high-throughput screening efforts to discover small molecules that increase non-amyloidogenic processing of APP. Western blotting has been used to perform low throughput characterization of potential activators of non-amyloidogenic processing of APP [2], but there are no publications describing an HTS-amenable assay to detect the levels of sAPPα in a cell-based setting.

Historically, ELISA or some variation thereof has been the main technique to detect and quantify biomolecules in biological fluids [14]. ELISA requires a transfer of supernatant from the culture plate/flask to the ELISA plate followed by several wash steps, which violates the main requirement of high-throughput screening of "addition only" workflow. Recent introduction of AlphaLISA technology as an alternative to ELISA has enabled development of many assays to detect and quantify biological analytes in an HTS-friendly assay format [14-27]. AlphaLISA offers several advantages over ELISA [14], primarily the "addition only" no-wash format. Presently, we report the development of an HTS assay to identify molecules that increase the release of sAPPα from live cells.

Materials and Methods.

Reagents. Soluble APPα AlphaLISA detection kit was from Perkin-Elmer (cat #: AL254C) ProxiPlate Plus-384 HS grey plates (cat #6007290) were from Perkin Elmer. CHO cells stably expressing APP holoprotein (APP751, 7WD10 cells) were generated as described previously [28, 29]. Pharmacological assay control (2,6-dichloro-N-{2-[(3-chlorobenzyl)thio]ethyl}benzamide) was from Chembridge (cat #: 5538506). DMEM was from Corning (Cat #: MT-10-013-CV). FBS was from Biowest (Cat#: 501520H1). 100× Penicillin/Streptomycin Solution (10,000 I.U./mL Penicillin and 10,000 µg/mL Streptomycin) was from Corning Cellgro (Cat#: 30-002-CI). FDA approved oncology drugs set was from the National Cancer Institute Developmental Therapeutics Program (NCI-DTP).

Pilot screen of AlphaLISA sAPPα release assay [30]. 8 µL of assay media (DMEM supplemented with 10% FBS and 1× Penicillin/Streptomycin) containing 20,000 cells were added to all wells of the assay plate, except column 1 where only media was added. Plates were incubated for 4 h at 37° C., 5% $CO_2$, 95% RH after which 80 nL of test compounds in DMSO or DMSO alone were added to respective wells using a pin tool device (VP Scientific, San Diego). After 24 h of incubation at 37° C., 5% $CO_2$, 95% RH, sAPPα AlphaLISA beads were added in 10 µL of buffer, equilibrated for 1 h, and AlphaLISA signal was measured using a Biotek H4 Synergy microplate reader (Biotek Inc). Three parameters were calculated on a per-plate basis: (a) the signal-to-background ratio (S/B); (b) the coefficient for variation [CV; CV=(standard deviation/mean)×100)] for all compound test wells; and (c) the Z'-factor [31]. Nominally active compounds from the pilot screen were determined using mean plus 3 times the standard deviation (Mean+3SD) was used as the cut-off [32].

Western blot sAPPα release assay. 7WD10 cells were grown in 6-well plates and treated with test compounds and SAHA (vorinostat) at several concentrations in duplicate wells. After 24 h of drug exposure, the conditioned media (CM) was collected, centrifuged to remove cell debris and subjected to SDS-PAGE electrophoresis. sAPPα (6E10, mouse IgG from IBL America ltd) was detected using indicated antibody. To detect APP-FL holoprotein and C-terminal fragments (CTFs, CT15 antibody), the cells were lysed using lysis buffer (1% NP40) with complete protease inhibitor mix (Sigma) supplemented with sodium vanadate and microcystine. Samples were subjected to SDS-PAGE, transferred and immunoblotted with indicated antibodies and detected by enhanced chemiluminescence method. Quantification of Western blot signals was done using ImageJ software.

sAPPα and Aβ40 release ELISA assay. 7WD10 cells stably expressing APP751 were used for the detection of sAPPα in the conditioned medium (CM). For the detection of sAPPα, human sAPPα assay kit from IBL (Immuno-Biological Laboratories Co., Ltd, cat #27734) was used. The kit is a solid phase sandwich ELISA using two different antibodies. The principle of the method is based on the use of tetra methyl benzidine (TMB) as a chromogen and the strength of the generated color is proportional to the quantities of human sAPPα. Briefly, cells were grown in 6-well plates and treated with compound 1 at 0, 50, 75, 100, 125 and 150 μM final concentrations. After 24 hours of compound exposure, the CM was collected, centrifuged to remove cell debris and used in the assay. 100 μL of EIA buffer was used as blank. The 100 μL of test samples were put in to each well and incubated the precoated plate overnight at 40 C covered with plate lid. After overnight incubation, wells were vigorously washed with wash buffer several times. Then 100 μL of labeled antibody was added, incubated at 40 C for 30 minutes and washed again several times. Plates were incubated with chromogen solution for 30 minutes, and read at 450 nm after adding stop solution. Levels of Aβ40 in the CM treated with different concentrations of compound 1 as detailed above were measured by sandwich ELISA exactly as described previously [33]. Aβ40 was captured with Ab9 antibody (epitope, 1-16 of Aβ40) and detected with horseradish peroxidase-conjugated Ab13.1.1 antibody (epitope, 35-40 of Aβ40).

Statistics. Since the experiment involved testing the effect of one dose-response, we used one-way analysis of variance (ANOVA) followed by Tukey-Kramer or Dunnett post hoc test to find whether individual doses were significant. The data shown are the mean+SEM, n=6 per group from 3 independent experiments.

Cell viability assay. 7WD10 cells were plated in 384-well plates in 8 μL of media. Plates were incubated for 4 and 24 h at 37° C., 5% $CO_2$ and 95% RH. After incubation, 8 μL of CellTiter-Glo® (Promega cat #: G7570) were added to each well, and incubated for 15 min at room temperature. Luminescence was recorded using a Biotek Synergy H4 microplate reader. Viability is expressed as a % relative to wells containing media only (0%) and wells containing cells (100%).

Results and Discusssion
Development of sAPPα Release Assay Using AlphaLISA Detection Kit.

We utilized a commercially available AlphaLISA detection kit to develop an HTS assay for identification of compounds that increase sAPPα production in CHO cells stably expressing APP751 (7WD10 cells) (FIG. 2.1B). There are several cell lines that have been used extensively in Alzheimer's disease research. For example, NT2 cells are highly used in AD basic and drug discovery research [34-37] because they are derived from a human embryonal carcinoma cell line and they can be differentiated into post-mitotic neuron-like cells [38] that develop functional dendrites and axons resembling primary neurons of the human brain [39]. NT2 cells also synthesize amyloid precursor protein important in Alzheimer's disease [40]. However, the rate of growth of NT2 cells is much slower than rate of growth of 7WD10s cells, which makes them less HTS-amenable. We have analyzed both 7WD10 and NT2 cells for expression of the hallmark proteins of Alzheimer's disease: soluble APPα, soluble APPβ, Arβ, and membrane-bound full length APP (APP-FL). NT2 and 7WD10 cells exhibited similar levels of above-mentioned proteins (FIG. 2.2, vehicle). Since it was shown that broad HDAC inhibition results in a decrease of AR and an increase of soluble APPα [41] we tested both cell lines for the effect of application of SAHA (suberoylanilide hydroxamic acid or vorinostat), a pan-HDAC inhibitor [42]. As can be seen in FIG. 2.2, consistent with effect reported in the literature, SAHA application resulted in decrease of Aβ, sAPPIβ and an increase of soluble APPα in case of both cell lines. This suggested that 7WD10 cells represent a suitable model for the discovery of small molecules that can increase the release of soluble APPα.

To determine the number of cells and time necessary to obtain a robust signal, the range of 7WD10 cell concentrations from 1,250 to 50,000 cells/well (±FBS) was tested over the period of 72 h. 1,250-10,000 cells/well did not produce signal statistically different from wells containing only media (data not shown) at any time point. In the range of cell concentrations between 20,000 and 50,000 cells/well robust signal was obtained. In the case of cells plated in 10% FBS at 24 and 48 h time points cells exhibited a concentration dependent increase of signal which was approximately 2-4-fold greater than media only wells (FIG. 2.3A). At 72 h time point, signal-to-basal increased approximately 10-15-fold as compared to media-only wells, while all cell concentrations appeared to produce similar signal, which suggested that plateau was reached in the ability of cells to produce sAPPα. When cells were plated without FBS somewhat higher signal-to-basal ratios were observed at 24 and 48 h as compared to cells plated in 10% FBS; however, no change in signal was observed between 48 and 72 h (FIG. 2.3B), which suggested either loss of cell viability or inability of cells to produce more of sAPPα after 48 h of incubation without FBS. Since we were interested in developing an assay capable of measuring an increase of production of sAPPα upon addition of test compounds as compared to constitutive levels, we chose 24 h as an assay endpoint for further development. To ascertain cell viability, the CellTiter-Glo® viability assay was performed at 4 and 24 h after cell plating with and without FBS. Cells plated in 10% FBS exhibited 2-3-fold higher levels of ATP production at each cell concentration. There was little change in cell viability from 4 to 24 hours at 20,000 and 30,000 cells/well for either 10% or 0% FBS. 50,000 cells/well exhibited significant (>75%) loss of viability at the 24 h time point for either 10% or 0% FBS condition (FIGS. 2.3C and D) suggesting that an assay can be developed to be run with or without FBS if cells/well number does not exceed 30,000.

Additionally, using microscopy we visually examined 7WD10 cells plated at 20,000 cells/well in 8 μL volume in 384 low volume plates at 4 and 24 hours after seeding. Since the plates in which AlphaLISA assay is performed (Proxi-Plate Plus-384 HS grey plates cat #6007290) are opaque we had to use plates of similar well geometry and volume with clear bottom (Greiner cat #788091) to enable microscopy. As can be seen from FIGS. 2.3E and F, respectively, 7WD10 cells form a monolayer at both time points suggesting that are not over-confluent and can be utilized for HTS.

In the absence of known pharmacological agents capable of inducing an increase of sAPPα release, we tested a small molecule (FIG. 2.4A insert, compound 1 in [2]) shown to decrease Aβ release [2]. It was shown that decrease of Aβ release could be accompanied by the increase of soluble APPα, which has a neuroprotective effect [43]. Compound 1 was tested using 20,000 cells/well in the range of 1.2-100 µM using 3-fold serial dilutions and 24 h incubation as an assay endpoint. Increase of sAPPα release was observed only in wells where 100 µM of compound 1 was added either with or without FBS (FIG. 2.4A). Viability of cells was also tested in the presence of 1.2-100 µM of compound 1 to ascertain that the increase of sAPPα release is not due to excessive cell death. Consistent with the above described results, cells were less viable in the absence of FBS. In the presence of 1.2-33 µM of compound 1, cells were approximately 10% less viable than untreated control either with or without FBS (FIG. 2.4B). 100 µM of compound 1 had a more pronounced effect on cells without FBS (~40% viability) than with FBS (~70% viability) suggesting that the assay needs to be performed in the presence of FBS.

Pilot screen. To test the assay performance and amenability to HTS, the assay was performed using a full 384 well plate. All reagents were dispensed using a 16-channel pipettor, and DMSO and test compounds were delivered using a 384 pin tool device. To estimate assay scatter and possible environmental effects the assay was performed first with the addition of DMSO in place of test compounds. Preliminary testing demonstrated a lack of effect of 1% DMSO either on sAPPα response or cell viability with and without pharmacological control present (data not shown). Several types of controls were utilized to enable calculation of assay QC parameters. Column 1 and 24 contained wells (n=16) with media only (no cells present, i.e., background) to control for non-specific signal (FIG. 2.5A, blue ovals). Columns 2 and 23 contained 2 types of controls: pharmacological (compound 1, n=8) and recombinant sAPPα (n=8) (FIG. 2.5A, green and red ovals, respectively). The pharmacological control is useful to ascertain that the physiology of cells does not change unexpectedly during the HTS campaign and cells can still be induced by small molecules to increase the release of sAPPα. Recombinant sAPPα is used to ascertain that the level of sAPPα in the supernatant remains constant from plate to plate, that is it is not being degraded by proteases or endocytosed. It also serves as an additional assurance that the assay can detect higher levels of sAPPα in the case that some compounds induce release of sAPPα at levels greater than compound 1. Finally, all wells in columns 3-22 contained cells, 1% DMSO, and AlphaLISA beads (i.e., sample field, n=320).

Visual examination of the assay scattergram in the 384 well plate (FIG. 2.5A) did not reveal excessive scatter or environmental effects (e.g., "edge effect", dispense patterns, etc.). The ratio (S/B) between signal in background wells and wells with compound 1 was 12.9 with Z-factor=0.5. S/B between signal in background wells and wells with recombinant sAPPα was 35 with Z-factor=0.68. S/B between signal in background wells and sample field (columns 3-22) was 4.9 with Z-factor=0.53. Z-factor≥4 is generally considered acceptable for cell-based HTS assays. In the case of our assay, despite the manual addition mode, the Z-factor was above 0.5, which suggested a statistically significant separation between signal and noise and assay's readiness for preliminary screening.

To evaluate the ability of the assay to identify compounds that increase the release of sAPPα a pilot screen was conducted using FDA approved oncology set (n=101) and TPIMS heterocycles library (n=700). The pilot screen was performed using five 384 well plates. All plates exhibited Z-factor>0.5 suggesting that the assay is robust. FDA approved oncology set was screened at 10 µM final assay concentration, while TPIMS heterocycles library was screened at 5 µM final assay concentration. Seven hits from TPIMS heterocycles library were identified using mean plus 3 times the standard deviation (µ+3SD) as the cut-off for hit determination [32] (FIG. 2.5B). The hits represented a novel piperazine thiazole chemotype. None of the compounds from FDA oncology set exhibited activity in the pilot screen. Based on the combined FDA+TPIMS heterocycles library screen ($n_{total}$=801 compounds) the hit rate is 0.87%, which is comparable to hit rates reported in the literature [44].

To ascertain that AlphaLISA assay results are not due to artifacts of the detection system, the sAPPα release ELISA-based assay was performed using a range of concentrations of control compound 1 (50-150 µM). The 2-fold increase over untreated control cells was observed at 100 µM of compound 1 (FIG. 2.6A) which was consistent with 2-fold increase of AlpIaLISA signal observed during assay development (FIG. 2.4) and pilot screen (FIG. 2.5). The maximal effect was 3-fold increase observed at 150 µM of compound 1. Aβ40 supernatant levels were decreased by 24, 43, and 49% at 100, 125, and 150 µM of compound 1, respectively (FIG. 2.6B). ELISA data were fitted to a sigmoidal equation and dose response analysis was conducted. For sAPPα ELISA, $R^2$ value of 0.945 and Hill Slope value of 0.77 suggested good fit to a sigmoidal model (FIG. 2.6C). Aβ40 ELISA exhibited steeper Hill Slope (−4.7), however $R^2$ value was 0.977. Testing of higher concentrations of compound 1 was not conducted due to increase of compound 1 effect on cell viability. These results suggest that our initial hypothesis that activation or induction of non-amyloidogenic processing of APP will lead to the decrease of release of amyloidogenic Aβ40 was correct [1, 8, 9, 13].

In conclusion, we have developed an HTS-amenable assay to discover molecules that increase the release of sAPPα in the presence of live 7WD10 cells. The assay exhibited acceptable QC parameters despite the manual reagent addition suggesting that it can be successfully automated. The pilot screen against a small collection of drug-like heterocyclic molecules yielded several hits that were confirmed by an orthogonal assay format (data not shown) suggesting that the HTS assay is sensitive and suitable for the discovery of molecules that increase the release of sAPPα. Additionally, using compound 1 we demonstrated that increase of APP processing by non-amyloidogenic pathway will result in decrease of release of amyloidogenic Aβ40 fragments. Our future studies will be focused on automation of this assay and screening large compound collections to discover molecules that potentiate a non-amyloidogenic pathway of APP processing.

REFERENCES

1. Fahrenholz, F., *Alpha-secretase as a therapeutic target.* Curr Alzheimer Res, 2007. 4(4): p. 412-7.
2. Chakrabarti, E., et al., *Synthesis and biological evaluation of analogues of a novel inhibitor of beta-amyloid secretion.* J Med Chem, 2010. 53(14): p. 5302-19.
3. Braithwaite, S. P., et al., *Inhibition of c-Jun kinase provides neuroprotection in a model of Alzheimer's disease.* Neurobiol Dis, 2010. 39(3): p. 311-7.
4. Wolfe, M. S., *gamma-Secretase inhibitors and modulators for Alzheimer's disease.* J Neurochem, 2012. 120 Suppl 1: p. 89-98.

5. Ghosh, A. K., M. Brindisi, and J. Tang, *Developing beta-secretase inhibitors for treatment of Alzheimer's disease.* J Neurochem, 2012. 120 Suppl 1: p. 71-83.
6. Puzzo, D., et al., *Phosphodiesterase 5 inhibition improves synaptic function, memory, and amyloid-beta load in an Alzheimer's disease mouse model.* J Neurosci, 2009. 29(25): p. 8075-86.
7. Kozikowski, A. P., et al., *Searching for disease modifiers-PKC activation and HDAC inhibition—a dual drug approach to Alzheimer's disease that decreases Abeta production while blocking oxidative stress.* ChemMedChem, 2009. 4(7): p. 1095-105.
8. Lichtenthaler, S. F., *alpha-secretase in Alzheimer's disease: molecular identity, regulation and therapeutic potential.* J Neurochem, 2011. 116(1): p. 10-21.
9. Bandyopadhyay, S., et al., *Role of the APP non-amyloidogenic signaling pathway and targeting alpha-secretase as an alternative drug target for treatment of Alzheimer's disease.* Curr Med Chem, 2007. 14(27): p. 2848-64.
10. Huang, E. Y., et al., *Surface expression of Notch1 on thymocytes: correlation with the double-negative to double-positive transition.* J Immunol, 2003. 171(5): p. 2296-304.
11. Levy, O. A., J. J. Lah, and A. I. Levey, *Notch signaling inhibits PC12 cell neurite outgrowth via RBP-J-dependent and-independent mechanisms.* Dev Neurosci, 2002. 24(1): p. 79-88.
12. Corbett, A., J. Smith, and C. Ballard, *New and emerging treatments for Alzheimer's disease.* Expert Rev Neurother, 2012. 12(5): p. 535-43.
13. Postina, R., *Activation of alpha-secretase cleavage.* J Neurochem, 2012. 120 Suppl 1: p. 46-54.
14. Bielefeld-Sevigny, M., *AlphaLISA immunoassay platform—the "no-wash" high-throughput alternative to ELISA.* Assay Drug Dev Technol, 2009. 7(1): p. 90-2.
15. Cauchon, E., et al., *Development of a homogeneous immunoassay for the detection of angiotensin I in plasma using AlphaLISA acceptor beads technology.* Anal Biochem, 2009. 388(1): p. 134-9.
16. Chau, D. M., et al., *A novel high throughput 1536-well Notch1 gamma-secretase AlphaLISA assay.* Comb Chem High Throughput Screen, 2013. 16(6): p. 415-24.
17. Cosentino, G., *AlphaLISA assays to improve the vaccine development process.* Dev Biol (Basel), 2012. 134: p. 107-11.
18. Gan, X., et al., *[Primary establishment of an alphaLISA assay for detection of HAV IgM].* Zhonghua Shi Yan He Lin Chuang Bing Du Xue Za Zhi, 2012. 26(2): p. 139-41.
19. Mechaly, A., et al., *A novel homogeneous immunoassay for anthrax detection based on the AlphaLISA method: detection of B. anthracis spores and protective antigen (PA) in complex samples.* Anal Bioanal Chem, 2013. 405(12): p. 3965-72.
20. Peters, C. D., B. Jespersen, and R. Norregaard, *AlphaLISA versus ELISA-based detection of interleukin 18 in healthy subjects and patients with end-stage renal disease.* Scand J Clin Lab Invest, 2012. 72(8): p. 583-92.
21. Pfluger, M., et al., *A combined impedance and AlphaLISA-based approach to identify anti-inflammatory and barrier-protective compounds in human endothelium.* J Biomol Screen, 2013. 18(1): p. 67-74.
22. Schneider, S., et al., *Development of a homogeneous AlphaLISA ubiquitination assay using ubiquitin binding matrices as universal components for the detection of ubiquitinated proteins.* Biochim Biophys Acta, 2012. 1823(11): p. 2038-45.
23. Simard, J. R., et al., *Development and implementation of a high-throughput AlphaLISA assay for identifying inhibitors of EZH2 methyltransferase.* Assay Drug Dev Technol, 2013. 11(3): p. 152-62.
24. Waller, H., et al., *The use of AlphaLISA technology to detect interaction between hepatitis C virus-encoded NS5A and cyclophilin A.* J Virol Methods, 2010. 165(2): p. 202-10.
25. Wen, C. L., et al., *Development of an AlphaLISA assay to quantify serum core-fucosylated E-cadherin as a metastatic lung adenocarcinoma biomarker.* J Proteomics, 2012. 75(13): p. 3963-76.
26. Zhang, Y., et al., *Development of a homogeneous immunoassay based on the AlphaLISA method for the detection of chloramphenicol in milk, honey and eggs.* J Sci Food Agric, 2012. 92(9): p. 1944-7.
27. Zou, L. P., et al., *AlphaLISA for the determination of median levels of the free beta subunit of human chorionic gonadotropin in the serum of pregnant women.* J Immunoassay Immunochem, 2013. 34(2): p. 134-48.
28. Koo, E. H. and S. L. Squazzo, *Evidence that production and release of amyloid beta-protein involves the endocytic pathway.* J Biol Chem, 1994. 269(26): p. 17386-9.
29. Hayes, C. D., et al., *Striking reduction of amyloid plaque burden in an Alzheimer's mouse model after chronic administration of carmustine.* BMC Med, 2013. 11: p. 81.
30. Wang, H., et al., *AlphaLISA-based high-throughput screening assay to measure levels of soluble amyloid precursor protein alpha.* Anal Biochem, 2014. 459: p. 24-30.
31. Zhang, J. H., T. D. Chung, and K. R. Oldenburg, *A Simple Statistical Parameter for Use in Evaluation and Validation of High Throughput Screening Assays.* J Biomol Screen, 1999. 4(2): p. 67-73.
32. Hodder, P., et al., *Identification of metabotropic glutamate receptor antagonists using an automated high-throughput screening system.* Anal Biochem, 2003. 313 (2): p. 246-54.
33. Lakshmana, M. K., et al., *Novel role of RanBP9 in BACE1 processing of amyloid precursor protein and amyloid beta peptide generation.* J Biol Chem, 2009. 284(18): p. 11863-72.
34. Yao, Z. X., et al., *Ginkgo biloba extract (Egb 761) inhibits beta-amyloid production by lowering free cholesterol levels.* J Nutr Biochem, 2004. 15(12): p. 749-56.
35. Tokuhiro, S., et al., *The presenilin 1 mutation (M146V) linked to familial Alzheimer's disease attenuates the neuronal differentiation of NTera 2 cells.* Biochem Biophys Res Commun, 1998. 244(3): p. 751-5.
36. Cardoso, S. M., et al., *Mitochondria dysfunction of Alzheimer's disease cybrids enhances Abeta toxicity.* J Neurochem, 2004. 89(6): p. 1417-26.
37. Yang, L. B., et al., *Deficiency of complement defense protein CD59 may contribute to neurodegeneration in Alzheimer's disease.* J Neurosci, 2000. 20(20): p. 7505-9.
38. Andrews, P. W., et al., *Pluripotent embryonal carcinoma clones derived from the human teratocarcinoma cell line Tera-2. Differentiation in vivo and in vitro.* Lab Invest, 1984. 50(2): p. 147-62.
39. Pleasure, S. J., C. Page, and V. M. Lee, *Pure, postmitotic, polarized human neurons derived from NTera 2 cells provide a system for expressing exogenous proteins in terminally differentiated neurons.* J Neurosci, 1992. 12(5): p. 1802-15.

40. Chyung, A. S., et al., *Novel beta-secretase cleavage of beta-amyloid precursor protein in the endoplasmic reticulum/intermediate compartment of NT2N cells.* J Cell Biol, 1997. 138(3): p. 671-80.
41. Sung, Y. M., et al., *Mercaptoacetamide-based class II HDAC inhibitor lowers Abeta levels and improves learning and memory in a mouse model of Alzheimer's disease.* Exp Neurol, 2013. 239: p. 192-201.
42. Hanson, J. E., et al., *SAHA enhances synaptic function and plasticity in vitro but has limited brain availability in vivo and does not impact cognition.* PLoS One, 2013. 8(7): p. e69964.
43. Su, Y., et al., *Lithium, a common drug for bipolar disorder treatment, regulates amyloid-beta precursor protein processing.* Biochemistry, 2004. 43(22): p. 6899-908.
44. Schroter, T., et al., *Comparison of miniaturized time-resolved fluorescence resonance energy transfer and enzyme-coupled luciferase high-throughput screening assays to discover inhibitors of Rho-kinase II (ROCK-II).* J Biomol Screen, 2008. 13(1): p. 17-28.

Example 6

FIGS. 3.1A-Q includes embodiments of structures of thiazole tethered piperazine type compound. FIGS. 4.1A-C includes analogs of TP12055-244. FIG. 5.1 illustrates reagents to make the noted compounds (Analogs of TP12055-244). FIG. 6.1 illustrates compounds that can be made according to FIG. 5.1. FIGS. 7.1A-C and 8.1A-C illustrates embodiments of structures of thiazole tethered piperazine type compounds.

Example 7

FIGS. 9.1A and B illustrate that THPI-244 directly binds TrkA receptors as determined by label-free, real-time Octet Red detection system. FIG. 9.1A illustrates that biotinylated TrkA was loaded on to super-streptavidin (SSA) biosensors and after obtaining the baseline, were incubated with THPI-244 which dose-dependently bound TrkA receptors (Association). Incubation with kinetics buffer rapidly dissociated the binding. FIG. 9.1B illustrates analyzing the signal change as a function of THPI-244 concentration revealed KD value of 5.2 µM (p<0.001).

FIGS. 9.2A and B illustrate that THPI-244 increases TrkA and sAPPα in the mouse brain. FIG. 9.2A illustrates that THPI-244 was administered to mice by i.p. injections at 100 mg/kg body weight for 5 days and the brain lysates were subjected to immunoblots. Specific antibodies were used to detect TrkA and sAPPα. FIG. 9.2B illustrates the quantitation of immunoblot signals by imageJ which showed an increase of 78% of TrkA and 89% of sAPPα which were statistically significant. Data are mean±SEM, n=3*, p<0.05, ***, p<0.001.

FIG. 9.3 illustrates THPI-244 and TrkA are colocalized at the nerve terminals as revealed by transmission electron microscopy (TEM). Immunogold labeling of mouse brain hippocampal sections confirmed colocalization of APP (20 nm gold particles, indicated by red (darker) arrow heads) and TrkA (10 nm gold particles, yellow (lighter) arrow heads) at the nerve terminals.

FIGS. 9.4A and B illustrates that THPI-244 increases TrkA dimerization in NT2 cells. FIG. 9.4A illustrates that NT2 cells were treated with THPI-244 at 100 and 200 nM for 48 h and the cell lysates were subjected to immunoblots. TrkA monomer was detected at 140 kDa and dimer at 280 kDA. FIG. 9.4B illustrates that the quantitation of immunoblot signals by imageJ showed an increase of 82% of TrkA dimer at 100 nM and 134% at 200 nM, which were significant. Data are mean±SEM, n=4, , p<0.01, *, p<0.001 by ANOVA.

FIG. 9.5A illustrates the predicted binding modes of compound THPI-244 in the binding site of (1) 4PMP and (2) 4PMS TrkA structures. FIG. 9.5B illustrates the initial (gray (lighter)) and final (green (darker)) conformations of the compound THPI-244 inside the (1) 4PMP and (2) 4PMS structures.

Example 8

The following table illustrates Chemical structures and properties of THPI-244 analogs selected out of 37 analogs, and each have significant sAPPα increasing activity. Toxicity is the minimum dose for toxicity.

| Compounds | % sAPPα ↑ | % TrkA ↑ | % BBB |
|---|---|---|---|
| 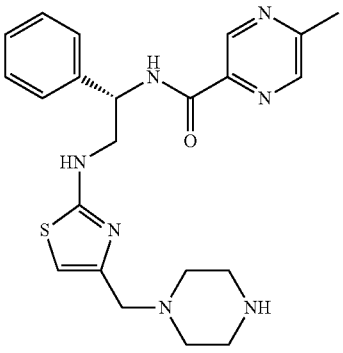<br>TPI-2336-55<br>Chemical Formula: $C_{22}H_{27}N_7OS$<br>Molecular Weight: 437.56 | 217 | 69 | 1.0 |

| Compounds | % sAPPα ↑ | % TrkA ↑ | % BBB |
|---|---|---|---|
| TPI-2336-99<br>Chemical Formula: $C_{16}H_{21}N_3OS$<br>Molecular Weight: 303.42 | 160 | 51 | 5.6 |
| TPI-2336-100<br>Chemical Formula: $C_{17}H_{23}N_3S$<br>Molecular Weight: 301.45 | 166 | 54 | 5.9 |
| THPI-244<br>Chemical Formula: $C_{32}H_{35}N_5O_2S$<br>Molecular Weight: 553.72 | 257 | 99 | 0.1 |

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

What is claimed is:
1. A composition comprising: a compound having the following structure:

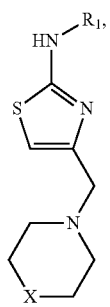

wherein X is CR$_2$R$_3$, NR$_4$, O, S, SO, or SO$_2$,
wherein R$_1$ is selected from

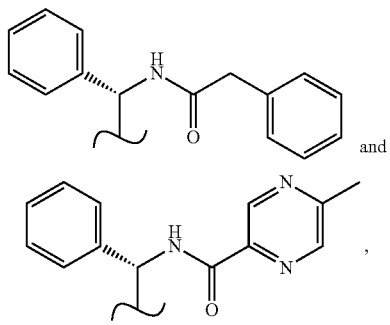

wherein R$_2$ and R$_3$ are each independently selected from the group consisting of: H, a straight or branched, saturated or unsaturated, cyclic or acyclic, chiral or achiral hydrocarbyl group with up to 20 carbon atoms, where each hydrocarbyl group is optionally substituted with a hydroxyl group, an alkoxy group, an amino group, a substituted amino group, a thio group, an alkylthio group, a guanidine group, an ureido group, a heterocyclyl group, an aryl group, and a heteroaryl group, and wherein R$_4$ is selected from the group consisting of: H, a straight or branched, saturated or unsaturated, cyclic or acyclic, chiral or achiral hydrocarbyl group with up to 20 carbon atoms, where each hydrocarbyl group is optionally substituted with a hydroxyl group, an alkoxy group, an amino group, a substituted amino group, a thio group, an alkylthio group, a guanidine group, an ureido group, a heterocyclyl group, an aryl group, and a heteroaryl group.

2. The composition of claim 1, wherein X is CH$_2$, NH, O, or

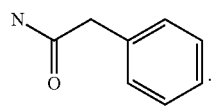

3. The composition of claim 1, wherein the compound has the following structure:

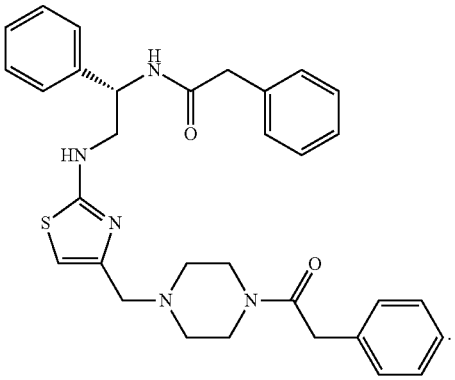 [SMILES: O=C(Cc1ccccc1)N[C@H](CNc1nc(CN2CCN(C(=O)Cc3ccccc3)CC2)cs1)c1ccccc1]

4. The composition of claim 1, wherein the compound has the following structure:

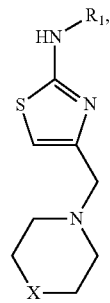

5. A pharmaceutical composition comprising a therapeutically effective amount of a compound, or a pharmaceutically acceptable salt of the compound, and a pharmaceutically acceptable carrier, to treat a disease, wherein the compound has the following structure:

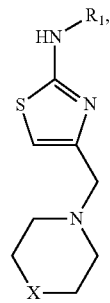

wherein X is CR$_2$R$_3$, NR$_4$, O, S, SO, or SO$_2$,
wherein R$_1$ is selected from

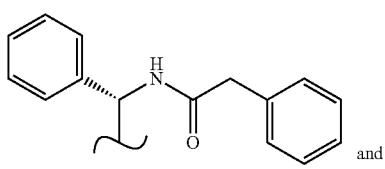

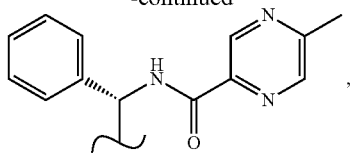
,

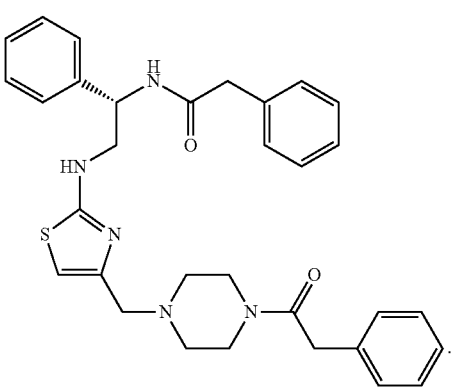

wherein $R_2$ and $R_3$ are each independently selected from the group consisting of: H, a straight or branched, saturated or unsaturated, cyclic or acyclic, chiral or achiral hydrocarbyl group with up to 20 carbon atoms, where each hydrocarbyl group is optionally substituted with a hydroxyl group, an alkoxy group, an amino group, a substituted amino group, a thio group, an alkylthio group, a guanidine group, an ureido group, a heterocyclyl group, an aryl group, and a heteroaryl group, and wherein $R_4$ is selected from the group consisting of: H, a straight or branched, saturated or unsaturated, cyclic or acyclic, chiral or achiral hydrocarbyl group with up to 20 carbon atoms, where each hydrocarbyl group is optionally substituted with a hydroxyl group, an alkoxy group, an amino group, a substituted amino group, a thio group, an alkylthio group, a guanidine group, an ureido group, a heterocyclyl group, an aryl group, and a heteroaryl group.

6. The pharmaceutical composition of claim 5, wherein X is $CH_2$, NH, O, or

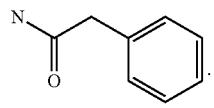

7. The pharmaceutical composition of claim 5, wherein the compound has the following structure:

8. The pharmaceutical composition of claim 5, wherein the compound has the following structure:

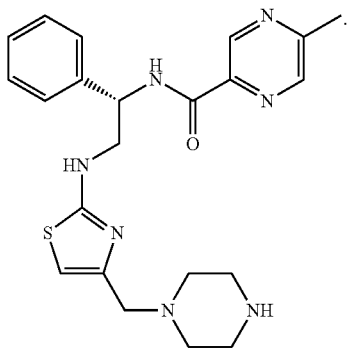 [SMILES: Cc1cnc(C(=O)N[C@H](CNc2nc(CN3CCNCC3)cs2)c2ccccc2)cn1]

* * * * *